United States Patent
Findeis et al.

(10) Patent No.: US 6,319,498 B1
(45) Date of Patent: *Nov. 20, 2001

(54) MODULATORS OF AMYLOID AGGREGATION

(75) Inventors: Mark A. Findeis, Cambridge; Howard Benjamin, Lexington; Marc B. Garnick, Brookline; Malcolm L. Gefter, Lincoln; Arvind Hundal, Brighton, all of MA (US); Laura Kasman, Athens, GA (US); Gary Musso, Hopkinton, MA (US); Ethan R. Signer, Cambridge, MA (US); James Wakefield, Brookline, MA (US); Michael J. Reed, Marietta, GA (US)

(73) Assignee: Praecis Pharmaceuticals Incorporated, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/617,267

(22) Filed: Mar. 14, 1996

Related U.S. Application Data

(63) Continuation-in-part of application No. 08/548,998, filed on Oct. 27, 1995, now abandoned, and a continuation-in-part of application No. 08/475,579, filed on Jun. 7, 1995, now Pat. No. 5,854,215, and a continuation-in-part of application No. 08/404,831, filed on Mar. 14, 1995, now Pat. No. 5,817,626.

(51) Int. Cl.[7] .................. A61K 38/02; A61K 38/17; C07K 1/113; C07K 14/47
(52) U.S. Cl. .................. 424/94.3; 424/94.61; 435/188; 435/206; 514/7; 514/12; 514/21; 530/307; 530/324; 530/345; 530/350; 530/359; 530/382; 530/394; 530/402; 530/410
(58) Field of Search ............................. 514/7, 12, 21; 435/188, 206; 424/94.3, 94.61; 530/307, 324, 325, 326, 345, 350, 359, 382, 394, 402, 410

(56) References Cited

U.S. PATENT DOCUMENTS

| | | | |
|---|---|---|---|
| 3,937,815 | * 2/1976 | Bruzzese et al. | 435/206 |
| 4,119,493 | * 10/1978 | Isowa et al. | 435/68.1 |

(List continued on next page.)

FOREIGN PATENT DOCUMENTS

| | | |
|---|---|---|
| 554 887 A1 | 8/1993 | (EP) . |
| 641 861 A1 | 3/1995 | (EP) . |

(List continued on next page.)

OTHER PUBLICATIONS

Berman et al. Receptor Binding Affinity, and Thermolysin . . . Life Sciences. vol. 44, No. 18, pp. 1267–1270, 1989.*

(List continued on next page.)

Primary Examiner—Jeffrey E. Russel
(74) Attorney, Agent, or Firm—Giulio A. DeConti, Jr.; Maria C. Laccotripe; Lahive & Cockfield, LLP

(57) ABSTRACT

Compounds that modulate the aggregation of amyloidogenic proteins or peptides are disclosed. The modulators of the invention can promote amyloid aggregation or, more preferably, can inhibit natural amyloid aggregation. In a preferred embodiment, the compounds modulate the aggregation of natural β amyloid peptides (β-AP). In a preferred embodiment, the β amyloid modulator compounds of the invention are comprised of an Aβ aggregation core domain and a modifying group coupled thereto such that the compound alters the aggregation or inhibits the neurotoxicity of natural β amyloid peptides when contacted with the peptides. Furthermore, the modulators are capable of altering natural β-AP aggregation when the natural β-APs are in a molar excess amount relative to the modulators. Pharmaceutical compositions comprising the compounds of the invention, and diagnostic and treatment methods for amyloidogenic diseases using the compounds of the invention, are also disclosed.

52 Claims, 4 Drawing Sheets

U.S. PATENT DOCUMENTS

| | | | |
|---|---|---|---|
| 4,652,627 | * 3/1987 | Kempe et al. | 530/307 |
| 5,010,174 | * 4/1991 | Hirose et al. | 530/307 |
| 5,338,663 | 8/1994 | Potter et al. | 435/4 |
| 5,470,951 | 11/1995 | Roberts | 530/330 |
| 5,698,672 | * 12/1997 | Labroo et al. | 530/326 |
| 5,710,244 | * 1/1998 | Labroo et al. | 530/307 |
| 5,817,626 | * 10/1998 | Findeis et al. | 514/12 |
| 5,854,204 | * 12/1998 | Findeis et al. | 514/2 |
| 5,854,215 | * 12/1998 | Findeis et al. | 514/12 |
| 5,985,242 | * 11/1999 | Findeis et al. | 424/9.1 |
| 6,120,768 | * 9/2000 | Griffiths et al. | 424/178.1 |

FOREIGN PATENT DOCUMENTS

| | | |
|---|---|---|
| 681 844 A1 | 11/1995 | (EP). |
| 464549 | * 1/1992 | (EP) ................................... 530/307 |
| WO 93/04194 | 3/1993 | (WO). |
| WO 94/28412 | 12/1994 | (WO). |
| WO 95/05394 | 2/1995 | (WO). |
| WO 95/05604 | 2/1995 | (WO). |
| 95/07093 | * 3/1995 | (WO). |
| WO 95/12815 | 5/1995 | (WO). |
| WO 95/20979 | 8/1995 | (WO). |

OTHER PUBLICATIONS

Hendrix et al. A Convergent Synthesis of the Amyloid Protein . . . J. Am. Chem. Soc. 1992, vol. 114, pp. 7930–7931.*

Koudinov et al. The Soluble Form of Alzheimer's Amyloid . . . Biochem. Biophys. Rec. Comm. Dec. 15, 1994, vol. 205, No. 2, pp. 1164–1171.*

Saito et al. Vector–Mediated Delivery of $^{125}$–I–labelled β–amyloid . . . PNAS USA. Oct. 1995, vol. 92, pp. 10227–10234.*

Barrow, Colin J. and Michael G. Zagorski (1991) "Solution Structures of β Peptide and Its Constituent Fragments: Relation to Amyloid Deposition" *Science* 253: 179–182.

Barrow, Colin J. et al. (1992) "Solution Conformations and Aggregational Properties of Synthetic Amyloid β–Peptides of Alzheimer's Disease: Analysis of Circular Dichroism Spectra" *J. Mol. Biol.* 225: 1075–1093.

Brown, Abraham M. et al. (1994) "Biotinylated and Cystein–Modified Peptides as Useful Reagents for Studying the Inhibition of Cathepsin G" *Analytical Biochemistry* 217: 139–147.

Burdick, Debra et al. (1992) "Assembly and Aggregation Properties of Synthetic Alzheimer's A4/β Amyloid Peptide Analogs" *Journal of Biological Chemistry* 267(1): 546–554.

Chantry, Andrew et al. (1992) "Biotinyl Analogues of Amylin as Biologically Active Probes for Amylin/CGRP Receptor Recognition" *FEBS* 296(2): 123–127.

Clements, Angela et al. (1993) "Aggregation of Alzheimer's Peptides" *Biochemical Society Transactions* 22: 16S.

Come, Jon H. et al. (1993) "A Kinetic Model for Amyloid Formation in the Prion Diseases: Importance of Seeding" *Proc. Natl. Acad. Sci. USA* 90: 5959–5963.

Evans, Krista C. et al. (1995) "Apolipoprotein E Is a Kinetic But Not a Thermodynamic Inhibitor of Amyloid Formation: Implications for the Pathogenesis and Treatment of Alzheimer Disease" *Proc. Natl. Acad. Sci. USA* 92: 763–767.

Kelly, Jeffery W. and Peter T. Lansbury, Jr. (1994) "A Chemical Approach to Elucidate the Mechanism of Transthyretin and β–Protein Amyloid Fibril Formation" *Int. J. Exp. Clin. Invest* 1: 186–205.

Kirschner, Daniel A. et al. (1987) "Synthetic Peptide Homologous to β Protein from Alzheimer Disease forms Amyloid–like Fibrils in vitro" *Proc. Natl. Acad. Sci. USA* 84: 6953–6957.

Klunk, William E. and Jay W. Pettegrew (1990) "Alzheimer's β–Amyloid Protein Is Covalently Modified When Dissolved in Formic Acid" *Journal of Neurochemistry* 54(6): 2050–2054.

Lansbury, Jr., Peter T. (1992) "In Pursuit of the Molecular Structure of Amyloid Plaque: New Technology Provides Unexpected and Critical Information" *Biochemistry* 31(30): 6866–6870.

LeVine, III, Harry (1993) "Thioflavine T Interaction with Synthetic Alzheimer's Disease β–Amyloid Peptides: Detection of Amyloid Aggregation in Solution" *Protein Science* 2: 404–410.

Maggio, John E. et al. (1992) "Reversible in vitro Growth of Alzheimer Disease β–Amyloid Plaques by Deposition of Labeled Amlyoid Peptide" *Proc. Natl. Acad. Sci. USA* 89: 5462–5466.

Miller, Brian T. et al. (1994) "Identification and Characterization of O–Biotinylated Hydroxy Amino Acid Residues in Peptides" *Analytical Biochemistry* 219: 240–248.

Orlando, Ron et al. (1992) "Covalent Modification of Alzheimer's Amyloid β–Peptide in Formic Acid Solutions" *Biochemical and Biophysical Research Communications* 184(2): 686–691.

Pike, Christian J. et al. (1993) "Neurodegeneration Induced by β–Amyloid Peptides in vitro: The Role of Peptide Assembly State" *Journal of Neuroscience* 13(4): 1676–1687.

Pike, Christian J. et al. (1995) "Structure–Activity Analyses of β–Amyloid Peptides: Contributions of the β25–35 Region to Aggregation and Neurotoxicity" *Journal of Neurochemistry* 64(1): 253–265.

Schwarzman, Alexander L. et al. (1994) "Transthyretin Sequesters Amyloid β Protein and Prevents Amyloid Formation" *Proc. Natl. Acad. Sci. USA* 91: 8368–8372.

Shearman, Mark S. et al. (1994) "Inhibition of PC12 Cell Redox Activity is a Specific, Early Indicator of the Mechanism of β–Amyloid–Mediated Cell Death" *Proc. Natl. Acad. Sci. USA* 91:1470–1474.

Shen, Chih–Lung et al. (1994) "Effect of Acid Predissolution of Fibril Size and Fibril Flexibility of Synthetic β–Amyloid Peptide" *Biophysical Journal* 67: 1238–1246.

Shen, Chih–Lung et al. (1993) "Light Scattering Analysis of Fibril Growth from the Amino–Terminal Fragment β(1–28) of β–Amyloid Peptide" *Biophysical Journal* 65: 2383–2395.

Snyder, Seth W. et al. (1994) "Amyloid–β Aggregation: Selective Inhibition of Aggregation in Mixtures of Amyloid with Different Chain Lengths" *Biophysical Journal* 67: 1216–1228.

Sonnenberg–Reines, J. et al. (1993) "Biotinylated and Cysteine Modified Peptides as Useful Reagents for Studying the Inhibition of Putative N–terminal B–Amyloid Peptide Enzymes," *Society for Neuroscience Abstracts* vol. 19 (1–3), p. 861.

Soreghan, Brian et al. (1994) "Surfactant Properties of Alzheimer's Aβ Peptides and the Mechanism of Amyloid Aggregation" *The Journal of Biological Chemistry* 269(46): 28551–28554.

Sorimachi, Kay and David J. Craik (1994) "Structure Determination of Extracellular Fragments of Amyloid Proteins Involved in Alzheimer's Disease and Dutch–type Hereditary Cerebral Haemorrhage with Amyloidosis" *Eur. J. Biochem* 219: 237–251.

Strittmatter, Warren J. et al. (1993) "Binding of Human Apolipoprotein E to Synthetic Amyloid β Peptide: Isoform-Specific Effects and Implications for Late–Onset Alzheimer Disease" *Proc. Natl. Acad. Sci. USA* 90: 8098–8102.

Tomiyama, Takami et al. (1994) "Racemization of Asp$^{23}$ Residue Affects the Aggregation Properties of Alzheimer Amyloid β Protein Analogues" *J. Biol. Chem.* 269(14): 10205–10208.

Tomski, Sharon J. and Regina M. Murphy (1992) "Kinetics of Aggregation of Synthetic β–Amyloid Peptide" *Archives of Biochemistry and Biophysics* 294(2): 630–638.

Vitek, Michael P. et al. (1994) "Advanced Glycation End Products Contribute to Amyloidosis in Alzheimer Disease" *Proc. Natl. Acad. Sci. USA* 91: 4766–4770.

Vyas, S. B. et al. "Characterization of Aggregation in Alzheimer β–protein Using Synthetic Peptide Fragments on Reverse–Phase Matrix," in *Peptides, Chemistry and Biology* (J.A. Smith and J.E. Rivier, eds.), ESCOM, Leiden, 1992, pp. 278–279.

Weinreb, Paul H. et al. (1994) "Peptide Models of a Hydrophobic Cluster at the C–Terminus of the β–Amyloid Protein" *Journal of the American Chemical Society* 116(23): 10835–10836.

Woods, S. J. et al. (1995) "Prolines and Amyloidogenicity in Fragments of the Alzheimer's Peptide β/A4," *Biochemistry* vol. 34, 724–730.

Fabian, Heinz et al. (1993) "Comparative Analysis of Human and Dutch–Type Alzheimer β–Amyloid Peptides by Infrared Spectroscopy and Circular Dichroism" *Biochemical and Biophysical Research Communications* 191(1): 232–239.

Fabian, Heinz et al. (1994) "Synthetic Post–Translationally Modified Human Aβ Peptide Exhibits a Markedly Increased Tendency to Form β–Pleated Sheets in vitro" *Eur. J. Biochem.* 221: 959–964.

Flood, J. F. et al., (1994) "Topography of a Binding Site for Small Amnestic Peptides Deduced from Structure–Activity Studies: Relation to Amnestic Effect of Amyloid β Protein," *Proc. Natl. Acad. Sci. USA* vol. 91, pp. 380–384.

Fraser, Paul E. et al. (1994) "Conformation and Fibrilogenesis of Alzheimer Aβ Peptides with Selected Substitution of Charged Residues," *J. Mol. Biol.* 244: 64–73.

Fraser, Paul E. et al. (1992) "Fibril Formation by Primate, Rodent, and Dutch–Hemorrhagic Analogues of Alzheimer Amyloid β–Protein" *Biochemistry* 31: 10716–10723.

Gorevic, PD et al. (1987) "Ten to Fourteen Residue Peptides of Alzheimer's Disease Protein are Sufficient for Amyloid Fibril Formation and Its Characteristic Xray Diffraction Pattern" *Biochemical and Biophysical Research Communications* 147(2): 854–862.

Growing, Eric et al. (1994) "Chemical Characterization of Aβ 17–42 Peptide, a Component of Diffuse Amyloid Deposits of Alzheimer Disease" *J. Biol. Chem.* 269(15): 10987–10990.

Halverson, Kurt et al. (1990) "Molecular Determinants of Amyloid Deposition in Alzheimer's Disease: Conformational Studies of Synthetic β–Protein Framgents" *Biochemistry* 29(11): 2639–2644.

Hansen, Morten B. et al. (1989) "Re–examination and Further Development of a Precise and Rapid Dye Method for Measuring Cell Growth/Cell Kill" *J. Immunol. Meth.* 119: 203–210.

Hardy, John A. and Gerald A. Higgins (1992) "Alzheimer's Disease: The Amyloid Cascade Hypothesis" *Science* 256: 184–185.

Hilbich, Caroline et al. (1991) "Aggregation and Secondary Structure of Synthetic Amyloid βA4 Peptides of Alzheimer's Disease" *J. Mol. Biol.* 218: 149–163.

Hilbich, Caroline et al. (1991) "Human and Rodent Sequence Analogs of Alzheimer's Amyloid β A4 Share Similar Properties and Can Be Solubilized in Buffers of pH 7.4" *Eur. J. Biochem.* 201: 61–69.

Hilibich, Caroline et al. (1992) "Substitutions of Hydrophobic Amino Acids Reduce the Amyloidogenicity of Alzheimer's Disease βA4 Peptides" *J. Mol. Biol.* 228: 460–473.

Inouye, H. et al. (1993) "Structure of Beta–Crystallite Assemblies Formed by Alzheimer β–Amyloid Protein Analogs: Analysis by X–ray Diffraction," *Chemical Abstracts* vol. 119, p. 349, Abstract No. 119: 23024a.

Jarrett, Joseph T. and Peter T. Lansbury, Jr. (1993) "Seeding 'One–Dimensional Crystallization' of Amyloid: A Pathogenic Mechanism in Alzheimer's Disease and Scrapie?" *Cell* 73: 1055–1058.

Jarrett, Joseph T. et al. (1993) "The Carboxy Terminus of the β Amyloid Protein Is Critical for the Seeding of Amyloid Formation: Implications for the Pathogenesis of Alzheimer's Disease" *Biochemistry* 32(18): 4693–4697.

Jarrett, Joseph T. et al. (1994) "Models of the β Protein C–Terminus: Differences in Amyloid Structure May Lead to Segregation of 'Long' and 'Short' Fibrils" *Journal of the American Chemical Society* 116(21): 9741–9742.

\* cited by examiner

US 6,319,498 B1

MODULATORS OF AMYLOID AGGREGATION

RELATED APPLICATIONS

This application is a continuation-in-part of U.S. patent application Ser. No. 08/404,831, filed Mar. 14, 1995, now U.S. Pat. No. 5,817,626, and U.S. patent application Ser. No. 08/475,579, filed Jun. 7, 1995, now U.S. Pat. No. 5,854,215, and U.S. patent application Ser. No. 08/548,998, filed Oct. 27, 1995, now abandoned the entire contents of each of which are hereby incorporated by reference.

BACKGROUND OF THE INVENTION

Alzheimer's disease (AD), first described by the Bavarian psychiatrist Alois Alzheimer in 1907, is a progressive neurological disorder that begins with short term memory loss and proceeds to disorientation, impairment of judgement and reasoning and, ultimately, dementia. The course of the disease usually leads to death in a severely debilitated, immobile state between four and 12 years after onset. AD has been estimated to afflict 5 to 11 percent of the population over age 65 and as much as 47 percent of the population over age 85. The societal cost for managing AD is upwards of 80 billion dollars annually, primarily due to the extensive custodial care required for AD patients. Moreover, as adults born during the population boom of the 1940's and 1950's approach the age when AD becomes more prevalent, the control and treatment of AD will become an even more significant health care problem. Currently, there is no treatment that significantly retards the progression of the disease. For reviews on AD, see Selkoe, D. J. *Sci. Amer.*, November 1991, pp. 68–78; and Yankner, B. A. et al. (1991) *N. Eng. J. Med.* 325:1849–1857.

It has recently been reported (Games et al. (1995) *Nature* 373:523–527) that an Alzheimer-type neuropathology has been created in transgenic mice. The transgenic mice express high levels of human mutant amyloid precursor protein and progressively develop many of the pathological conditions associated with AD.

Pathologically, AD is characterized by the presence of distinctive lesions in the victim's brain. These brain lesions include abnormal intracellular filaments called neurofibrillary tangles (NTFs) and extracellular deposits of amyloidogenic proteins in senile, or amyloid, plaques. Amyloid deposits are also present in the walls of cerebral blood vessels of AD patients. The major protein constituent of amyloid plaques has been identified as a 4 kilodalton peptide called β-amyloid peptide (β-AP)(Glenner, G. G. and Wong, C. W. (1984) *Biochem. Biophys. Res. Commun.* 120:885–890; Masters, C. et al. (1985) *Proc. Natl. Acad. Sci. USA* 82:4245–4249). Diffuse deposits of β-AP are frequently observed in normal adult brains, whereas AD brain tissue is characterized by more compacted, dense-core β-amyloid plaques. (See e.g., Davies, L. et al. (1988) *Neurology* 38:1688–1693). These observations suggest that β-AP deposition precedes, and contributes to, the destruction of neurons that occurs in AD. In further support of a direct pathogenic role for β-AP, β-amyloid has been shown to be toxic to mature neurons, both in culture and in vivo. Yankner, B. A. et al. (1989) *Science* 245:417–420; Yankner, B. A. et al. (1990) *Proc. Natl. Acad. Sci. USA* 87:9020–9023; Roher, A. E. et al. (1991) *Biochem. Biophys. Res. Commun.* 174:572–579; Kowall, N. W. et al. (1991) *Proc. Natl. Acad. Sci. USA* 88:7247–7251. Furthermore, patients with hereditary cerebral hemorrhage with amyloidosis-Dutch-type (HCHWA-D), which is characterized by diffuse β-amyloid deposits within the cerebral cortex and cerebrovasculature, have been shown to have a point mutation that leads to an amino acid substitution within β-AP. Levy, E. et al. (1990) *Science* 248:1124–1126. This observation demonstrates that a specific alteration of the β-AP sequence can cause β-amyloid to be deposited.

Natural β-AP is derived by proteolysis from a much larger protein called the amyloid precursor protein (APP). Kang, J. et al. (1987) *Nature* 325:733; Goldgaber, D. et al. (1987) *Science* 235:877; Robakis, N. K. et al. (1987) *Proc. Natl. Acad. Sci. USA* 84:4190; Tanzi, R. E. et al. (1987) *Science* 235:880. The APP gene maps to chromosome 21, thereby providing an explanation for the β-amyloid deposition seen at an early age in individuals with Down's syndrome, which is caused by trisomy of chromosome 21. Mann, D. M. et al (1989) *Neuropathol. Appl. Neurobiol.* 15:317; Rumble, B. et al. (1989) *N. Eng. J. Med.* 320:1446. APP contains a single membrane spanning domain, with a long amino terminal region (about two-thirds of the protein) extending into the extracellular environment and a shorter carboxy-terminal region projecting into the cytoplasm. Differential splicing of the APP messenger RNA leads to at least five forms of APP, composed of either 563 amino acids (APP-563), 695 amino acids (APP-695), 714 amino acids (APP-714), 751 amino acids (APP-751) or 770 amino acids (APP-770).

Within APP, naturally-occurring β amyloid peptide begins at an aspartic acid residue at amino acid position 672 of APP-770. Naturally-occurring β-AP derived from proteolysis of APP is 39 to 43 amino acid residues in length, depending on the carboxy-terminal end point, which exhibits heterogeneity. The predominant circulating form of β-AP in the blood and cerebrospinal fluid of both AD patients and normal adults is β1-40 ("short β"). Seubert, P. et al. (1992) *Nature* 359:325; Shoji, M. et al. (1992) *Science* 258:126. However, β1-42 and β1-43 ("long β") also are forms in β-amyloid plaques. Masters, C. et al. (1985) *Proc. Natl. Acad. Sci. USA* 82:4245; Miller, D. e al. (1993) *Arch. Biochem. Biophys.* 301:41; Mori, H. et al. (1992) *J. Biol. Chem.* 267:17082. Although the precise molecular mechanism leading to β-APP aggregation and deposition is unknown, the process has been likened to that of nucleation-dependent polymerizations, such as protein crystallization, microtubule formation and actin polymerization. See e.g., Jarrett, J. T. and Lansbury, P. T. (1993) *Cell* 73:1055–1058. In such processes, polymerization of monomer components does not occur until nucleus formation. Thus, these processes are characterized by a lag time before aggregation occurs, followed by rapid polymerization after nucleation. Nucleation can be accelerated by the addition of a "seed" or preformed nucleus, which results in rapid polymerization. The long β forms of β-AP have been shown to act as seeds, thereby accelerating polymerization of both long and short β-AP forms. Jarrett, J. T. et al. (1993) *Biochemistry* 32:4693.

In one study, in which amino acid substitutions were made in β-AP, two mutant β peptides were reported to interfere with polymerization of non-mutated β-AP when the mutant and non-mutant forms of peptide were mixed. Hilbich, C. et al. (1992) *J. Mol. Biol.* 228:460–473. However, equimolar amounts of the mutant and non-mutant (i.e., natural) β amyloid peptides were used to see this effect and the mutant peptides were reported to be unsuitable for use in vivo. Hilbich, C. et al. (1992), supra.

SUMMARY OF THE INVENTION

This invention pertains to compounds, and pharmaceutical compositions thereof, that can modulate the aggregation of amyloidogenic proteins and peptides, in particular compounds that can modulate the aggregation of natural β amyloid peptides (β-AP) and inhibit the neurotoxicity of natural β-APs. In one embodiment, the invention provides an amyloid modulator compound comprising an amyloidogenic protein, or peptide fragment thereof, coupled directly or indirectly to at least one modifying group such that the compound modulates the aggregation of natural amyloid proteins or peptides when contacted with the natural amyloidogenic proteins or peptides. Preferably, the compound inhibits aggregation of natural amyloidogenic proteins or peptides when contacted with the natural amyloidogenic proteins or peptides. The amyloidogenic protein, or peptide fragment thereof, can be, for example, selected from the group consisting of transthyretin (TTR), prion protein (PrP), islet amyloid polypeptide (IAPP), atrial natriuretic factor (ANF), kappa light chain, lambda light chain, amyloid A, procalcitonin, cystatin C, β2 microglobulin, ApoA-I, gelsolin, calcitonin, fibrinogen and lysozyme.

In the most preferred embodiment of the invention, the compound modulates the aggregation of natural β-AP. The invention provides a β-amyloid peptide compound comprising a formula:

wherein Xaa is a β-amyloid peptide having an amino-terminal amino acid residue corresponding to position 668 of β-amyloid precursor protein-770 (APP-770) or to a residue carboxy-terminal to position 668 of APP-770, A is a modifying group attached directly or indirectly to the β-amyloid peptide of the compound such that the compound inhibits aggregation of natural β-amyloid peptides when contacted with the natural β-amyloid peptides, and n is an integer selected such that the compound inhibits aggregation of natural β-amyloid peptides when contacted with the natural β-amyloid peptides.

In one embodiment, at least one A group is attached directly or indirectly to the amino terminus of the β-amyloid peptide of the compound. In another embodiment, at least one A group is attached directly or indirectly to the carboxy terminus of the β-amyloid peptide of the compound. In yet another embodiment, at least one A group is attached directly or indirectly to a side chain of at least one amino acid residue of the β-amyloid peptide of the compound.

The invention also provides a β-amyloid modulator compound comprising an Aβ aggregation core domain (ACD) coupled directly or indirectly to at least one modifying group (MG) such that the compound modulates the aggregation or inhibits the neurotoxicity of natural β-amyloid peptides when contacted with the natural β-amyloid peptides. Preferably, the Aβ aggregation core domain is modeled after a subregion of natural β-amyloid peptide between 3 and 10 amino acids in length.

The invention also provides β-amyloid modulator compound comprising a formula:

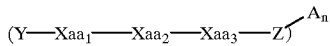

wherein $Xaa_1$, $Xaa_2$ and $Xaa_3$ are each amino acid structures and at least two of $Xaa_1$, $Xaa_2$ and $Xaa_3$ are, independently, selected from the group consisting of a leucine structure, a phenylalanine structure and a valine structure;

Y, which may or may not be present, is a peptidic structure having the formula $(Xaa)_a$, wherein Xaa is any amino acid structure and a is an integer from 1 to 15;

Z, which may or may not be present, is a peptidic structure having the formula $(Xaa)_b$, wherein Xaa is any amino acid structure and b is an integer from 1 to 15; and A is a modifying group attached directly or indirectly to the compound and n is an integer;

$Xaa_1$, $Xaa_2$, $Xaa_3$, Y, Z, A and n being selected such that the compound modulates the aggregation or inhibits the neurotoxicity of natural β-amyloid peptides when contacted with the natural β-amyloid peptides. In a preferred embodiment, $Xaa_1$ and $Xaa_2$ are each phenylalanine structures. In another preferred embodiment $Xaa_2$ and $Xaa_3$ are each phenylalanine structures.

The invention further provides a β-amyloid modulator compound comprising a formula:

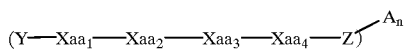

wherein $Xaa_1$ and $Xaa_3$ are amino acid structures;

$Xaa_2$ is a valine structure;

$Xaa_4$ is a phenylalanine structure;

Y, which may or may not be present, is a peptidic structure having the formula $(Xaa)_a$, wherein Xaa is any amino acid structure and a is an integer from 1 to 15;

Z, which may or may not be present, is a peptidic structure having the formula $(Xaa)_b$, wherein Xaa is any amino acid structure and b is an integer from 1 to 15; and A is a modifying group attached directly or indirectly to the compound and n is an integer;

$Xaa_1$, $Xaa_3$, Y, Z, A and n being selected such that the compound modulates the aggregation or inhibits the neurotoxicity of natural β-amyloid peptides when contacted with the natural β-amyloid peptides. In a preferred embodiment, $Xaa_1$ is a leucine structure and $Xaa_3$ is phenylalanine structure.

The invention still further provides a compound comprising the formula:

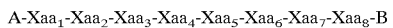

wherein $Xaa_1$ is a histidine structure;

$Xaa_2$ is a glutamine structure;

$Xaa_3$ is a lysine structure;

$Xaa_4$ is a leucine structure;

$Xaa_5$ is a valine structure;

$Xaa_6$ is a phenylalanine structure;

$Xaa_7$ is a phenylalanine structure;

$Xaa_8$ is an alanine structure;

A and B are modifying groups attached directly or indirectly to the amino terminus and carboxy terminus, respectively, of the compound;

and wherein $Xaa_1$-$Xaa_2$-$Xaa_3$, $Xaa_1$-$Xaa_2$ or $Xaa_1$ may or may not be present;

$Xaa_8$ may or may not be present; and at least one of A and B is present.

The invention still further provides a β-amyloid modulator compound comprising a modifying group attached directly or indirectly to a peptidic structure, wherein the peptidic structure comprises amino acid structures having an amino acid sequence selected from the group consisting of His-Gln-Lys-Leu-Val-Phe-Phe-Ala (SEQ ID NO: 5), His-Gln-Lys-Leu-Val-Phe-Phe (SEQ ID NO: 6), Gln-Lys-Leu-Val-Phe-Phe-Ala (SEQ ID NO: 7), Gln-Lys-Leu-Val-Phe-Phe (SEQ ID NO: 8), Lys-Leu-Val-Phe-Phe-Ala (SEQ ID NO: 9), Lys-Leu-Val-Phe-Phe (SEQ ID NO: 10), Leu-Val-Phe-Phe-Ala (SEQ ID NO: 11), Leu-Val-Phe-Phe (SEQ ID NO: 12), Leu-Ala-Phe-Phe-Ala (SEQ ID NO: 13), Val-Phe-Phe (SEQ ID NO: 19), Phe-Phe-Ala (SEQ ID NO: 20), Phe-Phe-Val-Leu-Ala (SEQ ID NO: 21), Leu-Val-Phe-Phe-Lys (SEQ ID NO: 22), Leu-Val-Iodotyrosine-Phe-Ala (SEQ ID NO: 23), Val-Phe-Phe-Ala (SEQ ID NO: 24), Ala-Val-Phe-Phe-Ala (SEQ ID NO: 25), Leu-Val-Phe-Iodotyrosine-Ala (SEQ ID NO: 26), Leu-Val-Phe-Phe-Ala-Glu (SEQ ID NO: 27), Phe-Phe-Val-Leu (SEQ ID NO: 28), Phe-Lys-Phe-Val-Leu (SEQ ID NO: 29), Lys-Leu-Val-Ala-Phe (SEQ ID NO: 30), Lys-Leu-Val-Phe-Phe-βAla (SEQ ID NO: 31) and Leu-Val-Phe-Phe-DAla (SEQ ID NO: 32).

In the compounds of the invention comprising a modifying group, preferably the modifying group comprises a cyclic, heterocyclic or polycyclic group. Preferred modifying groups contains a cis-decalin group, such as a cholanoyl structure. Preferred modifying groups include a cholyl group, a biotin-containing group, a diethylene-triaminepentaacetyl group, a (−)-menthoxyacetyl group, a fluorescein-containing group or an N-acetylneuraminyl group.

The compounds of the invention can be further modified, for example to alter a pharmacokinetic property of the compound or to label the compound with a detectable substance. Preferred radioactive labels are radioactive iodine or technetium.

The invention also provides a β-amyloid modulator which inhibits aggregation of natural β-amyloid peptides when contacted with a molar excess amount of natural β-amyloid peptides.

The invention also provides a β-amyloid peptide compound comprising an amino acid sequence having at least one amino acid deletion compared to βAP$_{1-39}$, such that the compound inhibits aggregation of natural β-amyloid peptides when contacted with the natural β-amyloid peptides. In one embodiment, the compound has at least one internal amino acid deleted compared to βAP$_{1-39}$. In another embodiment, the compound has at least one N-terminal amino acid deleted compared to βAP$_{1-39}$. In yet another embodiment, the compound has at least one C-terminal amino acid deleted compared to βAP$_{1-39}$. Preferred compounds include βAP$_{6-20}$ (SEQ ID NO: 4), βAP$_{16-30}$ (SEQ ID NO: 14), βAP$_{1-20, 26-40}$ (SEQ ID NO: 15) and EEVVHHHHQQ-βAP$_{16-40}$ (SEQ ID NO: 16).

The compounds of the invention can be formulated into pharmaceutical compositions comprising the compound and a pharmaceutically acceptable carrier. The compounds can also be used in the manufacture of a medicament for the diagnosis or treatment of an amyloidogenic disease.

Another aspect of the invention pertains to diagnostic and treatment methods using the compounds of the invention. The invention provides a method for inhibiting aggregation of natural β-amyloid peptides, comprising contacting the natural β-amyloid peptides with a compound of the invention such that aggregation of the natural β-amyloid peptides is inhibited. The invention also provides a method for inhibiting neurotoxicity of natural β-amyloid peptides, comprising contacting the natural β-amyloid peptides with a compound of the invention such that neurotoxicity of the natural β-amyloid peptides is inhibited.

In another embodiment, the invention provides a method for detecting the presence or absence of natural β-amyloid peptides in a biological sample, comprising contacting a biological sample with a compound of the invention and detecting the compound bound to natural β-amyloid peptides to thereby detect the presence or absence of natural β-amyloid peptides in the biological sample. In one embodiment, the β-amyloid modulator compound and the biological sample are contacted in vitro. In another embodiment, the β-amyloid modulator compound is contacted with the biological sample by administering the β-amyloid modulator compound to a subject. For in vivo administration, preferably the compound is labeled with radioactive technetium or radioactive iodine.

In another embodiment, the invention provides a method for detecting natural β-amyloid peptides to facilitate diagnosis of a β-amyloidogenic disease, comprising contacting a biological sample with a compound of the invention and detecting the compound bound to natural β-amyloid peptides to facilitate diagnosis of a β-amyloidogenic disease. In one embodiment, the β-amyloid modulator compound and the biological sample are contacted in vitro. In another embodiment, the β-amyloid modulator compound is contacted with the biological sample by administering the β-amyloid modulator compound to a subject. For in vivo administration, preferably the compound is labeled with radioactive technetium or radioactive iodine. Preferably, the method facilitates diagnosis of Alzheimer's disease.

The invention also provides a method for treating a subject for a disorder associated with amyloidosis, comprising administering to the subject a therapeutically or prophylactically effective amount of a compound of the invention such that the subject is treated for a disorder associated with amyloidosis. The method can be used to treat disorders is selected, for example, from the group consisting of familial amyloid polyneuropathy (Portuguese, Japanese and Swedish types), familial amyloid cardiomyopathy (Danish type), isolated cardiac amyloid, systemic senile amyloidosis, scrapie, bovine spongiform encephalopathy, Creutzfeldt-Jakob disease, Gerstmann-Straussler-Scheinker syndrome, adult onset diabetes, insulinoma, isolated atrial amyloidosis, idiopathic (primary) amyloidosis, myeloma or macroglobulinemia-associated amyloidosis, primary localized cutaneous nodular amyloidosis associated with Sjogren's syndrome, reactive (secondary) amyloidosis, familial Mediterranean Fever and familial amyloid nephropathy with urticaria and deafness (Muckle-Wells syndrome), hereditary cerebral hemorrhage with amyloidosis of Icelandic type, amyloidosis associated with long term hemodialysis, hereditary non-neuropathic systemic amyloidosis (familial amyloid polyneuropathy III), familial amyloidosis of Finnish type, amyloidosis associated with medullary carcinoma of the thyroid, fibrinogen-associated hereditary renal amyloidosis and lysozyme-associated hereditary systemic amyloidosis.

In a preferred embodiment, the invention provides a method for treating a subject for a disorder associated with β-amyloidosis, comprising administering to the subject a therapeutically or prophylactically effective amount of a compound of the invention such that the subject is treated for a disorder associated with β-amyloidosis. Preferably the disorder is Alzheimer's disease.

In yet another embodiment, the invention provides a method for treating a subject for a disorder associated with β-amyloidosis, comprising administering to the subject a recombinant expression vector encoding a peptide compound of the invention such that the compound is synthesized in the subject and the subject is treated for a disorder associated with β-amyloidosis. Preferably, the disorder is Alzheimer's disease.

DETAILED DESCRIPTION OF THE INVENTION

Figure 1:
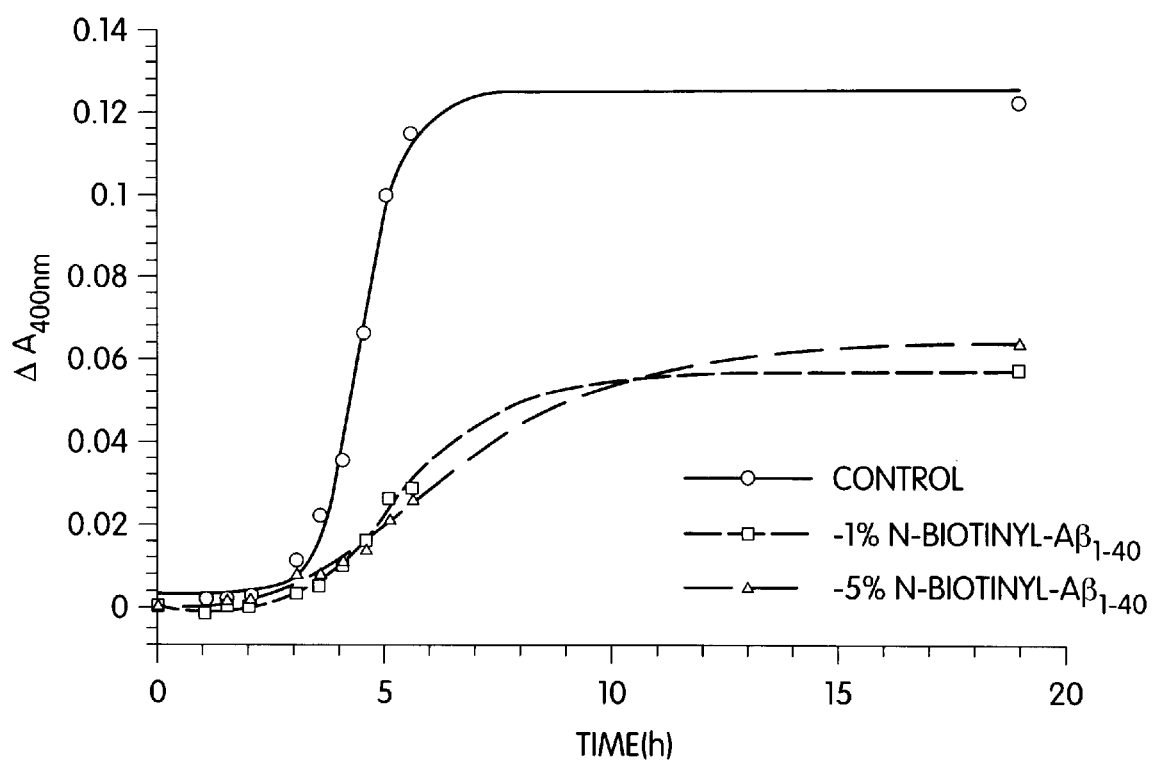
FIG. 1 is a graphic representation of the turbidity of a β-AP$_{1-40}$ solution, as measured by optical density at 400 nm, either in the absence of a β-amyloid modulator or in the presence of the β-amyloid modulator N-biotinyl-βAP$_{1-40}$ (1%, or 5%).

This invention pertains to compounds, and pharmaceutical compositions thereof, that can modulate the aggregation of amyloidogenic proteins and peptides, in particular compounds that can modulate the aggregation of natural β amyloid peptides (β-AP) and inhibit the neurotoxicity of natural β-APs. A compound of the invention that modulates aggregation of natural β-AP, referred to herein interchangeably as a β amyloid modulator compound, a β amyloid modulator or simply a modulator, alters the aggregation of natural β-AP when the modulator is contacted with natural β-AP. Thus, a compound of the invention acts to alter the natural aggregation process or rate for β-AP, thereby disrupting this process. Preferably, the compounds inhibit β-AP aggregation. Furthermore, the invention provides subregions of the β amyloid peptide that are sufficient, when appropriately modified as described herein, to alter (and preferably inhibit) aggregation of natural β amyloid peptides when contacted with the natural β amyloid peptides. In particular, preferred modulator compounds of the invention are comprised of a modified form of an Aβ aggregation core domain, modeled after the aforementioned β subregion (as described further below), which is sufficient to alter (and preferably inhibit) the natural aggregation process or rate for β-AP. This Aβ aggregation core domain can comprises as few as three amino acid residues (or derivative, analogues or mimetics thereof). Moreover, while the amino acid sequence of the Aβ aggregation core domain can directly correspond to an amino acid sequence found in natural β-AP, it is not essential that the amino acid sequence directly correspond to a β-AP sequence. Rather, amino acid residues derived from a preferred subregion of β-AP (a hydrophobic region centered around positions 17–20) can be rearranged in order and/or substituted with homologous residues within a modulator compound of the invention and yet maintain their inhibitory activity (described further below).

The β amyloid modulator compounds of the invention can be selected based upon their ability to inhibit the aggregation of natural β-AP in vitro and/or inhibit the neurotoxicity of natural β-AP fibrils for cultured cells (using assays described herein). Accordingly, the preferred modulator compounds inhibit the aggregation of natural β-AP and/or inhibit the neurotoxicity of natural β-AP. However, modulator compounds selected based on one or both of these properties may have additional properties in vivo that may be beneficial in the treatment of amyloidosis. For example, the modulator compound may interfere with processing of natural β-AP (either by direct or indirect protease inhibition) or by modulation of processes that produce toxic β-AP, or other APP fragments, in vivo. Alternatively, modulator compounds may be selected based on these latter properties, rather than inhibition of Aβ aggregation in vitro. Moreover, modulator compounds of the invention that are selected based upon their interaction with natural β-AP also may interact with APP or with other APP fragments.

As used herein, a "modulator" of β-amyloid aggregation is intended to refer to an agent that, when contacted with natural β amyloid peptides, alters the aggregation of the natural β amyloid peptides. The term "aggregation of β amyloid peptides" refers to a process whereby the peptides associate with each other to form a multimeric, largely insoluble complex. The term "aggregation" further is intended to encompass β amyloid fibril formation and also encompasses β-amyloid plaques.

The terms "natural β-amyloid peptide", "natural β-AP" and "natural Aβ peptide", used interchangeably herein, are intended to encompass naturally occurring proteolytic cleavage products of the β amyloid precursor protein (APP) which are involved in β-AP aggregation and β-amyloidosis. These natural peptides include β-amyloid peptides having 39–43 amino acids (i.e., Aβ$_{1-39}$, Aβ$_{1-40}$, Aβ$_{1-41}$, Aβ$_{1-42}$ and Aβ$_{1-43}$). The amino-terminal amino acid residue of natural β-AP corresponds to the aspartic acid residue at position 672 of the 770 amino acid residue form of the amyloid precursor protein ("APP-770"). The 43 amino acid long form of natural β-AP has the amino acid sequence

DAEFRHDSGYEVHHQKLVFFAEDVGSNK-GAIIGLMVGGVVIAT (also shown in SEQ ID NO: 1), whereas the shorter forms have 1–4 amino acid residues deleted from the carboxy-terminal end. The amino acid sequence of APP-770 from position 672 (i.e., the amino-terminus of natural β-AP) to its C-terminal end (103 amino acids) is shown in SEQ ID NO: 2. The preferred form of natural β-AP for use in the aggregation assays described herein is Aβ$_{1-40}$.

In the presence of a modulator of the invention, aggregation of natural β amyloid peptides is "altered" or "modulated". The various forms of the term "alteration" or "modulation" are intended to encompass both inhibition of β-AP aggregation and promotion of β-AP aggregation. Aggregation of natural β-AP is "inhibited" in the presence of the modulator when there is a decrease in the amount and/or rate of β-AP aggregation as compared to the amount and/or rate of β-AP aggregation in the absence of the modulator. The various forms of the term "inhibition" are intended to include both complete and partial inhibition of β-AP aggregation. Inhibition of aggregation can be quantitated as the fold increase in the lag time for aggregation or as the decrease in the overall plateau level of aggregation (i.e., total amount of aggregation), using an aggregation assay as described in the Examples. In various embodiments, a modulator of the invention increases the lag time of aggregation at least 1.2-fold, 1.5-fold, 1.8-fold, 2-fold, 2.5-fold, 3-fold, 4-fold or 5-fold. In various other embodiments, a modulator of the invention inhibits the plateau level of aggregation at least 10%, 20%, 30%, 40%, 50%, 75% or 100%.

A modulator which inhibits β-AP aggregation (an "inhibitory modulator compound") can be used to prevent or delay the onset of β-amyloid deposition. Moreover, as demonstrated in Example 10, inhibitory modulator compounds of the invention inhibit the formation and/or activity of neurotoxic aggregates of natural Aβ peptide (i.e., the inhibitory compounds can be used to inhibit the neurotoxicity of β-AP). Still further, also as demonstrated in Example 10, the inhibitory compounds of the invention can be used to reduce the neurotoxicity of preformed β-AP aggregates, indicating that the inhibitory modulators can either bind to preformed Aβ fibrils or soluble aggregate and modulate their inherent neurotoxicity or that the modulators can perturb the equilibrium between monomeric and aggregated forms of β-AP in favor of the non-neurotoxic form.

Alternatively, in another embodiment, a modulator compound of the invention promotes the aggregation of natural Aβ peptides. The various forms of the term "promotion" refer to an increase in the amount and/or rate of β-AP aggregation in the presence of the modulator, as compared to the amount and/or rate of β-AP aggregation in the absence of the modulator. Such a compound which promotes Aβ aggregation is referred to as a stimulatory modulator compound. Stimulatory modulator compounds may be useful for sequestering β-amyloid peptides, for example in a biological compartment where aggregation of β-AP may not be deleterious to thereby deplete β-AP from a biological compartment where aggregation of β-AP is deleterious. Moreover, stimulatory modulator compounds can be used to promote Aβ aggregation in in vitro aggregation assays (e.g., assays such as those described in the Examples), for example in screening assays for test compounds that can then inhibit or reverse this Aβ aggregation (i.e., a stimulatory modulator compound can act as a "seed" to promote the formation of Aβ aggregates).

In a preferred embodiment, the modulators of the invention are capable of altering β-AP aggregation when contacted with a molar excess amount of natural β-AP. A "molar excess amount of natural β-AP" refers to a concentration of natural β-AP, in moles, that is greater than the concentration, in moles, of the modulator. For example, if the modulator and β-AP are both present at a concentration of 1 μM, they are said to be "equimolar", whereas if the modulator is present at a concentration of 1 μM and the β-AP is present at a concentration of 5 μM, the β-AP is said to be present at a 5-fold molar excess amount compared to the modulator. In preferred embodiments, a modulator of the invention is effective at altering natural β-AP aggregation when the natural β-AP is present at at least a 2-fold, 3-fold or 5-fold molar excess compared to the concentration of the modulator. In other embodiments, the modulator is effective at altering β-AP aggregation when the natural β-AP is present at at least a 10-fold, 20-fold, 33-fold, 50-fold, 100-fold, 500-fold or 1000-fold molar excess compared to the concentration of the modulator.

Various additional aspects of the modulators of the invention, and the uses thereof, are described in further detail in the following subsections.

I. Modulator Compounds

In one embodiment, a modulator of the invention comprises a β-amyloid peptide compound comprising the formula:

wherein Xaa is a β-amyloid peptide, A is a modulating group attached directly or indirectly to the β-amyloid peptide of the compound such that the compound inhibits aggregation of natural β-amyloid peptides when contacted with the natural β-amyloid peptides, and n is an integer selected such that the compound inhibits aggregation of natural β-amyloid peptides when contacted with the natural β-amyloid peptides.

Preferably, β-amyloid peptide of the compound has an amino-terminal amino acid residue corresponding to position 668 of β-amyloid precursor protein-770 (APP-770) or to a residue carboxy-terminal to position 668 of APP-770. The amino acid sequence of APP-770 from position 668 to position 770 (i.e., the carboxy terminus) is shown below and in SEQ ID NO: 2:

EVKMDAEFRHDSGYEVHHQKLVFFAED-
VGSNKGAIIGLMVGGVVIATVIVITL
VMLKKKQYTSIHHGVVEVDAAVT-
PEERHLSKMQQNGYENPTYKFFEQMQN.

More preferably, the amino-terminal amino acid residue of the β-amyloid peptide corresponds to position 672 of APP-770 (position 5 of the amino acid sequence of SEQ ID NO: 2) or to a residue carboxy-terminal to position 672 of APP-770. Although the β-amyloid peptide of the compound may encompass the 103 amino acid residues corresponding to positions 668–770 of APP-770, preferably the peptide is between 6 and 60 amino acids in length, more preferably between 10 and 43 amino acids in length and even more preferably between 10 and 25 amino acid residues in length.

As used herein, the term "β amyloid peptide", as used in a modulator of the invention is intended to encompass peptides having an amino acid sequence identical to that of the natural sequence in APP, as well as peptides having acceptable amino acid substitutions from the natural sequence. Acceptable amino acid substitutions are those that do not affect the ability of the peptide to alter natural β-AP aggregation. Moreover, particular amino acid substitutions may further contribute to the ability of the peptide to alter natural β-AP aggregation and/or may confer additional beneficial properties on the peptide (e.g. increased solubility, reduced association with other amyloid proteins, etc.). For example, substitution of hydrophobic amino acid residues for the two phenylalanine residues at positions 19 and 20 of natural β-AP (positions 19 and 20 of the amino acid sequence shown in SEQ ID NO: 1) may further contribute to the ability of the peptide to alter β-AP aggregation (see Hilbich, C. (1992) *J. Mol. Biol.* 228:460–473). Thus, in one embodiment, the β-AP of the compound consists of the amino acid sequence shown below and in SEQ ID NO: 3:

DAEFRHDSGYEVHHQKLV(Xaa$_{19}$)(Xaa$_{20}$)
AEDVGSNKGAIIGLMVGGVVIAT (or an amino-terminal or carboxy-terminal deletion thereof), wherein Xaa is a hydrophobic amino acid. Examples of hydrophobic amino acids are isoleucine, leucine, threonine, serine, alanine, valine or glycine. Preferably, $F_{19}F_{20}$ is substituted with $T_{19}T_{20}$ or $G_{19}I_{20}$.

Other suitable amino acid substitutions include replacement of amino acids in the human peptide with the corresponding amino acids of the rodent β-AP peptide. The three amino acid residues that differ between human and rat β-AP are at positions 5, 10 and 13 of the amino acid sequence shown in SEQ ID NOs: 1 and 3. A human β-AP having the human to rodent substitutions Arg$_5$ to Gly, Tyr$_{10}$ to Phe and His$_{13}$ to Arg has been shown to retain the properties of the human peptide (see Fraser, P. E. et al. (1992) *Biochemistry* 31:10716–10723; and Hilbich, C. et al. (1991) *Eur. J. Biochem.* 201:61–69). Accordingly, a human β-AP having rodent β-AP a.a. substitutions is suitable for use in a modulator of the invention.

Other possible β-AP amino acid substitutions are described in Hilbich, C. et al. (1991) *J. Mol. Biol.* 218:149–163; and Hilbich, C. (1992) *J. Mol. Biol.* 228:460–473. Moreover, amino acid substitutions that affect the ability of β-AP to associate with other proteins can be introduced. For example, one or more amino acid substitutions that reduce the ability of β-AP to associate with the serpin enzyme complex (SEC) receptor, α1-antichymotrypsin (ACT) and/or apolipoprotein E (ApoE) can be introduced. A preferred substitution for reducing binding to the SEC receptor is $L_{34}M_{35}$ to $A_{34}A_{35}$ (at positions 34 and 35 of the amino acid sequences shown in SEQ ID NOs: 1 and 3). A preferred substitution for reducing binding to ACT is $S_8$ to $A_8$ (at position 8 of the amino acid sequences shown in SEQ ID NOs: 1 and 3).

Alternative to β-AP amino acid substitutions described herein or known in the art, a modulator composed, at least in part, of an amino acid-substituted β amyloid peptide can be prepared by standard techniques and tested for the ability to alter β-AP aggregation using an aggregation assay described herein. To retain the properties of the original modulator, preferably conservative amino acid substitutions are made at one or more amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), β-branched side chains (e.g., threonine, valine, isoleucine) and aromatic side chains (e.g., tyrosine, phenylalanine, tryptophan, histidine). Accordingly, a modulator composed of a β amyloid peptide having an amino acid sequence that is mutated from that of the wild-type sequence in APP-770 yet which still retains the ability to alter natural β-AP aggregation is within the scope of the invention.

As used herein, the term "β amyloid peptide" is further intended to include peptide analogues or peptide derivatives or peptidomimetics that retain the ability to alter natural β-AP aggregation as described herein. For example, a β amyloid peptide of a modulator of the invention may be modified to increase its stability, bioavailability, solubility, etc. The terms "peptide analogue", "peptide derivative" and "peptidomimetic" as used herein are intended to include molecules which mimic the chemical structure of a peptide and retain the functional properties of the peptide. Approaches to designing peptide analogs are known in the art. For example, see Farmer, P. S. in *Drug Design* (E. J. Ariens, ed.) Academic Press, New York, 1980, vol. 10, pp. 119–143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270. Examples of peptide analogues, derivatives and peptidomimetics include peptides substituted with one or more benzodiazepine molecules (see e.g., James, G. L. et al. (1993) *Science* 260:1937–1942), peptides with methylated amide linkages and "retro-inverso" peptides (see U.S. Pat. No. 4,522,752 by Sisto). Peptide analogues, peptide derivatives and peptidomimetic are described in further detail below with regard to compounds comprising an Aβ aggregation core domain.

In a modulator of the invention having the formula shown above, a modulating group ("A") is attached directly or indirectly to the β-amyloid peptide of the modulator (As used herein, the term "modulating group" and "modifying group" are used interchangeably to describe a chemical group directly or indirectly attached to an Aβ derived peptidic structure). For example, the modulating group can be directly attached by covalent coupling to the β-amyloid peptide or the modulating group can be attached indirectly by a stable non-covalent association. In one embodiment of the invention, the modulating group is attached to the amino-terminus of the β-amyloid peptide of the modulator. Accordingly, the modulator can comprise a compound having a formula:

$$A-\overset{H}{\underset{}{N}}-(Xaa).$$

Alternatively, in another embodiment of the invention, the modulating group is attached to the carboxy-terminus of the β-amyloid peptide of the modulator. Accordingly, the modulator can comprise a compound having a formula:

$$(Xaa)-\overset{O}{\underset{}{C}}-A.$$

In yet another embodiment, the modulating group is attached to the side chain of at least one amino acid residue of the β-amyloid peptide of the compound (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain).

The modulating group is selected such that the compound inhibits aggregation of natural β-amyloid peptides when contacted with the natural β-amyloid peptides. Accordingly, since the β-AP peptide of the compound is modified from its natural state, the modulating group "A" as used herein is not intended to include hydrogen. In a preferred embodiment, the modulating group is a biotin compound of the formula:

[structure with W, $X_1$, $X_2$, $X_3$, $R_1$, C=O, Y]

wherein $X_1$–$X_3$ are each independently selected from the group consisting of S, O and $NR_2$, wherein $R_2$ is hydrogen, or an aryl, lower alkyl, alkenyl or alkynyl moiety; W is =O or $N(R_2)_2$; $R_1$ is a lower alkylenyl moiety and Y is a direct bond or a spacer molecule selected for its ability to react with a target group on a β-AP. At least one of $X_1$–$X_3$ is an $NR_2$ group or W is an $N(R_2)_2$ group.

The term "aryl" is intended to include aromatic moieties containing substituted or unsubstituted ring(s), e.g., benzyl, naphthyl, etc. Other more complex fused ring moieties also are intended to be included.

The term "lower alkyl or alkylenyl moiety" refers to a saturated, straight or branched chain (or combination thereof) hydrocarbon containing 1 to about 6 carbon atoms, more preferably from 1 to 3 carbon atoms. The terms "lower alkenyl moiety" and "lower alkynyl moiety" refer to unsaturated hydrocarbons containing 1 to about 6 carbon atoms, more preferably 1 to 3 carbon atoms. Preferably, $R_2$ contains 1 to 3 carbon atoms. Preferably, $R_1$ contains 4 carbon atoms.

The spacer molecule (Y) can be, for example, a lower alkyl group or a linker peptide, and is preferably selected for its ability to link with a free amino group (e.g., the α-amino group at the amino-terminus of a β-AP). Thus, in a preferred embodiment, the biotin compound modifies the amino-terminus of a β-amyloid peptide.

Additional suitable modulating groups may include other cyclic and heterocyclic compounds and other compounds having similar steric "bulk". Non-limiting examples of compounds which can be used to modify a β-AP are shown schematically in FIG. 2, and include N-acetylneuraminic acid, cholic acid, trans-4-cotininecarboxylic acid, 2-imino-1-imidazolidineacetic acid, (S)-(−)-indoline-2-carboxylic acid, (−)-menthoxyacetic acid, 2-norbornaneacetic acid, γ-oxo-5-acenaphthenebutyric acid, (−)-2-oxo-4-thiazolidinecarboxylic acid, tetrahydro-3-furoic acid, 2-iminobiotin-N-hydroxysuccinimide ester, diethylenetri-aminepentaacetic dianhydride, 4-morpholinecarbonyl chloride, 2-thiopheneacetyl chloride, 2-thiophenesulfonyl chloride, 5-(and 6-)-carboxyfluorescein (succinimidyl ester), fluorescein isothiocyanate, and acetic acid (or derivatives thereof). Suitable modulating groups are described further in subsection II below.

In a modulator of the invention, a single modulating group may be attached to a β-amyloid peptide (e.g., n=1 in the formula shown above) or multiple modulating groups may be attached to the peptide. The number of modulating groups is selected such that the compound inhibits aggregation of natural β-amyloid peptides when contacted with the natural β-amyloid peptides. However, n preferably is an integer between 1 and 60, more preferably between 1 and 30 and even more preferably between 1 and 10 or 1 and 5.

In another embodiment, a β-amyloid modulator compound of the invention comprises an Aβ aggregation core domain (abbreviated as ACD) coupled directly or indirectly to a modifying group such that the compound modulates the aggregation or inhibits the neurotoxicity of natural β-amyloid peptides when contacted with the natural β-amyloid peptides. As used herein, an "Aβ aggregation core domain" is intended to refer to a structure that is modeled after a subregion of a natural β-amyloid peptide which is sufficient to modulate aggregation of natural β-APs when this subregion of the natural β-AP is appropriately modified as described herein (e.g., modified at the amino-terminus). The term "subregion of a natural β-amyloid peptide" is intended to include amino-terminal and/or carboxy-terminal deletions of natural β-AP. The term "subregion of natural β-AP" is not intended to include full-length natural β-AP (i.e., "subregion" does not include $A\beta_{1-39}$, $A\beta_{1-40}$, $A\beta_{1-41}$, $A\beta_{1-42}$ and $A\beta_{1-43}$).

Although not intending to be limited by mechanism, the ACD of the modulators of the invention is thought to confer a specific targeting function on the compound that allows the compound to recognize and specifically interact with natural β-AP. Preferably, the ACD is modeled after a subregion of natural β-AP that is less than 15 amino acids in length and more preferably is between 3–10 amino acids in length. In various embodiments, the ACD is modeled after a subregion of β-AP that is 10, 9, 8, 7, 6, 5, 4 or 3 amino acids in length. In one embodiment, the subregion of β-AP upon which the ACD is modeled is an internal or carboxy-terminal region of β-AP (i.e., downstream of the amino-terminus at amino acid position 1). In another embodiment, the ACD is modeled after a subregion of β-AP that is hydrophobic. In certain specific embodiments, the term Aβ aggregation core domain specifically excludes β-AP subregions corresponding to amino acid positions 1–15 ($A\beta_{1-15}$), 6–20 ($A\beta_{6-20}$) and 16–40 ($A\beta_{16-40}$).

An Aβ aggregation core domain can be comprised of amino acid residues linked by peptide bonds. That is, the ACD can be a peptide corresponding to a subregion of β-AP. Alternatively, an Aβ aggregation core domain can be modeled after the natural Aβ peptide region but may be comprised of a peptide analogue, peptide derivative or peptidomimetic compound, or other similar compounds which mimics the structure and function of the natural peptide. Accordingly, as used herein, an "Aβ aggregation core domain" is intended to include peptides, peptide analogues, peptide derivatives and peptidomimetic compounds which, when appropriately modified, retain the aggregation modulatory activity of the modified natural Aβ peptide subregion. Such structures that are designed based upon the amino acid sequence are referred to herein as "Aβ derived peptidic structures." Approaches to designing peptide analogues, derivatives and mimetics are known in the art. For example, see Farmer, P. S. in *Drug Design* (E. J. Ariens, ed.) Academic Press, New York, 1980, vol. 10, pp. 119–143; Ball. J. B. and Alewood, P. F. (1990) *J. Mol. Recognition* 3:55; Morgan, B. A. and Gainor, J. A. (1989) *Ann. Rep. Med. Chem.* 24:243; and Freidinger, R. M. (1989) *Trends Pharmacol. Sci.* 10:270. See also Sawyer, T. K. (1995) "Peptidomimetic Design and Chemical Approaches to Peptide Metabolism" in Taylor, M. D. and Amidon, G. L. (eds.) *Peptide-Based Drug Design: Controlling Transport and Metabolism*, Chapter 17; Smith, A. B. 3rd, et al. (1995) *J. Am. Chem. Soc.* 117:11113–11123; Smith, A. B. 3rd, et al. (1994) *J. Am. Chem. Soc.* 116:9947–9962; and Hirschman, R., et al. (1993) *J. Am. Chem. Soc.* 115:12550–12568.

As used herein, a "derivative" of a compound X (e.g., a peptide or amino acid) refers to a form of X in which one or more reaction groups on the compound have been derivatized with a substituent group. Examples of peptide derivatives include peptides in which an amino acid side chain, the peptide backbone, or the amino- or carboxy-terminus has been derivatized (e.g., peptidic compounds with methylated amide linkages). As used herein an "analogue" of a compound X refers to a compound which retains chemical structures of X necessary for functional activity of X yet which also contains certain chemical structures which differ from X. An examples of an analogue of a naturally-occurring peptide is a peptides which includes one or more non-naturally-occurring amino acids. As used herein, a "mimetic" of a compound X refers to a compound in which chemical structures of X necessary for functional activity of X have been replaced with other chemical structures which mimic the conformation of X. Examples of peptidomimetics include peptidic compounds in which the peptide backbone is substituted with one or more benzodiazepine molecules (see e.g., James, G. L. et al. (1993) *Science* 260:1937–1942), peptides in which all L-amino acids are substituted with the corresponding D-amino acids and "retro-inverso" peptides (see U.S. Pat. No. 4,522,752 by Sisto), described further below.

The term mimetic, and in particular, peptidomimetic, is intended to include isosteres. The term "isostere" as used herein is intended to include a chemical structure that can be substituted for a second chemical structure because the steric conformation of the first structure fits a binding site specific for the second structure. The term specifically includes peptide back-bone modifications (i.e., amide bond mimetics) well known to those skilled in the art. Such modifications include modifications of the amide nitrogen, the α-carbon, amide carbonyl, complete replacement of the amide bond, extensions, deletions or backbone crosslinks. Several peptide backbone modifications are known, including ψ[CH$_2$S], ψ[CH$_2$NH], ψ[CSNH$_2$], ψ[NHCO], ψ[COCH$_2$], and ψ[(E) or (Z) CH=CH]. In the nomenclature used above, ψ indicates the absence of an amide bond. The structure that replaces the amide group is specified within the brackets. Other examples of isosteres include peptides substituted with one or more benzodiazepine molecules (see e.g., James, G. L. et al. (1993) *Science* 260:1937–1942).

Other possible modifications include an N-alkyl (or aryl) substitution (ψ[CONR]), backbone crosslinking to construct lactams and other cyclic structures, substitution of all D-amino acids for all L-amino acids within the compound ("inverso" compounds) or retro-inverso amino acid incorporation (ψ[NHCO]). By "inverso" is meant replacing L-amino acids of a sequence with D-amino acids, and by "retro-inverso" or "enantio-retro" is meant reversing the sequence of the amino acids ("retro") and replacing the L-amino acids with D-amino acids. For example, if the parent peptide is Thr-Ala-Tyr, the retro modified form is Tyr-Ala-Thr, the inverso form is thr-ala-tyr, and the retro-inverso form is tyr-ala-thr (lower case letters refer to D-amino acids). Compared to the parent peptide, a retro-inverso peptide has a reversed backbone while retaining substantially the original spatial conformation of the side chains, resulting in a retro-inverso isomer with a topology that closely resembles the parent peptide. See Goodman et al. *"Perspectives in Peptide Chemistry"* pp. 283–294 (1981). See also U.S. Pat. No. 4,522,752 by Sisto for further description of "retro-inverso" peptides.

Other derivatives of the modulator compounds of the invention include C-terminal hydroxymethyl derivatives, O-modified derivatives (e.g., C-terminal hydroxymethyl benzyl ether), N-terminally modified derivatives including substituted amides such as alkylamides and hydrazides and compounds in which a C-terminal phenylalanine residue is replaced with a phenethylamide analogue (e.g., Val-Phe-phenethylamide as an analogue of the tripeptide Val-Phe-Phe).

In a preferred embodiment, the ACD of the modulator is modeled after the subregion of β-AP encompassing amino acid positions 17–20 (i.e., Leu-Val-Phe-Phe; SEQ ID NO: 12). As described further in Examples 7, 8 and 9, peptide subregions of $Aβ_{1-40}$ were prepared, amino-terminally modified and evaluated for their ability to modulate aggregation of natural β-amyloid peptides. One subregion that was effective at inhibiting aggregation was $Aβ_{6-20}$ (i.e., amino acid residues 6–20 of the natural $Aβ_{1-40}$ peptide, the amino acid sequence of which is shown in SEQ ID NO: 4). Amino acid residues were serially deleted from the amino-terminus or carboxy terminus of this subregion to further delineate a minimal subregion that was sufficient for aggregation inhibitory activity. This process defined $Aβ_{17-20}$ (ie., amino acid residues 17–20 of the natural $Aβ_{1-40}$ peptide) as a minimal subregion that, when appropriately modified, is sufficient for aggregation inhibitory activity. Accordingly, an "Aβ aggregation core domain" within a modulator compound of the invention can be modeled after $Aβ_{17-20}$ In one embodiment, the Aβ aggregation core domain comprises $Aβ_{17-20}$ itself (i.e., a peptide comprising the amino acid sequence leucine-valine-phenylalanine-phenylalanine; SEQ ID NO: 12). In other embodiments, the structure of $Aβ_{17-20}$ is used as a model to design an Aβ aggregation core domain having similar structure and function to $Aβ_{17-20}$. For example, peptidomimetics, derivatives or analogues of $Aβ_{17-20}$ (as described above) can be used as an Aβ aggregation core domain. In addition to $Aβ_{17-20}$, the natural Aβ peptide is likely to contain other minimal subregions that are sufficient for aggregation inhibitory activity. Such additional minimal subregions can be identified by the processes described in Examples 7, 8 and 9, wherein a 15 mer subregion of $Aβ_{1-40}$ is serially deleted from the amino-terminus or carboxy terminus, the deleted peptides are appropriately modified and then evaluated for aggregation inhibitory activity.

One form of the β-amyloid modulator compound comprising an Aβ aggregation core domain modeled after $Aβ_{17-20}$ coupled directly or indirectly to at least one modifying group has the formula:

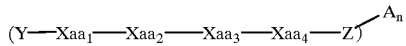

wherein $Xaa_1$ and $Xaa_3$ are amino acid structures;
$Xaa_2$ is a valine structure;
$Xaa_4$ is a phenylalanine structure;
Y, which may or may not be present, is a peptidic structure having the formula $(Xaa)_a$, wherein Xaa is any amino acid structure and a is an integer from 1 to 15;
Z, which may or may not be present, is a peptidic structure having the formula $(Xaa)_b$, wherein Xaa is any amino acid structure and b is an integer from 1 to 15; and
A is a modifying group attached directly or indirectly to the compound and n is an integer;
$Xaa_1$, $Xaa_3$, Y, Z, A and n being selected such that the compound modulates the aggregation or inhibits the neurotoxicity of natural β-amyloid peptides when contacted with the natural β-amyloid peptides.

Preferably, a modulator compound of the above formula inhibits aggregation of natural β-amyloid peptides when contacted with the natural β-amyloid peptides and/or inhibits Aβ neurotoxicity. Alternatively, the modulator compound can promote aggregation of natural β-amyloid peptides when contacted with the natural β-amyloid peptides. The type and number of modifying groups ("A") coupled to the modulator are selected such that the compound alters (and preferably inhibits) aggregation of natural β-amyloid peptides when contacted with the natural β-amyloid peptides. A single modifying group can be coupled to the modulator (i.e., n=1 in the above formula) or, alternatively, multiple modifying groups can be coupled to the modulator. In various embodiments, n is an integer between 1 and 60, between 1 and 30, between 1 and 10, between 1 and 5 or between 1 and 3. Suitable types of modifying groups are described further in subsection II below.

As demonstrated in Example 9, amino acid positions 18 ($Val_{18}$) and 20 ($Phe_{20}$) of $Aβ_{17-20}$ (corresponding to $Xaa_2$ and $Xaa_4$) are particularly important within the core domain for inhibitory activity of the modulator compound. Accordingly, these positions are conserved within the core domain in the formula shown above. The terms "valine structure" and "phenylalanine structure" as used in the above formula are intended to include the natural amino acids, as well as non-naturally-occurring analogues, derivatives and mimetics of valine and phenylalanine, respectively, (including D-amino acids) which maintain the functional activity of the compound. Moreover, although $Val_{18}$ and $Phe_{20}$ have an important functional role, it is possible that $Xaa_2$ and/or $Xaa_4$ can be substituted with other naturally-occurring amino acids that are structurally related to valine or phenylalanine, respectively, while still maintaining the activity of the compound. Thus, the terms "valine structure" is intended to include conservative amino acid substitutions that retain the activity of valine at $Xaa_2$, and the term "phenylalanine structure" is intended to include conservative amino acid substitutions that retain the activity of phenylalanine at $Xaa_4$. However, the term "valine structure" is not intended to include threonine.

In contrast to positions 18 and 20 of $A\beta_{17-20}$, a Phe to Ala substitution at position 19 (corresponding to $Xaa_3$) did not abolish the activity of the modulator, indicating position 19 may be more amenable to amino acid substitution. In various embodiments of the above formula, positions $Xaa_1$ and $Xaa_3$ are any amino acid structure. The term "amino acid structure" is intended to include natural and non-natural amino acids as well as analogues, derivatives and mimetics thereof, including D-amino acids. In a preferred embodiment of the above formula, $Xaa_1$ is a leucine structure and $Xaa_3$ is a phenylalanine structure (i.e., modeled after $Leu_{17}$ and $Phe_{19}$, respectively, in the natural $A\beta$ peptide sequence). The term "leucine structure" is used in the same manner as valine structure and phenylalanine structure described above. Alternatively, an another embodiment, $Xaa_3$ is an alanine structure.

The four amino acid structure ACD of the modulator of the above formula can be flanked at the amino-terminal side, carboxy-terminal side, or both, by peptidic structures derived either from the natural $A\beta$ peptide sequence or from non-$A\beta$ sequences. The term "peptidic structure" is intended to include peptide analogues, derivatives and mimetics thereof, as described above. The peptidic structure is composed of one or more linked amino acid structures, the type and number of which in the above formula are variable. For example, in one embodiment, no additional amino acid structures flank the $Xaa_1$-$Xaa_2$-$Xaa_3$-$Xaa_4$ core sequence (i.e., Y and Z are absent in the above formula). In another embodiment, one or more additional amino acid structures flank only the amino-terminus of the core sequences (i.e., Y is present but Z is absent in the above formula). In yet another embodiment, one or more additional amino acid structures flank only the carboxy-terminus of the core sequences (i.e., Z is present but Y is absent in the above formula). The length of flanking Z or Y sequences also is variable. For example, in one embodiment, a and b are integers from 1 to 15. More preferably, a and b are integers between 1 and 10. Even more preferably, a and b are integers between 1 and 5. Most preferably, a and b are integers between 1 and 3.

One form of the β-amyloid modulator compound comprising an Aβ aggregation core domain modeled after $A\beta_{17-20}$ coupled directly or indirectly to at least one modifying group has the formula:

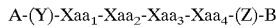

wherein $Xaa_1$ and $Xaa_3$ are amino acids or amino acid mimetics;

$Xaa_2$ is valine or a valine mimetic $Xaa_4$ is phenylalanine or a phenylalanine mimetic;

Y, which may or may not be present, is a peptide or peptidomimetic having the formula $(Xaa)_a$, wherein Xaa is any amino acid or amino acid mimetic and a is an integer from 1 to 15;

Z, which may or may not be present, is a peptide or peptidomimetic having the formula $(Xaa)_b$, wherein Xaa is any amino acid or amino acid mimetic and b is an integer from 1 to 15; and A and B, at least one of which is present, are modifying groups attached directly or indirectly to the amino terminus and carboxy terminus, respectively, of the compound;

$Xaa_1$, $Xaa_3$, Y, Z, A and B being selected such that the compound modulates the aggregation or inhibits the neurotoxicity of natural β-amyloid peptides when contacted with the natural β-amyloid peptides.

In this embodiment, the modulator compound is specifically modified at either its amino-terminus, its carboxy-terminus, or both. The terminology used in this formula is the same as described above. Suitable modifying groups are described in subsection II below. In one embodiment, the compound is modified only at its amino terminus (i.e., B is absent and the compound comprises the formula: A-(Y)-$Xaa_1$-$Xaa_2$-$Xaa_3$-$Xaa_4$-(Z)). In another embodiment, the compound is modified only at its carboxy-terminus (i.e., A is absent and the compound comprises the formula: (Y)-$Xaa_1$-$Xaa_2$-$Xaa_3$-$Xaa_4$-(Z)-B). In yet another embodiment, the compound is modified at both its amino- and carboxy termini (i.e., the compound comprises the formula: A-(Y)-$Xaa_1$-$Xaa_2$-$Xaa_3$-$Xaa_4$-(Z)-B and both A and B are present). As described above, the type and number of amino acid structures which flank the $Xaa_1$-$Xaa_2$-$Xaa_3$-$Xaa_4$ core sequences in the above formula is variable. For example, in one embodiment, a and b are integers from 1 to 15. More preferably, a and b are integers between 1 and 10. Even more preferably, a and b are integers between 1 and 5. Most preferably, a and b are integers between 1 and 3.

As demonstrated in Examples 7, 8 and 9, preferred AP modulator compounds of the invention comprise modified forms of $A\beta_{14-21}$ (His-Gln-Lys-Leu-Val-Phe-Phe-Ala; SEQ ID NO: 5), or amino-terminal or carboxy-terminal deletions thereof, with a preferred "minimal core region" comprising $A\beta_{17-20}$. Accordingly, in specific embodiments, the invention provides compounds comprising the formula:

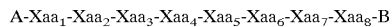

wherein Xaa1 is a histidine structure;

Xaa2 is a glutamine structure;

Xaa3 is a lysine structure;

Xaa4 is a leucine structure;

Xaa5 is a valine structure;

Xaa6 is a phenylalanine structure;

Xaa7 is a phenylalanine structure;

Xaa8 is an alanine structure;

A and B are modifying groups attached directly or indirectly to the amino terminus and carboxy terminus, respectively, of the compound;

and wherein $Xaa_1$-$Xaa_2$-$Xaa_3$, $Xaa_1$-$Xaa_2$ or $Xaa_1$ may or may not be present;

$Xaa_8$ may or may not be present; and at least one of A and B is present.

In one specific embodiment, the compound comprises the formula: A-$Xaa_4$-$Xaa_5$-$Xaa_6$-$Xaa_7$-B (e.g, a modified form of $A\beta_{17-20}$, comprising an amino acid sequence Leu-Val-Phe-Phe; SEQ ID NO: 12).

In another specific embodiment, the compound comprises the formula: A-$Xaa_4$-$Xaa_5$-$Xaa_6$-$Xaa_7$-$Xaa_8$-B (e.g, a modified form of $A\beta_{17-21}$, comprising an amino acid sequence Leu-Val-Phe-Phe-Ala; SEQ ID NO: 11).

In another specific embodiment, the compound comprises the formula: A-$Xaa_3$-$Xaa_4$-$Xaa_5$-$Xaa_6$-$Xaa_7$-B (e.g., a modified form of $A\beta_{16-20}$, comprising an amino acid sequence Lys-Leu-Val-Phe-Phe; SEQ ID NO: 10).

In another specific embodiment, the compound comprises the formula: A-$Xaa_3$-$Xaa_4$-$Xaa_5$-$Xaa_6$-$Xaa_7$-$Xaa_8$-B (e.g., a modified form of $A\beta_{16-21}$, comprising an amino acid sequence Lys-Leu-Val-Phe-Phe-Ala; SEQ ID NO: 9).

In another specific embodiment, the compound comprises the formula: A-$Xaa_2$-$Xaa_3$-$Xaa_4$-$Xaa_5$-$Xaa_6$-$Xaa_7$-B (e.g., a modified form of $A\beta_{15-20}$, comprising an amino acid sequence Gln-Lys-Leu-Val-Phe-Phe; SEQ ID NO: 8).

In another specific embodiment, the compound comprises the formula: A-Xaa$_1$-Xaa$_3$-Xaa$_4$-Xaa$_5$-Xaa$_6$-Xaa$_7$-Xaa$_8$-B (e.g., a modified form of Aβ$_{15-21}$, comprising an amino acid sequence Gln-Lys-Leu-Val-Phe-Phe-Ala; SEQ ID NO: 7).

In another specific embodiment, the compound comprises the formula: A-Xaa$_1$-Xaa$_2$-Xaa$_3$-Xaa$_4$-Xaa$_5$-Xaa$_6$-Xaa$_7$-B (e.g., a modified form of Aβ$_{14-20}$, comprising an amino acid sequence His-Gln-Lys-Leu-Val-Phe-Phe; SEQ ID NO: 6).

In another specific embodiment, the compound comprises the formula: A-Xaa$_1$-Xaa$_2$-Xaa$_3$-Xaa$_4$-Xaa$_5$-Xaa$_6$-Xaa$_7$-Xaa$_8$-B (e.g., a modified form of Aβ$_{14-21}$, comprising an amino acid sequence His-Gln-Lys-Leu-Val-Phe-Phe-Ala; SEQ ID NO: 5).

In preferred embodiments of the aforementioned specific embodiments, A or B is a cholanoyl structure or a biotin-containing structure (described further in subsection II below).

In further experiments to delineate subregions of Aβ upon which an Aβ aggregation core domain can be modeled (the results of which are described in Example 11), it was demonstrated that a modulator compound having inhibitory activity can comprise as few as three AP amino acids residues (e.g., Val-Phe-Phe, which corresponds to Aβ$_{18-20}$ or Phe-Phe-Ala, which corresponds to Aβ$_{19-21}$). The results also demonstrated that a modulator compound having a modulating group at its carboxy-terminus is effective at inhibiting Aβ aggregation. Still further, the results demonstrated that the cholyl group, as a modulating group, can be manipulated while maintaining the inhibitory activity of the compounds and that an iodotyrosyl can be substituted for phenylalanine (e.g., at position 19 or 20 of the Aβ sequence) while maintaining the ability of the compound to inhibit Aβ aggregation.

Still further, the results demonstrated that compounds with inhibitory activity can be created using amino acids residues that are derived from the Aβ sequence in the region of about positions 17–21 but wherein the amino acid sequence is rearranged or has a substitution with a non-Aβ-derived amino acid. Examples of such compounds include PPI-426, in which the sequence of Aβ$_{17-21}$ (LVFFA; SEQ ID NO: 11) has been rearranged (FFVLA; SEQ ID NO: 21), PPI-372, in which the sequence of Aβ$_{16-20}$ (KLVFF; SEQ ID NO: 10) has been rearranged (FKFVL; SEQ ID NO: 29), and PPI-388, -389 and -390, in which the sequence of Aβ$_{17-21}$ (LVFFA; SEQ ID NO: 11) has been substituted at position 17, 18 or 19, respectively, with an alanine residue (AVFFA (SEQ ID NO: 25) for PPI-388, LAFFA (SEQ ID NO: 13) for PPI-389 and LVAFA (SEQ ID NO: 32) for PPI-390). The inhibitory activity of these compounds indicate that the presence in the compound of an amino acid sequence directly corresponding to a portion of Aβ is not essential for inhibitory activity, but rather suggests that maintenance of the hydrophobic nature of this core region, by inclusion of amino acid residues such as phenylalanine, valine, leucine, regardless of their precise order, can be sufficient for inhibition of Aβ aggregation. Accordingly, an Aβ aggregation core domain can be designed based on the direct Aβ amino acid sequence or can be designed based on a rearranged Aβ sequence which maintains the hydrophobicity of the Aβ subregion, e.g., the region around positions 17–20. This region of Aβ contains the amino acid residues Leu, Val and Phe. Accordingly, preferred Aβ aggregation core domains are composed of at least three amino acid structures (as that term is defined hereinbefore, including amino acid derivatives, analogues and mimetics), wherein at least two of the amino acid structures are, independently, either a leucine structure, a valine structure or a phenylalanine structure (as those terms are defined hereinbefore, including derivatives, analogues and mimetics).

Thus, in another embodiment, the invention provides a β-amyloid modulator compound comprising a formula:

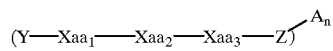

wherein Xaa$_1$, Xaa$_2$ and Xaa$_3$ are each amino acid structures and at least two of Xaa$_1$, Xaa$_2$ and Xaa$_3$ are, independently, selected from the group consisting of a leucine structure, a phenylalanine structure and a valine structure;

Y, which may or may not be present, is a peptidic structure having the formula (Xaa)$_a$, wherein Xaa is any amino acid structure and a is an integer from 1 to 15;

Z, which may or may not be present, is a peptidic structure having the formula (Xaa)$_b$, wherein Xaa is any amino acid structure and b is an integer from 1 to 15; and A is a modifying group attached directly or indirectly to the compound and n is an integer;

Xaa$_1$, Xaa$_2$, Xaa$_3$, Y, Z, A and n being selected such that the compound modulates the aggregation or inhibits the neurotoxicity of natural β-amyloid peptides when contacted with the natural β-amyloid peptides.

Preferably, the compound inhibits aggregation of natural β-amyloid peptides when contacted with the natural β-amyloid peptides. In preferred embodiments, Xaa$_1$ and Xaa$_2$ are each phenylalanine structures or Xaa$_2$ and Xaa$_3$ are each phenylalanine structures. "n" can be, for example, an integer between 1 and 5, whereas "a" and "b" can be, for example, integers between 1 and 5. The modifying group "A" preferably comprises a cyclic, heterocyclic or polycyclic group. More preferably, A contains a cis-decalin group, such as cholanoyl structure or a cholyl group In other embodiments, A can comprise a biotin-containing group, a diethylene-triaminepentaacetyl group, a (−)-menthoxyacetyl group, a fluorescein-containing group or an N-acetylneuraminyl group. In yet other embodiments, the compound may promotes aggregation of natural β-amyloid peptides when contacted with the natural β-amyloid peptides, may be further modified to alter a pharmacokinetic property of the compound or may be further modified to label the compound with a detectable substance.

In another embodiment, the invention provides a β-amyloid modulator compound comprising a formula:

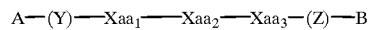

wherein Xaa$_1$, Xaa$_2$ and Xaa$_3$ are each amino acid structures and at least two of Xaa$_1$, Xaa$_2$ and Xaa$_3$ are, independently, selected from the group consisting of a leucine structure, a phenylalanine structure and a valine structure;

Y, which may or may not be present, is a peptidic structure having the formula (Xaa)$_a$, wherein Xaa is any amino acid structure and a is an integer from 1 to 15;

Z, which may or may not be present, is a peptidic structure having the formula (Xaa)$_b$, wherein Xaa is any amino acid structure and b is an integer from 1 to 15; and A and B, at least one of which is present, are modifying groups attached directly or indirectly to the amino terminus and carboxy terminus, respectively, of the compound;

Xaa$_1$, Xaa$_2$, Xaa$_3$, Y, Z, A and B being selected such that the compound modulates the aggregation or inhibits the neurotoxicity of natural β-amyloid peptides when contacted with the natural β-amyloid peptides.

Preferably, the compound inhibits aggregation of natural β-amyloid peptides when contacted with the natural β-amyloid peptides. In preferred embodiments, Xaa₁ and Xaa₂ are each phenylalanine structures or Xaa₂ and Xaa₃ are each phenylalanine structures. In one subembodiment, the compound comprises the formula:

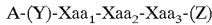

A-(Y)-Xaa₁-Xaa₂-Xaa₃-(Z)

In another subembodiment, the compound comprises the formula:

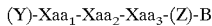

(Y)-Xaa₁-Xaa₂-Xaa₃-(Z)-B

"n" can be, for example, an integer between 1 and 5, whereas "a" and "b" can be, for example, integers between 1 and 5. The modifying group "A" preferably comprises a cyclic, heterocyclic or polycyclic group. More preferably, A contains a cis-decalin group, such as cholanoyl structure or a cholyl group. In other embodiments, A can comprise a biotin-containing group, a diethylene-triaminepentaacetyl group, a (−)-menthoxyacetyl group, a fluorescein-containing group or an N-acetylneuraminyl group. In yet other embodiments, the compound may promote aggregation of natural β-amyloid peptides when contacted with the natural -amyloid peptides, may be further modified to alter a pharmacokinetic property of the compound or may be further modified to label the compound with a detectable substance.

In preferred specific embodiments, the invention provides a β-amyloid modulator compound comprising a modifying group attached directly or indirectly to a peptidic structure, wherein the peptidic structure comprises amino acid structures having an amino acid sequence selected from the group consisting of His-Gln-Lys-Leu-Val-Phe-Phe-Ala (SEQ ID NO: 5), His-Gln-Lys-Leu-Val-Phe-Phe (SEQ ID NO: 6), Gln-Lys-Leu-Val-Phe-Phe-Ala (SEQ ID NO: 7), Gln-Lys-Leu-Val-Phe-Phe (SEQ ID NO: 8), Lys-Leu-Val-Phe-Phe-Ala (SEQ ID NO: 9), Lys-Leu-Val-Phe-Phe (SEQ ID NO: 10), Leu-Val-Phe-Phe-Ala (SEQ ID NO: 11), Leu-Val-Phe-Phe (SEQ ID NO: 12), Leu-Ala-Phe-Phe-Ala (SEQ ID NO: 13), Val-Phe-Phe (SEQ ID NO: 19), Phe-Phe-Ala (SEQ ID NO: 20), Phe-Phe-Val-Leu-Ala (SEQ ID NO: 21), Leu-Val-Phe-Phe-Lys (SEQ ID NO: 22), Leu-Val-Iodotyrosine-Phe-Ala (SEQ ID NO: 23), Val-Phe-Phe-Ala (SEQ ID NO: 24), Ala-Val-Phe-Phe-Ala (SEQ ID NO: 25), Leu-Val-Phe-Iodotyrosine-Ala (SEQ ID NO: 26), Leu-Val-Phe-Phe-Ala-Glu (SEQ ID NO: 27), Phe-Phe-Val-Leu (SEQ ID NO: 28), Phe-Lys-Phe-Val-Leu (SEQ ID NO: 29), Lys-Leu-Val-Ala-Phe (SEQ ID NO: 30), Lys-Leu-Val-Phe-Phe-βAla (SEQ ID NO: 31) and Leu-Val-Phe-Phe-DAla (SEQ ID NO: 32).

These specific compounds can be further modified to alter a pharmacokinetic property of the compound and/or further modified to label the compound with a detectable substance.

The modulator compounds of the invention can be incorporated into pharmaceutical compositions (described further in subsection V below) and can be used in detection and treatment methods as described further in subsection VI below.

II. Modifying Groups

Within a modulator compound of the invention, a peptidic structure (such as an Aβ derived peptide, or an Aβ aggregation core domain, or an amino acid sequence corresponding to a rearranged Aβ aggregation core domain) is coupled directly or indirectly to at least one modifying group (abbreviated as MG). In one embodiment, a modulator compounds of the invention comprising an aggregation core domain coupled to a modifying group, the compound can be illustrated schematically as MG-ACD. The term "modifying group" is intended to include structures that are directly attached to the peptidic structure (e.g., by covalent coupling), as well as those that are indirectly attached to the peptidic structure (e.g., by a stable non-covalent association or by covalent coupling to additional amino acid residues, or mimetics, analogues or derivatives thereof, which may flank the Aβ-derived peptidic structure). For example, the modifying group can be coupled to the amino-terminus or carboxy-terminus of an Aβ-derived peptidic structure, or to a peptidic or peptidomimetic region flanking the core domain. Alternatively, the modifying group can be coupled to a side chain of at least one amino acid residue of an Aβ-derived peptidic structure, or to a peptidic or peptidomimetic region flanking the core domain (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Modifying groups covalently coupled to the peptidic structure can be attached by means and using methods well known in the art for linking chemical structures, including, for example, amide, alkylamino, carbamate or urea bonds.

The term "modifying group" is intended to include groups that are not naturally coupled to natural Aβ peptides in their native form. Accordingly, the term "modifying group" is not intended to include hydrogen. The modifying group(s) is selected such that the modulator compound alters, and preferably inhibits, aggregation of natural β-amyloid peptides when contacted with the natural β-amyloid peptides or inhibits the neurotoxicity of natural β-amyloid peptides when contacted with the natural β-amyloid peptides. Although not intending to be limited by mechanism, the modifying group(s) of the modulator compounds of the invention is thought to function as a key pharmacophore which is important for conferring on the modulator the ability to disrupt Aβ polymerization.

In a preferred embodiment, the modifying group(s) comprises a cyclic, heterocyclic or polycyclic group. The term "cyclic group", as used herein, is intended to include cyclic saturated or unsaturated (i.e., aromatic) group having from about 3 to 10, preferably about 4 to 8, and more preferably about 5 to 7, carbon atoms. Exemplary cyclic groups include cyclopropyl, cyclobutyl, cyclopentyl, cyclohexyl, and cyclooctyl. Cyclic groups may be unsubstituted or substituted at one or more ring positions. Thus, a cyclic group may be substituted with, e.g., halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —CF₃, —CN, or the like.

The term "heterocyclic group" is intended to include cyclic saturated or unsaturated (i.e., aromatic) group having from about 3 to 10, preferably about 4 to 8, and more preferably about 5 to 7, carbon atoms, wherein the ring structure includes about one to four heteroatoms. Heterocyclic groups include pyrrolidine, oxolane, thiolane, imidazole, oxazole, piperidine, piperazine, morpholine. The heterocyclic ring can be substituted at one or more positions with such substituents as, for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —CF₃, —CN, or the like. Heterocycles may also be bridged or fused to other cyclic groups as described below.

The term "polycyclic group" as used herein is intended to refer to two or more saturated or unsaturated (i.e., aromatic) cyclic rings in which two or more carbons are common to two adjoining rings, e.g., the rings are "fused rings". Rings that are joined through non-adjacent atoms are termed "bridged" rings. Each of the rings of the polycyclic group can be substituted with such substituents as described above, as for example, halogens, alkyls, cycloalkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN, or the like.

Figure 2:
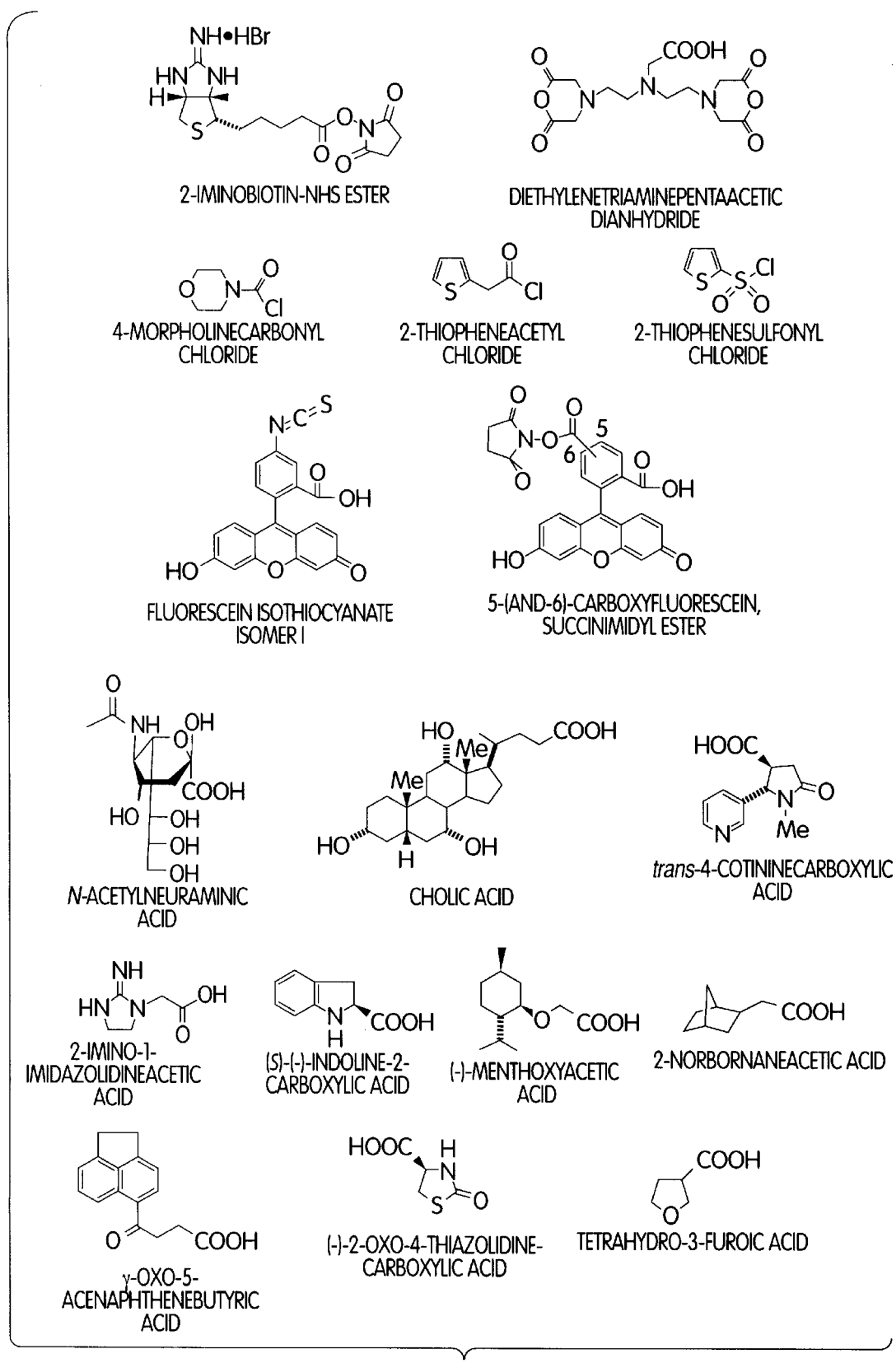
FIG. 2 is a schematic representation of compounds which can be used to modify a β-AP or an Aβ aggregation core domain to form a β-amyloid modulator of the invention.

A preferred polycyclic group is a group containing a cis-decalin structure. Although not intending to be limited by mechanism, it is thought that the "bent" conformation conferred on a modifying group by the presence of a cis-decalin structure contributes to the efficacy of the modifying group in disrupting Aβ polymerization. Accordingly, other structures which mimic the "bent" configuration of the cis-decalin structure can also be used as modifying groups. An example of a cis-decalin containing structure that can be used as a modifying group is a cholanoyl structure, such as a cholyl group. For example, a modulator compound can be modified at its amino terminus with a cholyl group by reacting the aggregation core domain with cholic acid, a bile acid, as described in Example 4 (the structure of cholic acid is illustrated in FIG. 2). Moreover, a modulator compound can be modified at its carboxy terminus with a cholyl group according to methods known in the art (see e.g., Wess, G. et al. (1993) *Tetrahedron Letters*, 34:817–822; Wess, G. et al. (1992) *Tetrahedron Letters* 33:195–198; and Kramer, W. et al. (1992) *J. Biol. Chem.* 267:18598–18604). Cholyl derivatives and analogues can also be used as modifying groups. For example, a preferred cholyl derivative is Aic (3-(O-aminoethyl-iso)-cholyl), which has a free amino group that can be used to further modify the modulator compound (e.g., a chelation group for $^{99m}Tc$ can be introduced through the free amino group of Aic). As used herein, the term "cholanoyl structure" is intended to include the cholyl group and derivatives and analogues thereof, in particular those which retain a four-ring cis-decalin configuration. Examples of cholanoyl structures include groups derived from other bile acids, such as deoxycholic acid, lithocholic acid, ursodeoxycholic acid, chenodeoxycholic acid and hyodeoxycholic acid, as well as other related structures such as cholanic acid, bufalin and resibufogenin (although the latter two compounds are not preferred for use as a modifying group). Another example of a cis-decalin containing compound is 5β-cholestan-3α-ol (the cis-decalin isomer of (+)-dihydrocholesterol). For further description of bile acid and steroid structure and nomenclature, see Nes, W. R. and McKean, M. L. *Biochemistry of Steroids and Other Isopentanoids*, University Park Press, Baltimore, Md., Chapter 2.

In addition to cis-decalin containing groups, other polycyclic groups may be used as modifying groups. For example, modifying groups derived from steroids or β-lactams may be suitable modifying groups. Moreover, non-limiting examples of some additional cyclic, heterocyclic or polycyclic compounds which can be used to modify an Aβ-derived peptidic structure are shown schematically in FIG. 2. In one embodiment, the modifying group is a "biotinyl structure", which includes biotinyl groups and analogues and derivatives thereof (such as a 2-iminobiotinyl group). In another embodiment, the modifying group can comprise a "fluorescein-containing group", such as a group derived from reacting an Aβ-derived peptidic structure with 5-(and 6-)-carboxyfluorescein, succinimidyl ester or fluorescein isothiocyanate. In various other embodiments, the modifying group(s) can comprise an N-acetylneuraminyl group, a trans-4-cotininecarboxyl group, a 2-imino-1-imidazolidineacetyl group, an (S)-(-)-indoline-2-carboxyl group, a (-)-menthoxyacetyl group, a 2-norbornaneacetyl group, a γ-oxo-5-acenaphthenebutyryl, a (-)-2-oxo-4-thiazolidinecarboxyl group, a tetrahydro-3-furoyl group, a 2-iminobiotinyl group, a diethylenetriaminepentaacetyl group, a 4-morpholinecarbonyl group, a 2-thiopheneacetyl group or a 2-thiophenesulfonyl group.

Preferred modifying groups include groups comprising cholyl structures, biotinyl structures, fluorescein-containing groups, a diethylene-triaminepentaacetyl group, a (-)-menthoxyacetyl group, and a N-acetylneuraminyl group. More preferred modifying groups those comprising a cholyl structure or an iminiobiotinyl group.

In addition to the cyclic, heterocyclic and polycyclic groups discussed above, other types of modifying groups can be used in a modulator of the invention. For example, small hydrophobic groups may be suitable modifying groups. An example of a suitable non-cyclic modifying group is an acetyl group.

Yet another type of modifying group is a compound that contains a non-natural amino acid that acts as a beta-turn mimetic, such as a dibenzofuran-based amino acid described in Tsang, K. Y. et al. (1994) *J. Am. Chem. Soc.* 116:3988–4005; Diaz, H and Kelly, J. W. (1991) *Tetrahedron Letters* 41:5725–5728; and Diaz. H et al. (1992) *J. Am. Chem. Soc.* 114:8316–8318. An example of such a modifying group is a peptide-aminoethyldibenzofuranyl-proprionic acid (Adp) group (e.g., DDIIL-Adp; SEQ ID NO: 34). This type of modifying group further can comprise one or more N-methyl peptide bonds to introduce additional steric hindrance to the aggregation of natural β-AP when compounds of this type interact with natural β-AP.

III. Additional Chemical Modifications of Aβ Modulators

A β-amyloid modulator compound of the invention can be further modified to alter the specific properties of the compound while retaining the ability of the compound to alter Aβ aggregation and inhibit Aβ neurotoxicity. For example, in one embodiment, the compound is further modified to alter a pharmacokinetic property of the compound, such as in vivo stability or half-life. In another embodiment, the compound is further modified to label the compound with a detectable substance. In yet another embodiment, the compound is further modified to couple the compound to an additional therapeutic moiety. Schematically, a modulator of the invention comprising an Aβ aggregation core domain coupled directly or indirectly to at least one modifying group can be illustrated as MG-ACD, whereas this compound which has been further modified to alter the properties of the modulator can be illustrated as MG-ACD-CM, wherein CM represents an additional chemical modification.

To further chemically modify the compound, such as to alter the pharmacokinetic properties of the compound, reactive groups can be derivatized. For example, when the modifying group is attached to the amino-terminal end of the aggregation core domain, the carboxy-terminal end of the compound can be further modified. Preferred C-terminal modifications include those which reduce the ability of the compound to act as a substrate for carboxypeptidases. Examples of preferred C-terminal modifiers include an amide group, an ethylamide group and various non-natural amino acids, such as D-amino acids and β-alanine. Alternatively, when the modifying group is attached to the carboxy-terminal end of the aggregation core domain, the amino-terminal end of the compound can be further modified, for example, to reduce the ability of the compound to act as a substrate for aminopeptidases.

A modulator compound can be further modified to label the compound by reacting the compound with a detectable substance. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{14}C$, $^{123}I$, $^{124}I$, $^{125}I$, $^{131}I$, $^{99m}Tc$, $^{35}S$ or $^3H$. In a preferred embodiment, a modulator compound is radioactively labeled with $^{14}C$, either by incorporation of $^{14}C$ into the modifying group or one or more amino acid structures in the modulator compound. Labeled modulator compounds can be used to assess the in vivo pharmacokinetics of the compounds, as well as to detect Aβ aggregation, for example for diagnostic purposes. Aβ aggregation can be detected using a labeled modulator compound either in vivo or in an in vitro sample derived from a subject.

Preferably, for use as an in vivo diagnostic agent, a modulator compound of the invention is labeled with radioactive technetium or iodine. Accordingly, in one embodiment, the invention provides a modulator compound labeled with technetium, preferably $^{99m}Tc$. Methods for labeling peptide compounds with technetium are known in the art (see e.g., U.S. Pat. Nos. 5,443,815, 5,225,180 and 5,405,597, all by Dean et al.; Stepniak-Biniakiewicz, D., et al. (1992) *J. Med. Chem.* 35:274–279; Fritzberg, A. R., et al. (1988) *Proc. Natl. Acad. Sci. USA* 85:4025–4029; Baidoo, K. E., et al. (1990) *Cancer Res. Suppl.* 50:799s–803s; and Regan, L. and Smith, C. K. (1995) *Science* 270:980–982). A modifying group can be chosen that provides a site at which a chelation group for $^{99m}Tc$ can be introduced, such as the Aic derivative of cholic acid, which has a free amino group (sec Example 11). In another embodiment, the invention provides a modulator compound labeled with radioactive iodine. For example, a phenylalanine residue within the Aβ sequence (such as $Phe_{19}$ or $Phe_{20}$) can be substituted with radioactive iodotyrosyl (see Example 11). Any of the various isotopes of radioactive iodine can be incorporated to create a diagnostic agent. Preferably, 123I (half-life=13.2 hours) is used for whole body scintigraphy, $^{124}I$ (half life=4 days) is used for positron emission tomography (PET), 125I (half life=60 days) is used for metabolic turnover studies and $^{131}I$ (half life=8 days) is used for whole body counting and delayed low resolution imaging studies.

Furthermore, an additional modification of a modulator compound of the invention can serve to confer an additional therapeutic property on the compound. That is, the additional chemical modification can comprise an additional functional moiety. For example, a functional moiety which serves to break down or dissolve amyloid plaques can be coupled to the modulator compound. In this form, the MG-ACD portion of the modulator serves to target the compound to Aβ peptides and disrupt the polymerization of the Aβ peptides, whereas the additional functional moiety serves to break down or dissolve amyloid plaques after the compound has been targeted to these sites.

In an alternative chemical modification, a β-amyloid compound of the invention is prepared in a "prodrug" form, wherein the compound itself does not modulate Aβ aggregation, but rather is capable of being transformed, upon metabolism in vivo, into a β-amyloid modulator compound as defined herein. For example, in this type of compound, the modulating group can be present in a prodrug form that is capable of being converted upon metabolism into the form of an active modulating group. Such a prodrug form of a modifying group is referred to herein as a "secondary modifying group." A variety of strategies are known in the art for preparing peptide prodrugs that limit metabolism in order to optimize delivery of the active form of the peptide-based drug (see e.g., Moss, J. (1 995) in *Peptide-Based Drug Design: Controlling Transport and Metabolism*, Taylor, M. D. and Amidon, G. L. (eds), Chapter 18. Additionally strategies have been specifically tailored to achieving CNS delivery based on "sequential metabolism" (see e.g., Bodor, N., et al. (1992) *Science* 257:1698–1700; Prokai, L., et al. (1994) *J. Am. Chem. Soc.* 116:2643–2644; Bodor, N. and Prokai, L. (1995) in *Peptide-Based Drug Design: Controlling Transport and Metabolism*, Taylor, M. D. and Amidon, G. L. (eds), Chapter 14. In one embodiment of a prodrug form of a modulator of the invention, the modifying group comprises an alkyl ester to facilitate blood-brain barrier permeability.

Modulator compounds of the invention can be prepared by standard techniques 30 known in the art. The peptide component of a modulator composed, at least in part, of a peptide, can be synthesized using standard techniques such as those described in Bodansky, M. *Principles of Peptide Synthesis*, Springer Verlag, Berlin (1993) and Grant, G. A (ed.). *Synthetic Peptides: A User's Guide*, W.H. Freeman and Company, New York (1992). Automated peptide synthesizers are commercially available (e.g., Advanced ChemTech Model 396; Milligen/Biosearch 9600). Additionally, one or more modulating groups can be attached to the Aβ-derived peptidic component (e.g., an Aβ aggregation core domain) by standard methods, for example using methods for reaction through an amino group (e.g., the alpha-amino group at the amino-terminus of a peptide), a carboxyl group (e.g., at the carboxy terminus of a peptide), a hydroxyl group (e.g., on a tyrosine, scrine or threonine residue) or other suitable reactive group on an amino acid side chain (see e.g., Greene, T. W and Wuts, P. G. M. *Protective Groups in Organic Synthesis*, John Wiley and Sons, Inc., New York (1991)). Exemplary syntheses of preferred β amyloid modulators is described further in Examples 1, 4 and 11.

IV. Screening Assays

Another aspect of the invention pertains to a method for selecting a modulator of β-amyloid aggregation. In the method, a test compound is contacted with natural β amyloid peptides, the aggregation of the natural β-AP is measured and a modulator is selected based on the ability of the test compound to alter the aggregation of the natural β-AP (e.g., inhibit or promote aggregation). In a preferred embodiment, the test compound is contacted with a molar excess amount of the natural β-AP. The amount and/or rate of natural β-AP aggregation in the presence of the test compound can be determined by a suitable assay indicative of β-AP aggregation, as described herein (see e.g., Examples 2, 5 and 6).

In a preferred assay, the natural β-AP is dissolved in solution in the presence of the test compound and aggregation of the natural β-AP is assessed in a nucleation assay (see Example 6) by assessing the turbidity of the solution over time, as measured by the apparent absorbance of the solution at 405 nm (described further in Example 6; see also Jarrett et al. (1993) *Biochemistry* 32:4693–4697). In the absence of a β-amyloid modulator, the $A_{405\,nm}$ of the solution typically stays relatively constant during a lag time in which the β-AP remains in solution, but then the $A_{405\,nm}$ of the solution rapidly increases as the β-AP aggregates and comes out of solution, ultimately reaching a plateau level (i.e., the $A_{405\,nm}$ of the solution exhibits sigmoidal kinetics over time). In contrast, in the presence of a test compound that inhibits β-AP aggregation, the $A_{405\,nm}$ of the solution is reduced compared to when the modulator is absent. Thus, in the presence of the inhibitory modulator, the solution may exhibit an increased lag time, a decreased slope of aggregation and/or a lower plateau level compared to when the modulator is absent. This method for selecting a modulator of β-amyloid polymerization can similarly be used to select modulators that promote β-AP aggregation. Thus, in the presence of a modulator that promotes β-AP aggregation, the $A_{405\,nm}$ of the solution is increased compared to when the modulator is absent (e.g., the solution may exhibit an decreased lag time, increase slope of aggregation and/or a higher plateau level compared to when the modulator is absent).

Another assay suitable for use in the screening method of the invention, a seeded extension assay, is also described further in Example 6. In this assay, β-AP monomer and an aggregated β-AP "seed" are combined, in the presence and absence of a test compound, and the amount of β-fibril formation is assayed based on enhanced emission of the dye Thioflavine T when contacted with β-AP fibrils. Moreover, β-AP aggregation can be assessed by electron microscopy (EM) of the β-AP preparation in the presence or absence of the modulator. For example, β amyloid fibril formation, which is detectable by EM, is reduced in the presence of a modulator that inhibits β-AP aggregation (i. e., there is a reduced amount or number of β-fibrils in the presence of the modulator), whereas β fibril formation is increased in the presence of a modulator that promotes β-AP aggregation (i.e., there is an increased amount or number of β-fibrils in the presence of the modulator).

An even more preferred assay for use in the screening method of the invention to select suitable modulators is the neurotoxicity assay described in Examples 3 and 10. Compounds are selected which inhibit the formation of neurotoxic Aβ aggregates and/or which inhibit the neurotoxicity of preformed Aβ fibrils. This neurotoxicity assay is considered to be predictive of neurotoxicity in vivo. Accordingly, inhibitory activity of a modulator compound in the in vitro neurotoxicity assay is predictive of similar inhibitory activity of the compound for neurotoxicity in vivo.

V. Pharmaceutical Compositions

Another aspect of the invention pertains to pharmaceutical compositions of the β-amyloid modulator compounds of the invention. In one embodiment, the composition includes a β amyloid modulator compound in a therapeutically or prophylactically effective amount sufficient to alter, and preferably inhibit, aggregation of natural β-amyloid peptides, and a pharmaceutically acceptable carrier. In another embodiment, the composition includes a β amyloid modulator compound in a therapeutically or prophylactically effective amount sufficient to inhibit the neurotoxicity of natural β-amyloid peptides, and a pharmaceutically acceptable carrier. A "therapeutically effective amount" refers to an amount effective, at dosages and for periods of time necessary, to achieve the desired therapeutic result, such as reduction or reversal or β-amyloid deposition and/or reduction or reversal of Aβ neurotoxicity. A therapeutically effective amount of modulator may vary according to factors such as the disease state, age, sex, and weight of the individual, and the ability of the modulator to elicit a desired response in the individual. Dosage regimens may be adjusted to provide the optimum therapeutic response. A therapeutically effective amount is also one in which any toxic or detrimental effects of the modulator are outweighed by the therapeutically beneficial effects. The potential neurotoxicity of the modulators of the invention can be assayed using the cell-based assay described in Examples 3 and 10 and a therapeutically effective modulator can be selected which does not exhibit significant neurotoxicity. In a preferred embodiment, a therapeutically effective amount of a modulator is sufficient to alter, and preferably inhibit, aggregation of a molar excess amount of natural β-amyloid peptides. A "prophylactically effective amount" refers to an amount effective, at dosages and for periods of time necessary, to achieve the desired prophylactic result, such as preventing or inhibiting the rate of β-amyloid deposition and/or Aβ neurotoxicity in a subject predisposed to β-amyloid deposition. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

One factor that may be considered when determining a therapeutically or prophylactically effective amount of a β amyloid modulator is the concentration of natural β-AP in a biological compartment of a subject, such as in the cerebrospinal fluid (CSF) of the subject. The concentration of natural β-AP in the CSF has been estimated at 3 nM (Schwartzman, (1994) *Proc. Natl. Acad. Sci. USA* 91:8368–8372). A non-limiting range for a therapeutically or prophylactically effective amounts of a β amyloid modulator is 0.01 nM–10 $\mu$M. It is to be noted that dosage values may vary with the severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

The amount of active compound in the composition may vary according to factors such as the disease state, age, sex, and weight of the individual, each of which may affect the amount of natural β-AP in the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier is suitable for administration into the central nervous system (e.g., intraspinally or intracerebrally). Alternatively, the carrier can be suitable for intravenous, intraperitoneal or intramuscular administration. In another embodiment, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the modulators can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g., β-amyloid modulator) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

A modulator compound of the invention can be formulated with one or more additional compounds that enhance the solubility of the modulator compound. Preferred compounds to be added to formulations to enhance the solubility of the modulators are cyclodextrin derivatives, preferably hydroxypropyl-γ-cyclodextrin. Drug delivery vehicles containing a cyclodextrin derivative for delivery of peptides to the central nervous system are described in Bodor, N., et al. (1992) *Science* 257:1698–1700. For the β-amyloid modulators described herein, inclusion in the formulation of hydroxypropyl-γ-cyclodextrin at a concentration 50–200 mM increases the aqueous solubility of the compounds. In addition to increased solubility, inclusion of a cyclodextrin derivative in the formulation may have other beneficial effects, since β-cyclodextrin itself has been reported to interact with the Aβ peptide and inhibit fibril formation in vitro (Camilleri, P., et al. (1994) *FEBS Letters* 341:256–258. Accordingly, use of a modulator compound of the invention in combination with a cyclodextrin derivative may result in greater inhibition of Aβ aggregation than use of the modulator alone. Chemical modifications of cyclodextrins are known in the art (Hanessian, S., et al. (1995) J. Org. Chem. 60:4786–4797). In addition to use as an additive in a pharmaceutical composition containing a modulator of the invention, cyclodextrin derivatives may also be useful as modifying groups and, accordingly, may also be covalently coupled to an Aβ peptide compound to form a modulator compound of the invention.

In another embodiment, a pharmaceutical composition comprising a modulator of the invention is formulated such that the modulator is transported across the blood-brain barrier (BBB). Various strategies known in the art for increasing transport across the BBB can be adapted to the modulators of the invention to thereby enhance transport of the modulators across the BBB (for reviews of such strategies, see e.g., Pardridge, W. M. (1994) *Trends in Biotechnol.* 12:239–245; Van Bree, J. B. et al. (1993) *Pharm. World Sci.* 15:2–9; and Pardridge, W. M. et al. (1992) *Pharmacol. Toxicol.* 71:3–10). In one approach, the modulator is chemically modified to form a prodrug with enhanced transmembrane transport. Suitable chemical modifications include covalent linking of a fatty acid to the modulator through an amide or ester linkage (see e.g., U.S. Pat. No. 4,933,324 and PCT Publication WO 89/07938, both by Shashoua; U.S. Pat. No. 5,284,876 by Hesse et al.; Toth, I. et al. (1994) *J. Drug Target*. 2:217–239; and Shashoua, V. E. et al. (1984) *J. Med. Chem.* 27:659–664) and glycating the modulator (see e.g., U.S. Pat. No. 5,260,308 by Poduslo et al.). Also, N-acylamino acid derivatives may be used in a modulator to form a "lipidic" prodrug (see e.g., U.S. Pat. No. 5,112,863 by Hashimoto et al.).

In another approach for enhancing transport across the BBB, a peptidic or peptidomimetic modulator is conjugated to a second peptide or protein, thereby forming a chimeric protein, wherein the second peptide or protein undergoes absorptive-mediated or receptor-mediated transcytosis through the BBB. Accordingly, by coupling the modulator to this second peptide or protein, the chimeric protein is transported across the BBB. The second peptide or protein can be a ligand for a brain capillary endothelial cell receptor ligand. For example, a preferred ligand is a monoclonal antibody that specifically binds to the transferrin receptor on brain capillary endothelial cells (see e.g., U.S. Pat. Nos. 5,182,107 and 5,154,924 and PCT Publications WO 93/10819 and WO 95/02421, all by Friden et al.). Other suitable peptides or proteins that can mediate transport across the BBB include histones (see e.g., U.S. Pat. No. 4,902,505 by Pardridge and Schimmel) and ligands such as biotin, folate, niacin, pantothenic acid, riboflavin, thiamin, pryridoxal and ascorbic acid (see e.g., U.S. Pat. Nos. 5,416, 016 and 5,108,921, both by Heinstein). Additionally, the glucose transporter GLUT-1 has been reported to transport glycopeptides (L-serinyl-β-D-glucoside analogues of

[Met5]enkephalin) across the BBB (Polt, R. et al. (1994) *Proc. Natl. Acad. Sci. USA* 91:7114–1778). Accordingly, a modulator compound can be coupled to such a glycopeptide to target the modulator to the GLUT-1 glucose transporter. For example, a modulator compound which is modified at its amino terminus with the modifying group Aic (3-(O-aminoethyl-iso)-cholyl, a derivative of cholic acid having a free amino group) can be coupled to a glycopeptide through the amino group of Aic by standard methods. Chimeric proteins can be formed by recombinant DNA methods (e.g., by formation of a chimeric gene encoding a fusion protein) or by chemical crosslinking of the modulator to the second peptide or protein to form a chimeric protein. Numerous chemical crosslinking agents are known in the (e.g., commercially available from Pierce, Rockford Ill.). A crosslinking agent can be chosen which allows for high yield coupling of the modulator to the second peptide or protein and for subsequent cleavage of the linker to release bioactive modulator. For example, a biotin-avidin-based linker system may be used.

In yet another approach for enhancing transport across the BBB, the modulator is encapsulated in a carrier vector which mediates transport across the BBB. For example, the modulator can be encapsulated in a liposome, such as a positively charged unilamellar liposome (see e.g., PCT Publications WO 88/07851 and WO 88/07852, both by Faden) or in polymeric microspheres (see e.g., U.S. Pat. No. 5,413,797 by Khan et al., U.S. Pat. No. 5,271,961 by Mathiowitz et al. and 5,019,400 by Gombotz et al.). Moreover, the carrier vector can be modified to target it for transport across the BBB. For example, the carrier vector (e.g., liposome) can be covalently modified with a molecule which is actively transported across the BBB or with a ligand for brain endothelial cell receptors, such as a monoclonal antibody that specifically binds to transferrin receptors (see e.g., PCT Publications WO 91/04014 by Collins et al. and WO 94/02178 by Greig et al.).

In still another approach to enhancing transport of the modulator across the BBB, the modulator is coadministered with another agent which functions to permeabilize the BBB. Examples of such BBB "permeabilizers" include bradykinin and bradykinin agonists (see e.g., U.S. Pat. No. 5,112,596 by Malfroy-Camine) and peptidic compounds disclosed in U.S. Pat. No. 5,268,164 by Kozarich et al.

A modulator compound of the invention can be formulated into a pharmaceutical composition wherein the modulator is the only active compound or, alternatively, the pharmaceutical composition can contain additional active compounds. For example, two or more modulator compounds may be used in combination. Moreover, a modulator compound of the invention can be combined with one or more other agents that have anti-amyloidogenic properties. For example, a modulator compound can be combined with the non-specific cholinesterase inhibitor tacrine (COGNEX®, Parke-Davis).

In another embodiment, a pharmaceutical composition of the invention is provided as a packaged formulation. The packaged formulation may include a pharmaceutical composition of the invention in a container and printed instructions for administration of the composition for treating a subject having a disorder associated with β-amyloidosis, e.g. Alzheimer's disease.

VI. Methods of Using Aβ Modulators

Another aspect of the invention pertains to methods for altering the aggregation or inhibiting the neurotoxicity of natural β-amyloid peptides. In the methods of the invention, natural β amyloid peptides are contacted with a β amyloid modulator such that the aggregation of the natural β amyloid peptides is altered or the neurotoxicity of the natural β amyloid peptides is inhibited. In a preferred embodiment, the modulator inhibits aggregation of the natural β amyloid peptides. In another embodiment, the modulator promotes aggregation of the natural β amyloid peptides. Preferably, aggregation of a molar excess amount of β-AP, relative to the amount of modulator, is altered upon contact with the modulator.

In the method of the invention, natural β amyloid peptides can be contacted with a modulator either in vitro or in vivo. Thus, the term "contacted with" is intended to encompass both incubation of a modulator with a natural β-AP preparation in vitro and delivery of the modulator to a site in vivo where natural β-AP is present. Since the modulator compound interacts with natural β-AP, the modulator compounds can be used to detect natural β-AP, either in vitro or in vivo. Accordingly, one use of the modulator compounds of the invention is as diagnostic agents to detect the presence of natural β-AP, either in a biological sample or in vivo in a subject. Furthermore, detection of natural β-AP utilizing a modulator compound of the invention further can be used to diagnose amyloidosis in a subject. Additionally, since the modulator compounds of the invention disrupt β-AP aggregation and inhibit β-AP neurotoxicity, the modulator compounds also are useful in the treatment of disorders associated with β-amyloidosis, either prophylactically or therapeutically. Accordingly, another use of the modulator compounds of the invention is as therapeutic agents to alter aggregation and/or neurotoxicity of natural β-AP.

In one embodiment, a modulator compound of the invention is used in vitro, for example to detect and quantitate natural β-AP in sample (e.g., a sample of biological fluid). To aid in detection, the modulator compound can be modified with a detectable substance. The source of natural β-AP used in the method can be, for example, a sample of cerebrospinal fluid (e.g., from an AD patient, an adult susceptible to AD due to family history, or a normal adult). The natural β-AP sample is contacted with a modulator of the invention and aggregation of the β-AP is measured, such as by as assay described in Examples 2, 5 and 6. Preferably, the nucleation assay and/or seeded extension assay described in Example 6 is used. The degree of aggregation of the β-AP sample can then be compared to that of a control sample(s) of a known concentration of β-AP, similarly contacted with the modulator and the results can be used as an indication of whether a subject is susceptible to or has a disorder associated with β-amyloidosis. Moreover, β-AP can be detected by detecting a modulating group incorporated into the modulator. For example, modulators incorporating a biotin compound as described herein (e.g., an amino-terminally biotinylated β-AP peptide) can be detected using a streptavidin or avidin probe which is labeled with a detectable substance (e.g., an enzyme, such as peroxidase). Detection of natural β-AP aggregates mixed with a modulator of the invention using a probe that binds to the modulating group (e.g., biotin/streptavidin) is described further in Example 2.

In another embodiment, a modulator compound of the invention is used in vivo to detect, and, if desired, quantitate, natural β-AP deposition in a subject, for example to aid in the diagnosis of β amyloidosis in the subject. To aid in detection, the modulator compound can be modified with a detectable substance, preferably $^{99m}$Tc or radioactive iodine (described further above), which can be detected in vivo in a subject. The labeled β-amyloid modulator compound is administered to the subject and, after sufficient time to allow accumulation of the modulator at sites of amyloid deposition, the labeled modulator compound is detected by standard imaging techniques. The radioactive signal generated by the labeled compound can be directly detected (e.g., whole body counting), or alternatively, the radioactive signal can be converted into an image on an autoradiograph or on a computer screen to allow for imaging of amyloid deposits in the subject. Methods for imaging amyloidosis using radiolabeled proteins are known in the art. For example, serum amyloid P component (SAP), radiolabeled with either $^{123}$I or $^{99m}$Tc, has been used to image systemic amyloidosis (see e.g., Hawkins, P. N. and Pepys, M. B. (1995) *Eur. J. Nucl. Med.* 22:595–599). Of the various isotypes of radioactive iodine, preferably $^{123}$I (half-life=13.2 hours) is used for whole body scintigraphy, $^{124}$I (half life=4 days) is used for positron emission tomography (PET), $^{125}$I (half life=60 days) is used for metabolic turnover studies and $^{131}$I (half life=8 days) is used for whole body counting and delayed low resolution imaging studies. Analogous to studies using radiolabeled SAP, a labeled modulator compound of the invention can be delivered to a subject by an appropriate route (e.g., intravenously, intraspinally, intracerebrally) in a single bolus, for example containing 100 µg of labeled compound carrying approximately 180 MBq of radioactivity.

The invention provides a method for detecting the presence or absence of natural β-amyloid peptides in a biological sample, comprising contacting a biological sample with a compound of the invention and detecting the compound bound to natural β-amyloid peptides to thereby detect the presence or absence of natural β-amyloid peptides in the biological sample. In one embodiment, the β-amyloid modulator compound and the biological sample are contacted in vitro. In another embodiment, the β-amyloid modulator compound is contacted with the biological sample by administering the β-amyloid modulator compound to a subject. For in vivo administration, preferably the compound is labeled with radioactive technetium or radioactive iodine.

The invention also provides a method for detecting natural β-amyloid peptides to facilitate diagnosis of a β-amyloidogenic disease, comprising contacting a biological sample with the compound of the invention and detecting the compound bound to natural β-amyloid peptides to facilitate diagnosis of a β-amyloidogenic disease. In one embodiment, the β-amyloid modulator compound and the biological sample are contacted in vitro. In another embodiment, the β-amyloid modulator compound is contacted with the biological sample by administering the β-amyloid modulator compound to a subject. For in vivo administration, preferably the compound is labeled with radioactive technetium or radioactive iodine. Preferably, use of the method facilitates diagnosis of Alzheimer's disease.

In another embodiment, the invention provides a method for altering natural β-AP aggregation or inhibiting β-AP neurotoxicity, which can be used prophylactically or therapeutically in the treatment or prevention of disorders associated with β amyloidosis, e.g., Alzheimer's Disease. As demonstrated in Example 10, modulator compounds of the invention reduce the toxicity of natural β-AP aggregates to cultured neuronal cells. Moreover, the modulators not only reduce the formation of neurotoxic aggregates but also have the ability to reduce the neurotoxicity of preformed Aβ fibrils. Accordingly, the modulator compounds of the invention can be used to inhibit or prevent the formation of neurotoxic Aβ fibrils in subjects (e.g., prophylactically in a subject predisposed to β-amyloid deposition) and can be used to reverse β-amyloidosis therapeutically in subjects already exhibiting β-amyloid deposition.

A modulator of the invention is contacted with natural β amyloid peptides present in a subject (e.g., in the cerebrospinal fluid or cerebrum of the subject) to thereby alter the aggregation of the natural β-AP and/or inhibit the neurotoxicity of the natural β-APs. A modulator compound alone can be administered to the subject, or alternatively, the modulator compound can be administered in combination with other therapeutically active agents (e.g., as discussed above in subsection IV). When combination therapy is employed, the therapeutic agents can be coadministered in a single pharmaceutical composition, coadministered in separate pharmaceutical compositions or administered sequentially.

The modulator may be administered to a subject by any suitable route effective for inhibiting natural β-AP aggregation in the subject, although in a particularly preferred embodiment, the modulator is administered parenterally, most preferably to the central nervous system of the subject. Possible routes of CNS administration include intraspinal administration and intracerebral administration (e.g., intracerebrovascular administration). Alternatively, the compound can be administered, for example, orally, intraperitoneally, intravenously or intramuscularly. For non-CNS administration routes, the compound can be administered in a formulation which allows for transport across the BBB. Certain modulators may be transported across the BBB without any additional further modification whereas others may need further modification as described above in subsection IV.

Suitable modes and devices for delivery of therapeutic compounds to the CNS of a subject are known in the art, including cerebrovascular reservoirs (e.g., Ommaya or Rikker reservoirs; see e.g., Raney, J. P. et al. (1988) *J. Neurosci. Nurs.* 20:23–29; Sundaresan, N. et al. (1989) *Oncology* 3:15–22), catheters for intrathecal delivery (e.g., Port-a-Cath, Y-catheters and the like; see e.g., Plummer, J. L. (1991) *Pain* 44:215–220; Yaksh, T. L. et al. (1986) *Pharmacol. Biochem. Behav.* 25:483–485), injectable intrathecal reservoirs (e.g., Spinalgesic; see e.g., Brazenor, G. A. (1987) *Neurosurgery* 21:484–491), implantable infusion pump systems (e.g., Infusaid; see e.g., Zierski, J. et al. (1988) *Acta Neurochem. Suppl.* 43:94–99; Kanoff, R. B. (1994) *J. Am. Osteopath. Assoc.* 94:487–493) and osmotic pumps (sold by Alza Corporation). A particularly preferred mode of administration is via an implantable, externally programmable infusion pump. Suitable infusion pump systems and reservoir systems are also described in U.S. Pat. No. 5, 368,562 by Blomquist and U.S. Pat. No. 4,731,058 by Doan, developed by Pharmacia Deltec Inc.

The method of the invention for altering β-AP aggregation in vivo , and in particular for inhibiting β-AP aggregation, can be used therapeutically in diseases associated with abnormal β amyloid aggregation and deposition to thereby slow the rate of β amyloid deposition and/or lessen the degree of β amyloid deposition, thereby ameliorating the course of the disease. In a preferred embodiment, the method is used to treat Alzheimer's disease (e.g., sporadic or familial AD, including both individuals exhibiting symptoms of AD and individuals susceptible to familial AD). The method can also be used prophylactically or therapeutically to treat other clinical occurrences of β amyloid deposition, such as in Down's syndrome individuals and in patients with hereditary cerebral hemorrhage with amyloidosis-Dutch-type (HCHWA-D). While inhibition of β-AP aggregation is a preferred therapeutic method, modulators that promote β-AP aggregation may also be useful therapeutically by allowing for the sequestration of β-AP at sites that do not lead to neurological impairment.

Additionally, abnormal accumulation of β-amyloid precursor protein in muscle fibers has been implicated in the pathology of sporadic inclusion body myositis (IBM) (Askana, V. et al. (1996) *Proc. Natl. Acad. Sci. USA* 93:1314–1319; Askanas, V. et al. (1995) *Current Opinion in Rheumatology* 7:486–496). Accordingly, the modulators of the invention can be used prophylactically or therapeutically in the treatment of disorders in which β-AP, or APP, is abnormally deposited at non-neurological locations, such as treatment of IBM by delivery of the modulators to muscle fibers.

VII. Unmodified Aβ Peptides that Inhibit Aggregation of Natural β-AP

In addition to the β-amyloid modulators described hereinbefore in which an Aβ peptide is coupled to a modifying group, the invention also provides β-amyloid modulators comprised of an unmodified Aβ peptide. It has now been discovered that certain portions of natural β-AP can alter aggregation of natural β-APs when contacted with the natural β-APs (see Example 12). Accordingly, these unmodified Aβ peptides comprise a portion of the natural β-AP sequence (i.e., a portion of β-AP$_{1-39}$, β-AP$_{1-40}$, β-AP$_{1-42}$ and β-AP$_{1-43}$). In particular these unmodified Aβ peptides have at least one amino acid deletion compared to β-AP$_{1-39}$, the shortest natural β-AP, such that the compound alters aggregation of natural β-amyloid peptides when contacted with the natural β-amyloid peptides. In various embodiments, these unmodified peptide compounds can promote aggregation of natural β-amyloid peptides, or, more preferably, can inhibit aggregation of natural β-amyloid peptides when contacted with the natural β-amyloid peptides. Even more preferably, the unmodified peptide compound inhibits aggregation of natural β-amyloid peptides when contacted with a molar excess amount of natural β-amyloid peptides (e.g., a 10-fold, 33-fold or 100-fold molar excess amount of natural β-AP).

As discussed above, the unmodified peptide compounds of the invention comprise an amino acid sequence having at least one amino acid deletion compared to the amino acid sequence of β-AP$_{1-39}$. Alternatively, the unmodified peptide compound can have at least five, ten, fifteen, twenty, twenty-five, thirty or thirty-five amino acids deleted compared to β-AP$_{1-39}$. Still further the unmodified peptide compound can have 1–5, 1–10, 1–15, 1–20, 1–25, 1–30 or 1–35 amino acids deleted compared to β-AP$_{1-39}$. The amino acid deletion(s) may occur at the amino-terminus, the carboxy-terminus, an internal site, or a combination thereof, of the β-AP sequence. Accordingly, in one embodiment, an unmodified peptide compound of the invention comprises an amino acid sequence which has at least one internal amino acid deleted compared to β-AP$_{1-39}$. Alternatively, the unmodified peptide compound can have at least five, ten, fifteen, twenty, twenty-five, thirty or thirty-five internal amino acids deleted compared to β-AP$_{1-39}$. Still further the unmodified peptide compound can have 1–5, 1–10, 1–15, 1–20, 1–25, 1–30 or 1–35 internal amino acids deleted compared to [APS $_{39}$. For peptides with internal deletions, preferably the peptide has an amino terminus corresponding to amino acid residue 1 of natural βAP and a carboxy terminus corresponding to residue 40 of natural βAP and has one or more internal β-AP amino acid residues deleted (i.e., a non-contiguous Aβ peptide).

In another embodiment, the unmodified peptide compound comprises an amino acid sequence which has at least one N-terminal amino acid deleted compared to β-AP$_{1-39}$ Alternatively, the unmodified peptide compound can have at least five, ten, fifteen, twenty, twenty-five, thirty or thirty-five N-terminal amino acids deleted compared to β-AP$_{1-39}$. Still further the unmodified peptide compound can have 1–5, 1–10, 1–15, 1–20, 1–25, 1–30 or 1–35 N-terminal amino acids deleted compared to β-AP$_{1-39}$.

In yet another embodiment, the unmodified peptide compound comprises an amino 35 acid sequence which has at least one C-terminal amino acid deleted compared to β-AP$_{1-39}$ Alternatively, the unmodified peptide compound can have at least five, ten, fifteen, twenty, twenty-five, thirty or thirty-five C-terminal amino acids deleted compared to βAP$_{1-39}$. Still further the unmodified peptide compound can have 1–5, 1–10, 1–15, 1–20, 1–25, 1–30 or 1–35 C-terminal amino acids deleted compared to β-AP$_{1-39}$.

In addition to deletion of amino acids as compared to β-AP$_{1-39}$, the peptide compound can have additional non-β-AP amino acid residues added to it, for example, at the amino terminus, the carboxy-terminus or at an internal site. In one embodiment, the peptide compound has at least one non-β-amyloid peptide-derived amino acid at its N-terminus. Alternatively, the compound can have, for example, 1–3, 1–5, 1–7, 1–10, 1–15 or 1–20 non-β-amyloid peptide-derived amino acid at its N-terminus. In another embodiment, the peptide compound has at least one non-β-amyloid peptide-derived amino acid at its C-terminus. Alternatively, the compound can have, for example, 1–3, 1–5, 1–7, 1–10, 1–15 or 1–20 non-β-amyloid peptide-derived amino acid at its C-terminus.

In specific preferred embodiments, an unmodified peptide compound of the invention comprises Aβ$_{6-20}$ (the amino acid sequence of which is shown in SEQ ID NO: 4), Aβ$_{16-30}$ (the amino acid sequence of which is shown in SEQ ID NO: 14), Aβ$_{1-20, 26-40}$ (the amino acid sequence of which is shown in SEQ ID NO: 15) or EEVVHHHHQQ-βAP$_{16-40}$ (the amino acid sequence of which is shown in SEQ ID NO: 16). In the nomenclature used herein, β-AP$_{1-20, 26-40}$ represents βAP$_{1-40}$ in which the internal amino acid residues 21–25 have been deleted.

An unmodified peptide compound of the invention can be chemically synthesized using standard techniques such as those described in Bodansky, M. *Principles of Peptide Synthesis*, Springer Verlag, Berlin (1993) and Grant, G. A (ed.). *Synthetic Peptides: A User's Guide*, W. H. Freeman and Company, New York (1992). Automated peptide synthesizers are commercially available (e.g., Advanced ChemTech Model 396; Milligen/Biosearch 9600). Alternatively, unmodified peptide compounds can be prepared according to standard recombinant DNA techniques using a nucleic acid molecule encoding the peptide. A nucleotide sequence encoding the peptide can be determined using the genetic code and an oligonucleotide molecule having this nucleotide sequence can be synthesized by standard DNA synthesis methods (e.g., using an automated DNA synthesizer). Alternatively, a DNA molecule encoding an unmodified peptide compound can be derived from the natural β-amyloid precursor protein gene or cDNA (e.g., using the polymerase chain reaction and/or restriction enzyme digestion) according to standard molecular biology techniques.

Accordingly, the invention further provides an isolated nucleic acid molecule comprising a nucleotide sequence encoding a β-amyloid peptide compound, the β-amyloid peptide compound comprising an amino acid sequence having at least one amino acid deletion compared to β-AP$_{1-39}$ such that the β-amyloid peptide compound alters aggregation of natural β-amyloid peptides when contacted with the natural β-amyloid peptides. As used herein, the term "nucleic acid molecule" is intended to include DNA molecules and RNA molecules and may be single-stranded or double-stranded, but preferably is double-stranded DNA.

The isolated nucleic acid encodes a peptide wherein one or more amino acids are deleted from the N-terminus, C-terminus and/or an internal site of $\beta$-AP$_{1-39}$, as discussed above. In yet other embodiments, the isolated nucleic acid encodes a peptide compound having one or more amino acids deleted compared to $\beta$-AP$_{1-39}$ and further having at least one non-$\beta$-AP derived amino acid residue added to it, for example, at the amino terminus, the carboxy-terminus or at an internal site. In specific preferred embodiments, an isolated nucleic acid molecule of the invention encodes $\beta$-AP$_{16-20}$, $\beta$-AP$_{16-30}$, $\beta$-AP$_{1-20,\ 26-40}$ or EEVVHHHHQQ-$\beta$-AP$_{16-40}$ (SEQ ID NO: 16).

To facilitate expression of a peptide compound in a host cell by standard recombinant DNA techniques, the isolated nucleic acid encoding the peptide is incorporated into a recombinant expression vector. Accordingly, the invention also provides recombinant expression vectors comprising the nucleic acid molecules of the invention. As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors, which serve equivalent functions.

In the recombinant expression vectors of the invention, the nucleotide sequence encoding the peptide compound are operatively linked to one or more regulatory sequences, selected on the basis of the host cells to be used for expression. The term "operably linked" is intended to mean that the sequences encoding the peptide compound are linked to the regulatory sequence(s) in a manner that allows for expression of the peptide compound. The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those that direct constitutive expression of a nucleotide sequence in many types of host cell, those that direct expression of the nucleotide sequence only in certain host cells (e.g., tissue-specific regulatory sequences) and those that direct expression in a regulatable manner (e.g., only in the presence of an inducing agent). It will be appreciated by those skilled in the art that the design of the expression vector may depend on such factors as the choice of the host cell to be transformed, the level of expression of peptide compound desired, etc. The expression vectors of the invention can be introduced into host cells thereby to produce peptide compounds encoded by nucleic acids as described herein.

The recombinant expression vectors of the invention can be designed for expression of peptide compounds in prokaryotic or eukaryotic cells. For example, peptide compounds can be expressed in bacterial cells such as *E. coli*, insect cells (using baculovirus expression vectors) yeast cells or mammalian cells. Suitable host cells are discussed further in Goeddel, *Gene Expression Technology. Methods in Enzymology* 185, Academic Press, San Diego, Calif. (1990). Alternatively, the recombinant expression vector may be transcribed and translated in vitro, for example using T7 promoter regulatory sequences and T7 polymerase. Examples of vectors for expression in yeast *S. cerivisae* include pYepSec1 (Baldari et al., (1987) *EMBO J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.). Baculovirus vectors available for expression of proteins or peptides in cultured insect cells (e.g., Sf 9 cells) include the pAc series (Smith et al., (1983) *Mol. Cell. Biol.* 3:2156–2165) and the pVL series (Lucklow, V. A., and Summers, M. D., (1989) *Virology* 170:31–39). Examples of mammalian expression vectors include pCDM8 (Seed, B., (1987) *Nature* 329:840) and pMT2PC (Kaufman et al. (1987), *EMBO J.* 6:187–195). When used in mammalian cells, the expression vector's control functions are often provided by viral regulatory elements. For example, commonly used promoters are derived from polyoma, Adenovirus 2, cytomegalovirus and Simian Virus 40.

In addition to the regulatory control sequences discussed above, the recombinant expression vector may contain additional nucleotide sequences. For example, the recombinant expression vector may encode a selectable marker gene to identify host cells that have incorporated the vector. Such selectable marker genes are well known in the art. Moreover, the facilitate secretion of the peptide compound from a host cell, in particular mammalian host cells, the recombinant expression vector preferably encodes a signal sequence operatively linked to sequences encoding the amino-terminus of the peptide compound such that upon expression, the peptide compound is synthesized with the signal sequence fused to its amino terminus. This signal sequence directs the peptide compound into the secretory pathway of the cell and is then cleaved, allowing for release of the mature peptide compound (i.e., the peptide compound without the signal sequence) from the host cell. Use of a signal sequence to facilitate secretion of proteins or peptides from mammalian host cells is well known in the art.

A recombinant expression vector comprising a nucleic acid encoding a peptide compound that alters aggregation of natural $\beta$-AP can be introduced into a host cell to thereby produce the peptide compound in the host cell. Accordingly, the invention also provides host cells containing the recombinant expression vectors of the invention. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell may be any prokaryotic or eukaryotic cell. For example, a peptide compound may be expressed in bacterial cells such as *E. coli*, insect cells, yeast or mammalian cells. Preferably, the peptide compound is expressed in mammalian cells. In a preferred embodiment, the peptide compound is expressed in mammalian cells in vivo in a mammalian subject to treat amyloidosis in the subject through gene therapy (discussed further below). Preferably, the β-amyloid peptide compound encoded by the recombinant expression vector is secreted from the host cell upon being expressed in the host cell.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, electroporation, microinjection and viral-mediated transfection. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals. Methods for introducing DNA into mammalian cells in vivo are also known in the art and can be used to deliver the vector DNA to a subject for gene therapy purposes (discussed further below).

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those that confer resistance to drugs, such as G418, hygromycin and methotrexate. Nucleic acid encoding a selectable marker may be introduced into a host cell on the same vector as that encoding the peptide compound or may be introduced on a separate vector. Cells stably transfected with the introduced nucleic acid can be identified by drug selection (e.g., cells that have incorporated the selectable marker gene will survive, while the other cells die).

A nucleic acid of the invention can be delivered to cells in vivo using methods known in the art, such as direct injection of DNA, receptor-mediated DNA uptake or viral-mediated transfection. Direct injection has been used to introduce naked DNA into cells in vivo (see e.g., Acsadi et al. (1991) *Nature* 332: 815–818; Wolff et al. (1990) *Science* 247:1465–1468). A delivery apparatus (e.g., a "gene gun") for injecting DNA into cells in vivo can be used. Such an apparatus is commercially available (e.g., from BioRad). Naked DNA can also be introduced into cells by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. Additionally, a DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88:8850; Cristiano et al. (1993) *Proc. Natl. Acad. Sci. USA* 90:2122–2126).

Defective retroviruses are well characterized for use in gene transfer for gene therapy purposes (for a review see Miller, A. D. (1990) *Blood* 76:271). Protocols for producing recombinant retroviruses and for infecting cells in vitro or in vivo with such viruses can be found in *Current Protocols in Molecular Biology*, Ausubel, F. M. et al (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci. USA* 85:6460–6464; Wilson et al. (1988) *Proc. Natl. Acad. Sci. USA* 85:3014–3018; Armentano et al. (1990) *Proc. Natl. Acad. Sci. USA* 87:6141–6145; Huber et al. (1991) *Proc. Natl. Acad. Sci. USA* 88:8039–8043; Ferry et al. (1991) *Proc. Natl. Acad. Sci. USA* 88:8377–8381; Chowdhury et al. (1991) *Science* 254:1802–1805; van Beusechem et al. (1992) *Proc. Natl. Acad. Sci. USA* 89:7640–7644; Kay et al. (1992) *Human Gene Therapy* 3:641–647; Dai et al. (1992) *Proc. Natl. Acad. Sci. USA* 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Alternatively, the genome of an adenovirus can be manipulated such that it encodes and expresses a peptide compound but is inactivated in terms of its ability to replicate in a normal lytic viral life cycle. See for example Berkner et al. (1988) *BioTechniques* 6:616; Rosenfeld et al. (1991) *Science* 252:431–434; and Rosenfeld et al. (1992) *Cell* 68:143–155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89:6482–6486), hepatocytes (Herz and Gerard (1993) *Proc. Natl. Acad. Sci. USA* 90:2812–2816) and muscle cells (Quantin et al. (1992) *Proc. Natl. Acad. Sci. USA* 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA).

Adeno-associated virus (AAV) can also be used for delivery of DNA for gene therapy purposes. AAV is a naturally occurring defective virus that requires another virus, such as an adenovirus or a herpes virus, as a helper virus for efficient replication and a productive life cycle. (For a review see Muzyczka et al. *Curr. Topics in Micro. and Immunol.* (1992) 158:97–129). It is also one of the few viruses that may integrate its DNA into non-dividing cells, and exhibits a high frequency of stable integration (see for example Flotte et al. (1992) *Am. J. Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.*

2:32–39; Tratschin et al. (1984) *J. Virol.* 51:611–619; and Flotte et al. (1993) *J. Biol. Chem.* 268:3781–3790).

The invention provides a method for treating a subject for a disorder associated with β-amyloidosis, comprising administering to the subject a recombinant expression vector encoding a β-amyloid peptide compound, the compound comprising an amino acid sequence having at least one amino acid deletion compared to βAP$_{1-39}$, such that the β-amyloid peptide compound is synthesized in the subject and the subject is treated for a disorder associated with β-amyloidosis. Preferably, the disorder is Alzheimer's disease. In one embodiment the recombinant expression vector directs expression of the peptide compound in neuronal cells. In another embodiment, the recombinant expression vector directs expression of the peptide compound in glial cells. In yet another embodiment, the recombinant expression vector directs expression of the peptide compound in fibroblast cells.

General methods for gene therapy are known in the art. See for example, U.S. Pat. No. 5,399,346 by Anderson et al. A biocompatible capsule for delivering genetic material is described in PCT Publication WO 95/05452 by Baetge et al. Methods for grafting genetically modified cells to treat central nervous system disorders are described in U.S. Pat. No. 5,082,670 and in PCT Publications WO 90/06757 and WO 93/10234, all by Gage et al. Isolation and/or genetic modification of multipotent neural stem cells or neuro-derived fetal cells are described in PCT Publications WO 94/02593 by Anderson et al., WO 94/16718 by Weiss et al., and WO 94/23754 by Major et al. Fibroblasts transduced with genetic material are described in PCT Publication WO 89/02468 by Mulligan et al. Adenovirus vectors for transfering genetic material into cells of the central nervous system are described in PCT Publication WO 94/08026 by Kahn et al. Herpes simplex virus vectors suitable for treating neural disorders are described in PCT Publications WO 94/04695 by Kaplitt and WO 90/09441 by Geller et al. Promoter elements of the glial fibrillary acidic protein that can confer astrocyte specific expression on a linked gene or gene fragment, and which thus can be used for expression of Aβ peptides specifically in astrocytes, is described in PCT Publication WO 93/07280 by Brenner et al. Furthermore, alternative to expression of an Aβ peptide to modulate amyloidosis, an antisense oligonucleotide that is complementary to a region of the β-amyloid precursor protein mRNA corresponding to the peptides described herein can be expressed in a subject to modulate amyloidosis. General methods for expressing antisense oligonucleotides to modulate nervous system disorders are described in PCT Publication WO 95/09236.

Alternative to delivery by gene therapy, a peptide compound of the invention comprising an amino acid sequence having at least one amino acid deletion compared to β-AP$_{1-39}$ can be delivered to a subject by directly administering the peptide compound to the subject as described further herein for the modified peptide compounds of the invention. The peptide compound can be formulated into a pharmaceutical composition comprising a therapeutically effective amount of the β-amyloid peptide compound and a pharmaceutically acceptable carrier. The peptide compound can be contacted with natural β-amyloid peptides with a β-amyloid peptide compound such that aggregation of the natural β-amyloid peptides is inhibited. Moreover, the peptide compound can be administered to the subject in a therapeutically effective amount such that the subject is treated for a disorder associated with β-amyloidosis, such as Alzheimer's disease.

VIII. Other Embodiments

Although the invention has been illustrated hereinbefore with regard to Aβ peptide compounds, the principles described, involving attachment of a modifying group(s) to a peptide compound, are applicable to any amyloidogenic protein or peptide as a means to create a modulator compound that modulates, and preferably inhibits, amyloid aggregation. Accordingly, the invention provides modulator compounds that can be used to treat amyloidosis in a variety of forms and clinical settings.

Amyloidosis is a general term used to describe pathological conditions characterized by the presence of amyloid. Amyloid is a general term referring to a group of diverse but specific extracellular protein deposits which are seen in a number of different diseases. Though diverse in their occurrence, all amyloid deposits have common morphologic properties, stain with specific dyes (e.g., Congo red), and have a characteristic red-green birefringent appearance in polarized light after staining. They also share common ultrastructural features and common x-ray diffraction and infrared spectra. Amyloidosis can be classified clinically as primary, secondary, familial and/or isolated. Primary amyloid appears de novo without any preceding disorder. Secondary amyloid is that form which appears as a complication of a previously existing disorder. Familial amyloid is a genetically inherited form found in particular geographic populations. Isolated forms of amyloid are those that tend to involve a single organ system.

Different amyloids are characterized by the type of protein(s) or peptide(s) present in the deposit. For example, as described hereinbefore, amyloid deposits associated with Alzheimer's disease comprise the β-amyloid peptide and thus a modulator compound of the invention for detecting and/or treating Alzheimer's disease is designed based on modification of the β-amyloid peptide. The identities of the protein(s) or peptide(s) present in amyloid deposits associated with a number of other amyloidogenic diseases have been elucidated. Accordingly, modulator compounds for use in the detection and/or treatment of these other amyloidogenic diseases can be prepared in a similar fashion to that described herein for β-AP-derived modulators. In vitro assay systems can be established using an amyloidogenic protein or peptide which forms fibrils in vitro, analogous to the Aβ assays described herein. Modulators can be identified using such assay systems, based on the ability of the modulator to disrupt the β-sheet structure of the fibrils. Initially, an entire amyloidogenic protein can be modified or, more preferably, a peptide fragment thereof that is known to form fibrils in vitro can be modified (e.g., analogous to Aβ1-40 described herein). Amino acid deletion and substitution analyses can then be performed on the modified protein or peptide (analogous to the studies described in the Examples) to delineate an aggregation core domain that is sufficient, when modified, to disrupt fibril formation.

Non-limiting examples of amyloidogenic proteins or peptides, and their associated amyloidogenic disorders, include:

Transthyretin (TTR)—Amyloids containing transthyretin occur in familial amyloid polyneuropathy (Portuguese, Japanese and Swedish types), familial amyloid cardiomyopathy (Danish type), isolated cardiac amyloid and systemic senile amyloidosis. Peptide fragments of transthyretin have been shown to form amyloid fibrils in vitro. For example, TTR 10–20 and TTR 105–115 form amyloid-like fibrils in 20–30% acetonitrile/water at room temperature (Jarvis, J. A., et al.(1994) *Int. J. Pept. Protein Res.* 44:388–398). Moreover, familial cardiomyopathy (Danish type) is associated with mutation of Leu at position 111 to Met, and an analogue of TTR 105–115 in which the wildtype Leu at position 111 has been substituted with Met (TTR 105–115Met111) also forms amyloid-like fibrils in vitro (see e.g., Hermansen, L. F., et al. (1995) *Eur. J. Biochem.* 227:772–779; Jarvis et al. supra). Peptide fragments of TTR that form amyloid fibrils in vitro are also described in Jarvis, J. A., et al. (1993) *Biochem. Biophys. Res. Commun.* 192:991–998 and Gustavsson, A., et al. (1991) *Biochem. Biophys. Res. Commun.* 175:1159–1164. A peptide fragment of wildtype or mutated transthyretin that forms amyloid fibrils can be modified as described herein to create a modulator of amyloidosis that can be used in the detection or treatment of familial amyloid polyneuropathy (Portuguese, Japanese and Swedish types), familial amyloid cardiomyopathy (Danish type), isolated cardiac amyloid or systemic senile amyloidosis.

Prion Protein (PrP)—Amyloids in a number of spongiform encephalopathies, including scrapie in sheep, bovine spongiform encephalopathy in cows and Creutzfeldt-Jakob disease (CJ) and Gerstmann-Straussler-Scheinker syndrome (GSS) in humans, contain PrP. Limited proteolysis of PrPSc (the prion protein associated with scrapie) leads to a 27–30 kDa fragment (PrP27–30) that polymerizes into rod-shaped amyloids (see e.g., Pan, K. M., et al. (1993) *Proc. Natl. Acad. Sci. USA* 90:10962–10966; Gasset, M., et al. (1993) *Proc. Natl. Acad. Sci. USA* 90:1–5). Peptide fragments of PrP from humans and other mammals have been shown to form amyloid fibrils in vitro. For example, polypeptides corresponding to sequences encoded by normal and mutant alleles of the PRNP gene (encoding the precursor of the prion protein involved in CJ), in the regions of codon 178 and codon 200, spontaneously form amyloid fibrils in vitro (see e.g., Goldfarb, L. G., et al. (1993) *Proc. Natl. Acad. Sci. USA* 90:4451–4454). A peptide encompassing residues 106–126 of human PrP has been reported to form straight fibrils similar to those extracted from GSS brains, whereas a peptide encompassing residues 127–147 of human PrP has been reported to form twisted fibrils resembling scrapie-associated fibrils (Tagliavini, F., et al. (1993) *Proc. Natl. Acad. Sci. USA* 90:9678–9682). Peptides of Syrian hamster PrP encompassing residues 109–122, 113–127, 113–120, 178–191 or 202–218 have been reported to form amyloid fibrils, with the most amyloidogenic peptide being Ala-Gly-Ala-Ala-Ala-Ala-Gly-Ala (SEQ ID NO: 17), which corresponds to residues 113–120 of Syrian hamster PrP but which is also conserved in PrP from other species (Gasset, M., et al. (1992) *Proc. Natl. Acad. Sci. USA* 89:10940–10944). A peptide fragment of PrP that forms amyloid fibrils can be modified as described herein to create a modulator of amyloidosis that can be used in the detection or treatment of scrapie, bovine spongiform encephalopathy, Creutzfeldt-Jakob disease or Gerstmann-Straussler-Scheinker syndrome.

Islet Amyloid Polypeptide (IAPP, also known as amylin)—Amyloids containing IAPP occur in adult onset diabetes and insulinoma. IAPP is a 37 amino acid polypeptide formed from an 89 amino acid precursor protein (see e.g., Betsholtz, C., et al. (1989) *Exp. Cell. Res.* 183:484–493; Westermark, P., et al. (1987) *Proc. Natl. Acad. Sci. USA* 84:3881–3885). A peptide corresponding to IAPP residues 20–29 has been reported to form amyloid-like fibrils in vitro, with residues 25–29, having the sequence Ala-Ile-Leu-Ser-Ser (SEQ ID NO: 18), being strongly amyloidogenic (Westermark, P., et al. (1990) *Proc. Natl. Acad. Sci. USA* 87:5036–5040; Glenner, G. G., et al. (1988) *Biochem. Biophys. Res. Commun.* 155:608–614). A peptide fragment of IAPP that forms amyloid fibrils can be modified as described herein to create a modulator of amyloidosis that can be used in the detection or treatment of adult onset diabetes or insulinoma.

Atrial Natriuretic Factor (ANF)—Amyloids containing ANF are associated with isolated atrial amyloid (see e.g., Johansson, B., et al. (1987) *Biochem. Biophys. Res. Commun.* 148:1087–1092). ANF corresponds to amino acid residues 99–126 (proANF99–126) of the ANF prohormone (proANP1–126) (Pucci, A., et al. (1991) *J. Pathol.* 165:235–241). ANF, or a fragment thereof, that forms amyloid fibrils can be modified as described herein to create a modulator of amyloidosis that can be used in the detection or treatment of isolated atrial amyloid.

Kappa or Lambda Light Chain—Amyloids containing kappa or lambda light chains are associated idiopathic (primary) amyloidosis, myeloma or macroglobulinemia-associated amyloidosis, and primary localized cutaneous nodular amyloidosis associated with Sjogren's syndrome. The structure of amyloidogenic kappa and lambda light chains, including amino acid sequence analysis, has been characterized (see e.g., Buxbaum, J. N., et al. (1990) *Ann. Intern. Med.* 112:455–464; Schormann, N., et al. (1995) *Proc. Natl. Acad. Sci. USA* 92:9490–9494; Hurle, M. R., et al. (1994) *Proc. Natl. Acad. Sci. USA* 91:5446–5450; Liepnieks, J. J., et al. (1990) *Mol. Immunol.* 27:481–485; Gertz, M. A., et al. (1985) *Scand. J. Immunol.* 22:245–250; Inazumi, T., et al. (1994) *Dermatology* 189:125–128). Kappa or lambda light chains, or a peptide fragment thereof that forms amyloid fibrils, can be modified as described herein to create a modulator of amyloidosis that can be used in the detection or treatment of idiopathic (primary) amyloidosis, myeloma or macroglobulinemia-associated amyloidosis or primary localized cutaneous nodular amyloidosis associated with Sjogren's syndrome.

Amyloid A—Amyloids containing the amyloid A protein (AA protein), derived from serum amyloid A, are associated with reactive (secondary) amyloidosis (see e.g., Liepnieks, J. J., et al. (1995) *Biochim. Biophys. Acta* 1270:81–86), familial Mediterranean Fever and familial amyloid nephropathy with urticaria and deafness (Muckle-Wells syndrome) (see e.g., Linke, R. P., et al. (1983) *Lab. Invest.* 48:698–704). Recombinant human serum amyloid A forms amyloid-like fibrils in vitro (Yamada, T., et al. (1994) *Biochim. Biophys. Acta* 1226:323–329) and circular dichroism studies revealed a predominant β sheet/turn structure (McCubbin, W. D., et al. (1988) *Biochem J.* 256:775–783). Serum amyloid A, amyloid A protein or a fragment thereof that forms amyloid fibrils can be modified as described herein to create a modulator of amyloidosis that can be used in the detection or treatment of reactive (secondary) amyloidosis, familial Mediterranean Fever and familial amyloid nephropathy with urticaria and deafness (Muckle-Wells syndrome).

Cystatin C—Amyloids containing a variant of cystatin C are associated with hereditary cerebral hemorrhage with amyloidosis of Icelandic type. The disease is associated with a leucine to glycine mutation at position 68 and cystatin C containing this mutation aggregates in vitro (Abrahamson, M. and Grubb, A. (1994) *Proc. Natl. Acad. Sci. USA* 91:1416–1420). Cystatin C or a peptide fragment thereof that forms amyloid fibrils can be modified as described herein to create a modulator of amyloidosis that can be used in the detection or treatment of hereditary cerebral hemorrhage with amyloidosis of Icelandic type.

β2 microglobulin—Amyloids containing β2 microglobulin (β2M) are a major complication of long term hemodialysis (see e.g., Stein, G., et al. (1994) Nephrol. Dial. Transplant. 9:48–50; Floege, J., et al. (1992) Kidney Int. Suppl. 38:S78–S85; Maury, C. P. (1990) Rheumatol. Int. 10:1–8). The native β2M protein has been shown to form amyloid fibrils in vitro (Connors, L. H., et al. (1985) Biochem. Biophys. Res. Commun. 131:1063–1068; Ono, K., et al. (1994) Nephron 66:404–407). β2M, or a peptide fragment thereof that forms amyloid fibrils, can be modified as described herein to create a modulator of amyloidosis that can be used in the detection or treatment of amyloidosis associated with long term hemodialysis.

Apolipoprotein A-I (ApoA-I)—Amyloids containing variant forms of ApoA-I have been found in hereditary non-neuropathic systemic amyloidosis (familial amyloid polyneuropathy III). For example, N-terminal fragments (residues 1–86, 1–92 and 1–93) of an ApoA-I variant having a Trp to Arg mutation at position 50 have been detected in amyloids (Booth, D. R., et al. (1995) *QJM* 88:695–702). In another family, a leucine to arginine mutation at position 60 was found (Soutar, A.K., et al. (1992) *Proc. Natl. Acad. Sci. USA* 89:7389–7393). ApoA-I or a peptide fragment thereof that forms amyloid fibris can be modified as described herein to create a modulator of amyloidosis that can be used in the detection or treatment of hereditary non-neuropathic systemic amyloidosis.

Gelsolin—Amyloids containing variants of gelsolin are associated with familial amyloidosis of Finnish type. Synthetic gelsolin peptides that have sequence homology to wildtype or mutant gelsolins and that form amyloid fibrils in vitro are reported in Maury, C. P. et al. (1994) *Lab. Invest.* 70:558–564. A nine residue segment surrounding residue 187 (which is mutated in familial gelsolin amyloidosis) was defined as an amyloidogenic region (Maury, et al., supra; see also Maury, C. P., et al. (1992) *Biochem. Biophys. Res. Commun.* 183:227–231; Maury, C. P. (1991) *J. Clin. Invest.* 87:1195–1199). Gelsolin or a peptide fragment thereof that forms amyloid fibrils can be modified as described herein to create a modulator of amyloidosis that can be used in the detection or treatment of familial amyloidosis of Finnish type.

Procalcitonin or calcitonin—Amyloids containing procalcitonin, calcitonin or calcitonin-like immunoreactivity have been detected in amyloid fibrils associated with medullary carcinoma of the thyroid (see e.g., Butler, M. and Khan, S. (1986) Arch. Pathol. Lab. Med. 110:647–649; Sletten, K., et al. (1976) J. Exp. Med. 143:993–998). Calcitonin has been shown to form a nonbranching fibrillar structure in vitro (Kedar, I., et al. (1976) Isr. J. Med. Sci. 12:1137–1140). Procalcitonin, calcitonin or a fragment thereof that forms amyloid fibrils can be modified as described herein to create a modulator of amyloidosis that can be used in the detection or treatment of amyloidosis associated with medullary carcinoma of the thyroid.

Fibrinogen—Amyloids containing a variant form of fibrinogen alpha-chain have been found in hereditary renal amyloidosis. An arginine to leucine mutation at position 554 has been reported in amyloid fibril protein isolated from postmortem kidney of an affected individual (Benson, M. D., et al. (1993) *Nature Genetics* 3:252–255). Fibrinogen alpha-chain or a peptide fragment thereof that forms amyloid fibrils can be modified as described herein to create a modulator of amyloidosis that can be used in the detection or treatment of fibrinogen-associated hereditary renal amyloidosis.

Lysozyme—Amyloids containing a variant form of lysozyme have been found in hereditary systemic amyloidosis. In one family the disease was associated with a threonine to isoleucine mutation at position 56, whereas in another family the disease was associated with a histidine to aspartic acid mutation at position 67 (Pepys, M. B., et al. (1993) *Nature* 362:553–557). Lysozyme or a peptide fragment thereof that forms amyloid fibrils can be modified as described herein to create a modulator of amyloidosis that can be used in the detection or treatment of lysozyme-associated hereditary systemic amyloidosis.

This invention is further illustrated by the following examples which should not be construed as limiting. A modulator's ability to alter the aggregation of β-amyloid peptide in the assays described below are predictive of the modulator's ability to perform the same function in vivo. The contents of all references, patents and published patent applications cited throughout this application are hereby incorporated by reference.

EXAMPLE 1

Construction of β-Amyloid Modulators

A β-amyloid modulator composed of an amino-terminally biotinylated β-amyloid peptide of the amino acid sequence:

DAEFRHDSGYEVHHQKLVFFAEDVGSNK-GAIIGLMVGGVV (positions 1 to 40 of SEQ ID NO: 1) was prepared by solid-phase peptide synthesis using an $N^\alpha$-9-fluorenylmethyloxycarbonyl (FMOC)-based protection strategy as follows. Starting with 2.5 mmoles of FMOC-Val-Wang resin, sequential additions of each amino acid were performed using a four-fold excess of protected amino acids, 1-hydroxybenzotriazole (HOBt) and diisopropyl carbodiimide (DIC). Recouplings were performed when necessary as determined by ninhydrin testing of the resin after coupling. Each synthesis cycle was minimally described by a three minute deprotection (25% piperidine/N-methylpyrrolidone (NMP)), a 15 minute deprotection, five one minute NMP washes, a 60 minute coupling cycle, five NMP washes and a ninhydrin test. To a 700 mg portion of the fully assembled peptide-resin, biotin (obtained commercially from Molecular Probes, Inc.) was substituted for an FMOC-amino acid was coupled by the above protocol. The peptide was removed from the resin by treatment with trifluoroacetic acid (TFA) (82.5%), water (5%), thioanisole (5%), phenol (5%), ethanedithiol (2.5%) for two hours followed by precipitation of the peptide in cold ether. The solid was pelleted by centrifugation (2400 rpm×10 min.), and the ether decanted. It was resuspended in ether, pelleted and decanted a second time. The solid was dissolved in 10% acetic acid and lyophilized to dryness to yield 230 mg of crude biotinylated peptide. 60 mg of the solid was dissolved in 25% acetonitrile (ACN)/0.1% TFA and applied to a C18 reversed phase high performance liquid chromatography (HPLC) column. Biotinyl $\beta$-$AP_{1-40}$ was eluted using a linear gradient of 30–45% acetonitrile/0.1% TFA over 40 minutes. One primary fraction (4 mg) and several side fractions were isolated. The main fraction yielded a mass spectrum of 4556 (matrix-assisted laser desorption ionization-time of flight) which matches the theoretical (4555) for this peptide.

A β-amyloid modulator composed of an amino-terminally biotinylated β-amyloid peptide of the amino acid sequence:

DAEFRHDSGYEVHHQ (positions 1 to 15 of SEQ ID NO: 1) was prepared on an Advanced ChemTech Model 396 multiple peptide synthesizer using an automated protocol established by the manufacturer for 0.025 mmole scale synthesis. Double couplings were performed on all cycles using 2-(1H-benzotriazol-1-yl)-1,3,3-tetramethyluronium hexafluorophosphate (HBTU)/N,N-diisopropylethylamine (DIEA)/HOBt/ FMOC-AA in four-fold excess for 30 minutes followed by DIC/HOBt/FMOC-AA in four-fold excess for 45 minutes. The peptide was deprotected and removed from the resin by treatment with TFA/water (95%/5%) for three hours and precipitated with ether as described above. The pellet was resuspended in 10% acetic acid and lyophilized. The material was purified by a preparative HPLC using 15%–40% acetonitrile over 80 minutes on a Vydac C18 column (21× 250 mm). The main isolate eluted as a single symmetrical peak when analyzed by analytical HPLC and yielded the expected molecular weight when analyzed by electrospray mass spectrometry. Result=2052.6 (2052 theoretical).

β-amyloid modulator compounds comprising other regions of the β-AP amino acid sequence (e.g., an Aβ aggregation core domain) were similarly prepared using the synthesis methods described above. Moreover, modulators comprising other amyloidogenic peptides can be similarly prepared.

EXAMPLE 2

Inhibition of β-Amyloid Aggregation by Modulators

The ability of β-amyloid modulators to inhibit the aggregation of natural β-AP when combined with the natural β-AP was examined in a series of aggregation assays. Natural β-AP (β-$AP_{1-40}$) was obtained commercially from Bachem (Torrance, Calif.). Amino-terminally biotinylated β-AP modulators were prepared as described in Example 1.

A. Optical Density Assay

In one assay, β-AP aggregation was measured by determining the increase in turbidity of a solution of natural β-AP over time in the absence or presence of various concentrations of the modulator. Turbidity of the solution was quantitated by determining the optical density at 400 nm ($A_{400\ nm}$) of the solution over time.

The aggregation of natural β-AP in the absence of modulator was determined as follows. β-$AP_{1-40}$ was dissolved in hexafluoro isopropanol (HFIP; Aldrich Chemical Co., Inc.) at 2 mg/ml. Aliquots of the HFIP solution (87 μl) were transferred to individual 10 mm×75 mm test tubes. A stream of argon gas was passed through each tube to evaporate the HFIP. To the resulting thin film of peptide, dimethylsulfoxide (DMSO; Aldrich Chemical Co., Inc.) (25 μl) was added to dissolve the peptide. A 2 mm×7 mm TEFLONTM-coated magnetic stir bar was added to each tube. Buffer (475 μL of 100 mM NaCl, 10 mM sodium phosphate, pH 7.4) was added to the DMSO solution with stirring. The resulting mixture was stirred continuously and the optical density was monitored at 400 nm to observe the formation of insoluble peptide aggregates.

Alternatively, β-$AP_{1-40}$ was dissolved in DMSO as described above at 1.6 mM (6.9 mg/ml) and aliquots (25 μl) were added to stirred buffer (475 μl), followed by monitoring of absorbance at 400 nm.

For inhibition studies in which a β-amyloid modulator was dissolved in solution together with the natural β-AP, the modulators were dissolved in DMSO either with or without prior dissolution in HFIP. These compounds were then added to buffer with stirring, followed by addition of β-$AP_{1-40}$ in DMSO. Alternatively, HFIP solutions of modulators were combined with β-$AP_{1-40}$ in HFIP followed by evaporation and redissolution of the mixture in DMSO. Buffer was then added to the DMSO solution to initiate the assay. The amino-terminally biotinylated β-amyloid peptide modulators N-biotinyl-β-$AP_{1-40}$, and N-biotinyl-β-$AP_{1-15}$ were tested at concentrations of 1% and 5% in the natural β-$AP_{1-40}$ solution.

A representative example of the results is shown graphically in FIG. 1, which depicts the inhibition of aggregation of natural β-$AP_{1-40}$ by N-biotinyl-β-$AP_{1-40}$. In the absence of the modulator, the optical density of the natural β-AP solution showed a characteristic sigmoidal curve, with a lag time prior to aggregation (approximately 3 hours in FIG. 1) in which the $A_{400\ nm}$ was low, followed by rapid increase in the $A_{400\ nm}$, which quickly reached a plateau level, representing aggregation of the natural β amyloid peptides. In contrast, in the presence of as little as 1% of the N-biotinyl-β-$AP_{1-40}$ modulator, aggregation of the natural β amyloid peptides was markedly inhibited, indicated by an increase in the lag time, a decrease in the slope of aggregation and a decrease in the plateau level reached for the turbidity of the solution (see FIG. 1). N-biotinyl-β-$AP_{1-40}$ at a concentration of 5% similarly inhibited aggregation of the natural β amyloid peptide. Furthermore, similar results were observed when N-biotinyl-β-$AP_{1-15}$ was used as the modulator. These results demonstrate that an N-terminally biotinylated β-AP modulator can effectively inhibit the aggregation of natural β amyloid peptides, even when the natural β amyloid peptides are present at as much as a 100-fold molar excess concentration.

B. Fluorescence Assay

In a second assay, β-AP aggregation was measured using a fluorometric assay essentially as described in Levine, H. (1993) *Protein Science* 2:404–410. In this assay, the dye thioflavine T (ThT) is contacted with the β-AP solution. Association of ThT with aggregated β-AP, but not monomeric or loosely associated β-AP, gives rise to a new excitation (ex) maximum at 450 nm and an enhanced emission (em) at 482 nm, compared to the 385 nm (ex) and 445 nm (em) for the free dye. β-AP aggregation was assayed by this method as follows. Aliquots (2.9 μl) of the solutions used in the aggregation assays as described above in section A were removed from the samples and diluted in 200 μl of potassium phosphate buffer (50 mM, pH 7.0) containing thioflavin T (10 μM; obtained commercially from Aldrich Chemical Co., Inc.). Excitation was set at 450 nm and emission was measured at 482 nm. Similar to the results observed with the optical density assay described above in section A, as little as 1% of the N-biotinylated β-AP modulators was effective at inhibiting the aggregation of natural β amyloid peptides using this fluorometric assay.

C. Static Aggregation Assay

In a third assay, β-AP aggregation was measured by visualization of the peptide aggregates using SDS-polyacrylamide gel electrophoresis (SDS-PAGE). In this assay, β-AP solutions were allowed to aggregate over a period of time and then aliquots of the reaction were run on a standard SDS-PAGE gel. Typical solution conditions were 200 μM of β-$AP_{1-40}$ in PBS at 37° C. for 8 days or 200 μM β-$AP_{1-40}$ in 0.1 M sodium acetate at 37° C. for 3 days. The peptide aggregates were visualized by Coomassie blue staining of the gel or, for β-AP solutions that included a biotinylated β-AP modulator, by western blotting of a filter prepared from the gel with a streptavidin-peroxidase probe, followed by a standard peroxidase assay. The β-AP aggregates are identifiable as high molecular weight, low mobility bands on the gel, which are readily distinguishable from the low molecular weight, high mobility β-AP monomer or dimer bands.

When natural β-$AP_{1-40}$ aggregation was assayed by this method in the absence of any β amyloid modulators, high molecular weight aggregates were readily detectable on the gel. In contrast, when N-biotinyl-β-$AP_{1-40}$ modulator self-aggregation was assayed (i.e., aggregation of the N-biotinyl peptide alone, in the absence of any natural β-AP), few if any high molecular weight aggregates were observed, indicating that the ability of the modulator to self-aggregate is significantly reduced compared to natural β-AP. Finally, when aggregation of a mixture of natural β-$AP_{1-40}$ and N-biotinylated β-$AP_{1-40}$ was assayed by this method, reduced amounts of the peptide mixture associated into high molecular weight aggregates, thus demonstrating that the β amyloid modulator is effective at inhibiting the aggregation of the natural β amyloid peptides.

EXAMPLE 3

Neurotoxicity Analysis of β-Amyloid Modulators

The neurotoxicity of the β-amyloid modulators is tested in a cell-based assay using the neuronal precursor cell line PC-12, or primary neuronal cells, and the viability indicator 3,(4,4-dimethylthiazol-2-yl)2,5-diphenyl-tetrazolium bromide (MTT). (See Shearman, M. S. et al. (1994) *Proc. Natl. Acad. Sci. USA* 91:1470–1474; Hansen, M. B. et al. (1 989) *J. Immun. Methods* 119:203–210). PC-12 is a rat adrenal pheochromocytoma cell line and is available from the American Type Culture Collection, Rockville, Md. (ATCC CRL 1721). MTT (commercially available from Sigma Chemical Co. ) is a chromogenic substrate that is converted from yellow to blue in viable cells, which can be detected spectrophotometrically.

To test the neurotoxicity of a β-amyloid modulator (either alone or combined with natural β-AP), cells first are plated in 96-well plates at 7,000–10,000 cells/well and allowed to adhere by overnight culture at 37° C. Serial dilutions of freshly dissolved or "aged" modulators (either alone or combined with natural β-AP) in phosphate buffered saline (PBS) are added to the wells in triplicate and incubation is continued for two or more days. Aged modulators are prepared by incubating an aqueous solution of the modulator at 37° C. undisturbed for a prolonged period (e.g., five days or more). For the final two hours of exposure of the cells to the modulator preparation, MTT is added to the media to a final concentration of 1 mg/ml and incubation is continued at 37° C. Following the two hour incubation with MTT, the media is removed and the cells are lysed in isopropanol/0.4N HCl with agitation. An equal volume of PBS is added to each well and the absorbance of each well at 570 nm is measured to quantitate viable cells. Alternatively, MTT is solubilized by addition of 50% N,N-dimethyl formamide/20% sodium dodecyl sulfate added directly to the media in the wells and viable cells are likewise quantitated by measuring absorbance at 570 nm. The relative neurotoxicity of a β-amyloid modulator (either alone or in combination with natural β-AP) is determined by comparison to natural β-AP alone (e.g., β1-40, β1-42), which exhibits neurotoxicity in this assay and thus can serve as a positive control.

EXAMPLE 4

Syntheses of Additional Modified β-Amyloid Peptide Compounds

In this example, a series of modified β-APs, having a variety of N-terminal or random side chain modifications were synthesized.

A series of N-terminally modified β-amyloid peptides was synthesized using standard methods. Fully-protected resin-bound peptides corresponding to Aβ(1–15) and Aβ(1-40) were prepared as described in Example 1 on Wang resin to eventually afford carboxyl terminal peptide acids. Small portions of each peptide resin (13 and 20 μmoles, respectively) were aliquoted into the wells of the reaction block of an Advanced ChemTech Model 396 Multiple Peptide Synthesizer. The N-terminal FMOC protecting group of each sample was removed in the standard manner with 25% piperidine in NMP followed by extensive washing with NMP. The unprotected N-terminal α-amino group of each peptide-resin sample was modified using one of the following methods:

Method A, coupling of modifying reagents containing free carboxylic acid groups: The modifying reagent (five equivalents) was predissolved in NMP, DMSO or a mixture of these two solvents. HOBT and DIC (five equivalents of each reagent) were added to the dissolved modifier and the resulting solution was added to one equivalent of free-amino peptide-resin. Coupling was allowed to proceed overnight, followed by washing. If a ninhydrin test on a small sample of peptide-resin showed that coupling was not complete, the coupling was repeated using 1-hydroxy-7-azabenzotriazole (HOAt) in place of HOBt.

Method B, coupling of modifying reagents obtained in preactivated forms: The modifying reagent (five equivalents) was predissolved in NMP, DMSO or a mixture of these two solvents and added to one equivalent of peptide-resin. Diisopropylethylamine (DIEA; six equivalents) was added to the suspension of activated modifier and peptide-resin. Coupling was allowed to proceed overnight, followed by washing. If a ninhydrin test on a small sample of peptide-resin showed that coupling was not complete, the coupling was repeated.

After the second coupling (if required) the N-terminally modified peptide-resins were dried at reduced pressure and cleaved from the resin with removal of side-chain protecting groups as described in Example 1. Analytical reversed-phase HPLC was used to confirm that a major product was present in the resulting crude peptides which were purified using Millipore Sep-Pak cartridges or preparative reverse-phase HPLC. Mass spectrometry was used to confirm the presence of the desired compound in the product.

Method A was used to couple N-acetylneuraminic acid, cholic acid, trans-4-cotininecarboxylic acid, 2-imino-1-imidazolidineacetic acid, (S)-(–)-indoline-2-carboxylic acid, (–)-menthoxyacetic acid, 2-norbornaneacetic acid, γ-oxo-5-acenaphthenebutyric acid, (–)-2-oxo-4-thiazolidinecarboxylic acid, and tetrahydro-3-furoic acid. Method B was used to couple 2-iminobiotin-N-hydroxysuccinimide ester, diethylenetriaminepentaacetic dianhydride, 4-morpholinecarbonyl chloride, 2-thiopheneacetyl chloride, and 2-thiophenesulfonyl chloride.

In a manner similar to the construction of N-terminally modified Aβ(1–15) and Aβ(1-40) peptides described above, N-fluoresceinyl Aβ(1–15) and Aβ(1-40) were prepared in two alternative manners using the preactivated reagents 5-(and 6)-carboxyfluorescein succinimidyl ester and fluorescein-5-isothiocyanate (FITC Isomer I). Both reagents were obtained from Molecular Probes Inc. Couplings were performed using four equivalents of reagent per equivalent of peptide-resin with DIEA added to make the reaction solution basic to wet pH paper. Couplings of each reagent to Aβ(1-15)-resin appeared to be complete after a single overnight coupling. Coupling to Aβ(1-40)-resin was slower as indicated by a positive ninhydrin test and both reagents were recoupled to this peptide-resin overnight in tetrahydrofuran-NMP (1:2 v/v). The resulting N-terminally modified peptide-resins were cleaved, deprotected and purified as described in Example A.

In addition to the N-fluoresceinyl Aβ peptides described above, a β-amyloid modulator comprised of random modification of Aβ(1-40) with fluorescein was prepared. Aβ(1-40) purchased from Bachem was dissolved in DMSO at approximately 2 mg/mL. 5-(and-6)-Carboxyfluorescein purchased from Molecular Probes was added in a 1.5 molar excess and DIEA was added to make the solution basic to wet pH paper. The reaction was allowed to proceed for 1 hour at room temperature and was then quenched with triethanolamine. The product was added to assays as this crude mixture.

β-amyloid modulator compounds comprising other regions of the β-AP amino acid sequence (e.g., an Aβ aggregation core domain) were similarly prepared using the synthesis methods described above. Moreover, modulators comprising other amyloidogenic peptides can be similarly prepared.

EXAMPLE 5

Identification of Additional β-Amyloid Modulators

In this Example, two assays of Aβ aggregation were used to identify β-amyloid modulators which can inhibit this process.

The first assay is referred to as a seeded static assay (SSA) and was performed as follows:

To prepare a solution of Aβ monomer, the appropriate quantity of Aβ(1-40) peptide (Bachem) was weighed out on a micro-balance (the amount was corrected for the amount of water in the preparation, which, depending on lot number, was 20–30% w/w). The peptide was dissolved in $\frac{1}{25}$ volume of dimethysulfoxide (DMSO), followed by water to $\frac{1}{2}$ volume and $\frac{1}{2}$ volume 2×PBS (10×PBS: NaCl 137 mM, KCl 2.7 mM $Na_2HPO_4 \cdot 7H_2O$ 4.3 mM, $KH_2PO_4$ 1.4 mM pH 7.2) to a final concentration of 200 μM.

To prepare a stock seed, 1 ml of the above Aβ monomer preparation, was incubated for 8 days at 37° C. and sheared sequentially through an 18, 23, 26 and 30 gauge needle 25, 25, 50, and 100 times respectively. 2 μl samples of the sheared material was taken for fluorescence measurements after every 50 passes through the 30 gauge needle until the fluorescence units (FU) had plateaued (approx. 100–150×).

To prepare a candidate inhibitor, the required amount of candidate inhibitor was weighed out and the stock dissolved in 1×PBS to a final concentration of 1 mM (10×stock). If insoluble, it was dissolved in $\frac{1}{10}$ volume of DMSO and diluted in 1×PBS to 1 mM. A further $\frac{1}{10}$ dilution was also prepared to test each candidate at both 100 μM and 10 μM.

For the aggregation assay, each sample was set up in triplicate [50 μl of 200 μM monomer, 125 FU sheared seed (variable quantity dependent on the batch of seed, routinely 3–6 μl), 10 μl of 10× inhibitor solution, final volume made up to 100 μl with 1×PBS]. Two concentrations of each inhibitor were tested 100 μM and 10 μM, equivalent to a 1:1 and a 1:10 molar ratio of monomer to inhibitor. The controls included an unseeded reaction to confirm that the fresh monomer contained no seed, and a seeded reaction in the absence of inhibitor, as a reference to compare against putative inhibitors. The assay was incubated at 37° C. for 6 h, taking 2 μl samples hourly for fluorescence measurements. To measure fluorescence, a 2 μl sample of Aβ was added to 400 μl of Thioflavin-T solution (50 mM Potassium Phosphate 10 mM Thioflavin-T pH 7.5). The samples were vortexed and the fluorescence was read in a 0.5 ml micro quartz cuvette at EX 450 nm and EM 482 nm (Hitachi 4500 Fluorimeter). β-aggregation results in enhanced emission of Thioflavin-T. Accordingly, samples including an effective inhibitor compound exhibit reduced emission as compared to control samples without the inhibitor compound.

The second assay is referred to as a shaken plate aggregation assay and was performed as follows:

Aβ(1-40) peptide from Bachem (Torrance, Calif.) was dissolved in HFIP (1,1,1,3,3,3-Hexafluoro-2-propanol; Aldrich 10,522-8) at a concentration of 2 mg peptide/ml and incubated at room temperature for 30 min. HFIP solubilized peptide was sonicated in a waterbath sonicator for 5 min at highest setting, then evaporated to dryness under a stream of argon. The peptide film was resuspended in anhydrous dimethylsulfoxide (DMSO) at a concentration of 6.9 mg/ml, sonicated for 5 min as before, then filtered through a 0.2 micron nylon syringe filter (VWR cat. No. 28196-050). Candidate inhibitors were dissolved directly in DMSO, generally at a molar concentration 4 times that of the Aβ(1-40) peptide.

Candidates were assayed in triplicate. For each candidate to be tested, 4 parts Aβ(1-40) peptide in DMSO were combined with 1 part candidate inhibitor in DMSO in a glass vial, and mixed to produce a 1:1 molar ratio of Aβ peptide to candidate. For different molar ratios, candidates were diluted with DMSO prior to addition to A(I 1-40), in order to keep the final DMSO and Aβ(1-40) concentrations constant. Into an ultra low binding 96 well plate (Corning Costar cat. No. 2500, Cambridge Mass.) 100 μl PTL buffer (150 mM NaCl, 10 mM $NaH_2PO_4$; pH 7.4) was aliquotted per well. For each candidate, 10 μl of peptide mixture in DMSO was aliquotted into each of three wells containing buffer. The covered plate was vigorously vortexed on a plate shaker at high speed for 30 seconds. An additional 100 μl of PTL buffer was added to each well and again the plate was vortexed vigorously for 30 sec. Absorbance at 405 nm was immediately read in a plate reader for a baseline reading. The plate was returned to the plate shaker and vortexed at moderate speed for 5 hours at room temperature, with absorbance readings taken at 15–20 min intervals. Increased absorbance indicated aggregation. Accordingly, effective inhibitor compounds cause a decrease in absorbance in the test sample as compared to a control sample without the inhibitor compound.

Representative results of the static seeded assay and shaken plate assay with preferred β-amyloid modulators are shown below in Table I.

TABLE I

| Candidate Inhibitor | Aβ Amino Acids | Modifying Reagent | Effect in shaken plate assay | Effect in Seeded Static Assay* |
|---|---|---|---|---|
| 174 | Aβ1–15 | Cholic acid | Complete inhibition at 100% conc | ++ |
| 176 | Aβ1–15 | Diethylene-triamine penta acetic acid | Decreased Plateau | ++ |
| 180 | Aβ1–15 | (−)-Menthoxy acetic acid | None | ++ |
| 190 | Aβ1–15 | Fluorescein carboxylic acid (FICO) | Decreased Plateau | ++ |
| 220 | Aβ16–40 mutant | $NH_2$-EEVVHHHHQQ-[Aβ(16–40)]-COOH (SEQ. ID NO:16) | Complete inhibition at 100%, increased lag at 10% | ++ |
| 224 | Aβ1–40 mutant | $F_{19}F_{20}->T_{19}T_{20}$ | Increased lag | ++ |

TABLE I-continued

| Candidate Inhibitor | Aβ Amino Acids | Modifying Reagent | Effect in shaken plate assay | Effect in Seeded Static Assay* |
|---|---|---|---|---|
| 233 | A6β–20 | Acetic acid | accelerated aggregation at 10% conc | ++ |

*++ = A strong inhibitor of aggregation. The rate of aggregation in the presence of the inhibitor was decreased compared to the control by at least 30–50%

These results indicate that β-APs modified by a wide variety of N-terminal modifying groups are effective at modulating β-amyloid aggregation.

EXAMPLE 6

Additional β-Amyloid Aggregation Assays

Most preferably, the ability of β-amyloid modulator compounds to modulate (e.g., inhibit or promote) the aggregation of natural β-AP when combined with the natural β-AP is examined in one or both of the aggregation assays described below. Natural W-AP (β-$AP_{1-40}$) for use in the aggregation assays is commercially available from Bachem (Torrance, Calif.).

A. Nucleation Assay

The nucleation assay is employed to determine the ability of test compounds to alter (e.g., inhibit) the early events in formation of β-AP fibers from monomeric β-AP. Characteristic of a nucleated polymerization mechanism, a lag time is observed prior to nucleation, after which the peptide rapidly forms fibers as reflected in a linear rise in turbidity. The time delay before polymerization of β-AP monomer can be quantified as well as the extent of formation of insoluble fiber by light scattering (turbidity). Polymerization reaches equilibrium when the maximum turbidity reaches a plateau. The turbidity of a solution of natural β-AP in the absence or presence of various concentrations of a β-amyloid modulator compound is determined by measuring the apparent absorbance of the solution at 405 nm ($A_{405\ nm}$) over time. The threshold of sensitivity for the measurement of turbidity is in the range of 15–20 μM β-AP. A decrease in turbidity over time in the presence of the modulator, as compared to the turbidity in the absence of the modulator, indicates that the modulator inhibits formation of β-AP fibers from monomeric β-AP. This assay can be performed using stirring or shaking to accelerate polymerization, thereby increasing the speed of the assay. Moreover the assay can be adapted to a 96-well plate format to screen multiple compounds.

To perform the nucleation assay, first $Aβ_{1-40}$ peptide is dissolved in HFIP (1,1,1,3,3,3-Hexafluoro-2-propanol; Aldrich 10,522-8) at a concentration of 2 mg peptide/ml and incubated at room temperature for 30 min. HFIP-solubilized peptide is sonicated in a waterbath sonicator for 5 min at highest setting, then evaporated to dryness under a stream of argon. The peptide film is resuspended in anhydrous dimethylsulfoxide (DMSO) at a concentration of 6.9 mg/ml (25×concentration), sonicated for 5 min as before, then filtered through a 0.2 micron nylon syringe filter (VWR cat. No. 28196-050). Test compounds are dissolved in DMSO at a 100×concentration. Four volumes of 25×$Aβ_{1-40}$ peptide in DMSO are combined with one volume of test compound in DMSO in a glass vial, and mixed to produce a 1:1 molar ratio of Aβ peptide to test compound. For different molar ratios, test compounds are diluted with DMSO prior to addition to $Aβ_{1-40}$, in order to keep the final DMSO and $Aβ_{1-40}$ concentrations constant. Control samples do not contain the test compound. Ten microliters of the mixture is then added to the bottom of a well of a Corning Costar ultra low binding 96-well plate (Corning Costar, Cambridge Mass.; cat. No. 2500). Ninety microliters of water is added to the well, the plate is shaken on a rotary shaken at a constant speed at room temperature for 30 seconds, an additional 100 μl of 2×PTL buffer (20 mM $NaH_2PO_4$, 300 mM NaCl, pH 7.4) is added to the well, the plate is reshaken for 30 seconds and a baseline (t=0) turbidity reading is taken by measuring the apparent absorbance at 405 nm using a Bio-Rad Model 450 Microplate Reader. The plate is then returned to the shaker and shaken continuously for 5 hours. Turbidity readings are taken at 15 minute intervals.

β-amyloid aggregation in the absence of any modulators results in enhanced turbidity of the natural β-AP solution (i.e., an increase in the apparent absorbance at 405 nm over time). Accordingly, a solution including an effective inhibitory modulator compound exhibits reduced turbidity as compared to the control sample without the modulator compound (i.e., less apparent absorbance at 405 nm over time as compared to the control sample).

B. Seeded Extension Assay

The seeded extension assay can be employed to measure the rate of Aβ fiber formed n a solution of Aβ monomer following addition of polymeric Aβ fiber "seed". The ability of est compounds to prevent further deposition of monomeric Aβ to previously deposited amyloid is determined using a direct indicator of β-sheet formation using fluorescence. In contrast with the nucleation assay, the addition of seed provides immediate nucleation and continued growth of preformed fibrils without the need for continuous mixing, and thus results in the absence of a lag time before polymerization starts. Since this assay uses static polymerization conditions, the activity of positive compounds in the nucleation assay can be confirmed in this second assay under different conditions and with an additional probe of amyloid structure.

In the seeded extension assay, monomeric $Aβ_{1-40}$ is incubated in the presence of a "seed" nucleus (approximately ten mole percent of Aβ that has been previously allowed to polymerize under controlled static conditions). Samples of the solution are then diluted in thioflavin T (Th-T). The polymer-specific association of Th-T with Aβ produces a fluorescent complex that allows the measurement of the extent of fibril formation (Levine, H. (1993) *Protein Science* 2:404–410). In particular, association of Th-T with aggregated β-AP, but not monomeric or loosely associated β-AP, gives rise to a new excitation (ex) maximum at 450 nm and an enhanced emission (em) at 482 nm, compared to the 385 nm (ex) and 445 nm (em) for the free dye. Small aliquots of the polymerization mixture contain sufficient fibril to be mixed with Th-T to allow the monitoring of the reaction mixture by repeated sampling. A linear growth curve is observed in the presence of excess monomer. The formation of thioflavin T responsive β-sheet fibrils parallels the increase in turbidity observed using the nucleation assay.

A solution of Aβ monomer for use in the seeded extension assay is prepared by dissolving an appropriate quantity of $Aβ_{1-40}$ peptide in 1/25 volume of dimethylsulfoxide (DMSO), followed by water to 1/2 volume and 1/2 volume 2x PBS (10×PBS: NaCl 137 mM, KCl 2.7 mM $Na_2HPO_4.7H_2O$.4.3 mM, $KH_2PO_4$ 1.4 mM pH 7.2) to a final concentration of 200 μM. To prepare the stock seed, 1 ml of the Aβ monomer preparation, is incubated for approximately 8 days at 37° C.

and sheared sequentially through an 18, 23, 26 and 30 gauge needle 25, 25, 50, and 100 times respectively. 2 μl samples of the sheared material is taken for fluorescence measurements after every 50 passes through the 30 gauge needle until the fluorescence units (FU) plateau (approx. 100–150×). Test compounds are prepared by dissolving an appropriate amount of test compound in 1×PBS to a final concentration of 1 mM (10×stock). If insoluble, the compound is dissolved in 1/10 volume of DMSO and diluted in 1×PBS to 1 mM. A further 1/10 dilution is also prepared to test each candidate at both 100 μM and 10 μM.

To perform the seeded extension assay, each sample is set up with 50 μl of 200 μM monomer, 125 FU sheared seed (a variable quantity dependent on the batch of seed, routinely 3–6 μl) and 10 μl of 10×modulator solution. The sample volume is then adjusted to a final volume of 100 μl with 1×PBS. Two concentrations of each modulator typically are tested: 100 μM and 10 μM, equivalent to a 1:1 and a 1:10 molar ratio of monomer to modulator. The controls include an unseeded reaction to confirm that the fresh monomer contains no seed, and a seeded reaction in the absence of any modulators, as a reference to compare against candidate modulators. The assay is incubated at 37° C. for 6 h, taking 2 μl samples hourly for fluorescence measurements. To measure fluorescence, a 2 μl sample of Aβ is added to 400 μl of Thioflavin-T solution (50 mM Potassium Phosphate 10 mM Thioflavin-T pH 7.5). The samples are vortexed and the fluorescence is read in a 0.5 ml micro quartz cuvette at EX 450 nm and EM 482 nm (Hitachi 4500 Fluorimeter).

β-amyloid aggregation results in enhanced emission of Thioflavin-T. Accordingly, samples including an effective inhibitory modulator compound exhibit reduced emission as compared to control samples without the modulator compound.

EXAMPLE 7
Effect of Different Amino Acid Subregions of Aβ Peptide on the Inhibitory Activity of β-Amyloid Modulator Compounds To determine the effect of various subregions of $A\beta_{1-40}$ on the inhibitory activity of a a β-amyloid modulator, overlapping Aβ peptide 15 mers were constructed. For each 15 mer, four different amino-terminal modifiers were tested: a cholyl group, an iminobiotinyl group, an N-acetyl neuraminyl group (NANA) and a 5-(and 6-)-carboxyfluoresceinyl group (FICO). The modulators were evaluated in the nucleation and seeded extension assays described in Example 6.

The results of the nucleation assays are summarized below in Table II. The concentration of $A\beta_{1-40}$ used in the assays was 50 μM. The "mole %" value listed in Table II refers to the % concentration of the test compound relative to $A\beta_{1-40}$. Accordingly, 100% indicates that $A\beta_{1-40}$ and the test compound were equimolar. Mole % values less than 100% indicate that $A\beta_{1-40}$ was in molar excess relative to the test compound (e.g., 10% indicates that $A\beta_{1-40}$ was in 10-fold molar excess relative to the test compound). The results of the nucleation assays for each test compound are presented in Table II in two ways. The "fold increase in lag time", which is a measure of the ability of the compound to delay the onset of aggregation, refers to the ratio of the observed lag time in the presence of the test compound to the observed lag time in the control without the test compound. Accordingly a fold increase in lag time of 1.0 indicates no change in lag time, whereas numbers>1.0 indicate an increase in lag time. The "% inhibition of plateau", which is a measure of the ability of the compound to decrease the total amount of aggregation, refers to the reduction of the final turbidity in the presence of the test compound expressed as a percent of the control without the test compound. Accordingly, an inhibitor that abolishes aggregation during the course of the assay will have a % inhibition of 100. N-terminally modified β subregions which exhibited inhibitory activity are indicated in bold in Table II.

TABLE II

| Reference # | N-terminal Modification | Aβ Peptide | Mole % | Fold Increase in Lag Time | % Inhibition of Plateau |
|---|---|---|---|---|---|
| PPI-174 | cholyl | $A\beta_{1-15}$ | 100 | >4.5 | 100 |
| PPI-264 | cholyl | $A\beta_{6-20}$ | 100 | >4.5 | 100 |
| PPI-269 | cholyl | $A\beta_{11-25}$ | 100 | 1.5 | ~0 |
| PPI-274 | cholyl | $A\beta_{16-30}$ | 100 | >4.5 | 100 |
| PPI-279 | cholyl | $A\beta_{21-35}$ | 100 | 1.6 | 51 |
| PPI-284 | cholyl | $A\beta_{26-40}$ | 100 | >4.5 | 87 |
| PPI-173 | NANA | $A\beta_{1-15}$ | 100 | ~1 | ~0 |
| PPI-266 | NANA | $A\beta_{6-20}$ | 100 | 1.3 | 64 |
| PPI-271 | NANA | $A\beta_{11-25}$ | 100 | 1.3 | 77 |
| PPI-276 | NANA | $A\beta_{16-30}$ | 100 | ~1 | ~0 |
| PPI-281 | NANA | $A\beta_{21-35}$ | 100 | ~1 | 53 |
| PPI-286 | NANA | $A\beta_{26-40}$ | 100 | 1.3 | ~0 |
| PPI-172 | Iminobiotinyl | $A\beta_{1-15}$ | 100 | 1.2 | ~0 |
| PPI-267 | Iminobiotinyl | $A\beta_{6-20}$ | 100 | 1.6 | 44 |
| PPI-272 | Iminobiotinyl | $A\beta_{11-25}$ | 100 | 1.2 | 40 |
| PPI-277 | Iminobiotinyl | $A\beta_{16-30}$ | 100 | 1.2 | 55 |
| PPI-282 | Iminobiotinyl | $A\beta_{21-35}$ | 100 | ~1 | 66 |
| PPI-287 | Iminobiotinyl | $A\beta_{26-40}$ | 100 | 2.3 | ~0 |
| PPI-190 | FICO | $A\beta_{1-15}$ | 100 | ~1 | 30 |
| PPI-268 | FICO | $A\beta_{6-20}$ | 100 | 1.9 | ~0 |
| PPI-273 | FICO | $A\beta_{11-25}$ | 100 | 1.7 | 34 |
| PPI-278 | FICO | $A\beta_{16-30}$ | 100 | 1.6 | 59 |
| PPI-283 | FICO | $A\beta_{21-35}$ | 100 | 1.2 | 25 |
| PPI-288 | FICO | $A\beta_{26-40}$ | 100 | 2 | 75 |

These results indicate that certain subregions of $A\beta_{1-40}$, when modified with an appropriate modifying group, are effective at inhibiting the aggregation of $A\beta_{1-40}$. A cholyl group was an effective modifying group for several subregions. Cholic acid alone was tested for inhibitory activity but had no effect on Aβ aggregation. The Aβ$_{6-20}$ subregion exhibited high levels of inhibitory activity when modified with several different modifying groups (cholyl, NANA, iminobiotinyl), with cholyl-Aβ$_{6-20}$ (PPI-264) being the most active form. Accordingly, this modulator compound was chosen for further analysis, described in Example 8.

EXAMPLE 8

Identification of a Five Amino Acid Subregion of Aβ Peptide Sufficient for Inhibitory Activity of a β-Amyloid Modulator Compound To further delineate a minimal subregion of cholyl-Aβ$_{6-20}$ sufficient for inhibitory activity, a series of amino terminal and carboxy terminal amino acid deletions of cholyl-Aβ$_{6-20}$ were constructed. The modulators all had the same cholyl amino-terminal modification. Additionally, for the peptide series having carboxy terminal deletions, the carboxy terminus was further modified to an amide. The modulators were evaluated as described in Example 7 and the results are summarized below in Table III, wherein the data is presented as described in Example 7.

which inhibitory activity is restored. Furthermore, additional deletion of amino acid position 14 (i. e., cholyl-Aβ$_{15-20}$) or positions 14 and 15 (i. e., cholyl-Aβ$_{16-20}$) still maintained inhibitory activity. Thus, amino terminal deletions of Aβ$_{6-20}$ identified Aβ$_{16-20}$ as a minimal subregion which is sufficient for inhibitory activity when appropriately modified. In contrast, carboxy terminal deletion of amino acid position 20 resulted in loss of activity which was not fully restored as the peptide was deleted further at the carboxy-terminal end. Thus, maintenance of position 20 within the modulator may be important for inhibitory activity.

EXAMPLE 9

Identification of a Four Amino Acid Subregion of Aβ Peptide Sufficient for Inhibitory Activity of a β-Amyloid Modulator Compound In this example, the smallest effective modulator identified in the studies described in Example 8, cholyl-Aβ$_{16-20}$ (PPI-350), was analyzed further. Additional amino- and carboxy-terminal deletions were made with cholyl-Aβ$_{16-20}$, as well as an amino acid substitution (Val$_{18}$→Thr), to

TABLE III

| Ref. # | N-Term. Mod. | Aβ Peptide | C-Term. Mod. | Mole % | Fold Increase in Lag Time | % Inhibition of Plateau |
|---|---|---|---|---|---|---|
| PPI-264 | cholyl | Aβ$_{6-20}$ | — | 100 | >4.5 | 100 |
|  |  |  |  | 10 | 2 | 43 |
| PPI-341 | cholyl | Aβ$_{7-20}$ | — | 100 | >4.5 | 100 |
|  |  |  |  | 33 | 2 | ~0 |
| PPI-342 | cholyl | Aβ$_{8-20}$ | — | 100 | 1.5 | ~0 |
|  |  |  |  | 33 | 2.1 | ~0 |
| PPI-343 | cholyl | Aβ$_{9-20}$ | — | 33 | 2.0 | ~0 |
| PPI-344 | cholyl | Aβ$_{10-20}$ | — | 33 | 2.1 | ~0 |
| PPI-345 | cholyl | Aβ$_{11-20}$ | — | 33 | 1.5 | ~0 |
| PPI-346 | cholyl | Aβ$_{12-20}$ | — | 33 | 2.1 | ~0 |
| PPI-347 | cholyl | Aβ$_{13-20}$ | — | 33 | 2.6 | ~0 |
| PPI-348 | cholyl | Aβ$_{14-20}$ | — | 33 | 2.0 | 49 |
| PPI-349 | cholyl | Aβ$_{15-20}$ | — | 33 | 2.3 | 50 |
| PPI-350 | cholyl | Aβ$_{16-20}$ | — | 38 | 3.4 | 23 |
| PPI-296 | cholyl | Aβ$_{6-20}$ | amide | 33 | 1.8 | ~0 |
| PPI-321 | cholyl | Aβ$_{6-19}$ | amide | 33 | 1.4 | ~0 |
| PPI-325 | cholyl | Aβ$_{6-17}$ | amide | 33 | 1.8 | ~0 |
| PPI-331 | cholyl | Aβ$_{6-14}$ | amide | 33 | 1.0 | 29 |
| PPI-339 | cholyl | Aβ$_{6-10}$ | amide | 33 | 1.1 | 13 |

These results indicate that activity of the modulator is maintained when amino acid residue 6 is removed from the amino terminal end of the modulator (i.e., cholyl-Aβ$_{7-20}$ retained activity) but activity is lost as the peptide is deleted further at the amino-terminal end by removal of amino acid position 7 through to amino acid position 12 (i.e., cholyl-Aβ$_{8-20}$ through cholyl-Aβ$_{13-20}$ did inhibit the plateau level of Aβ aggregation). However, further deletion of amino acid position 13 resulted in a compound (i.e., cholyl-Aβ$_{4-20}$) in identify the smallest region sufficient for the inhibitory activity of the modulator. A peptide comprised of five alanine residues, (Ala)$_5$; SEQ ID NO: 35, modified at its amino-terminus with cholic acid, was used as a specificity control. The modulators were evaluated as described in Example 7 and the results are summarized below in Table IV, wherein the data is presented as described in Example 7.

TABLE IV

| Ref. # | N-Term. Mod. | Aβ Peptide | C-Term. Mod. | Mole % | Fold Increase in Lag Time | % Inhibition of Plateau |
|---|---|---|---|---|---|---|
| PPI-264 | cholyl | Aβ$_{6-20}$ | — | 10 | 2.0 | 43 |
| PPI-347 | cholyl | Aβ$_{13-20}$ | — | 10 | 2.2 | 57 |
| PPI-349 | cholyl | Aβ$_{15-20}$ | — | 100 | >5.0 | 100 |
|  |  |  |  | 33 | 2.6 | 35 |
|  |  |  |  | 10 | 2.1 | ~0 |
| PPI-350 | cholyl | Aβ$_{16-20}$ | — | 100 | >5.0 | 100 |
|  |  |  |  | 10 | 2.4 | 40 |

TABLE IV-continued

| Ref. # | N-Term. Mod. | Aβ Peptide | C-Term. Mod. | Mole % | Fold Increase in Lag Time | % Inhibition of Plateau |
|---|---|---|---|---|---|---|
| PPI-368 | cholyl | $A\beta_{17-21}$ | — | 100 | >5.0 | 100 |
| PPI-374 | imino-biotinyl | $A\beta_{16-20}$ | — | 100 | 1.3 | 86 |
| PPI-366 | cholyl | $A\beta_{15-19}$ | — | 100 | 3.1 | ~0 |
|  |  |  |  | 10 | 1.6 | ~0 |
| PPI-369 | cholyl | $A\beta_{16-20}$ ($Val_{18}$->Thr) | — | 100 | ~1 | ~0 |
| PPI-370 | cholyl | $A\beta_{16-20}$ ($Phe_{19}$->Ala) | — | 100 | 2.6 | 73 |
| PPI-365 | cholyl | $(Ala)_5$(SEQIDNO:35) | — | 100 | ~1 | ~0 |
| PPI-319 | cholyl | $A\beta_{16-20}$ | amide | 33 | 5.6 | ~0 |
|  |  |  |  | 10 | 2.7 | ~0 |
| PPI-321 | cholyl | $A\beta_{16-19}$ | amide | 100 | 1.2 | ~0 |
| PPI-377 | — | $A\beta_{16-20}$ | — | 100 | ~1 | ~0 |

As shown in Table IV, cholyl-$A\beta_{16-20}$ (PPI-350) and cholyl-$AP]_{7-21}$ (PPI-368) both exhibited inhibitory activity, indicating that the four-amino acid minimal subregion of positions 17–20 is sufficient for inhibitory activity. Loss of position 20 (e.g., in PPI-366 and PPI-321) resulted in loss of inhibitory activity, demonstrating the importance of position 20. Moreover, mutation of valine at position 18 to threonine (in PPI-369) also resulted in loss of activity, demonstrating the importance of position 18. In contrast, mutation of phenylalanine at position 19 to alanine (cholyl-$A\beta_{16-20}$ $Phe_{19} \rightarrow Ala$; PPI-370) resulted in a compound which still retained detectable inhibitory activity. Accordingly, the phenylalanine at position 19 is more amenable to substitution, preferably with another hydrophobic amino acid residue. Cholyl-penta-alanine; SEQ ID NO: 35 (PPI-365) showed no inhibitory activity, demonstrating the specificity of the Aβ peptide portion of the modulator. Moreover, unmodified $A\beta_{16-20}$ (PPI-377) was not inhibitory, demonstrating the functional importance of the amino-terminal modifying group. The specific functional group influenced the activity of the modulator. For example, iminobiotinyl-$A\beta_{16-20}$ (PPI-374) exhibited inhibitory activity similar to cholyl-$A\beta_{16-20}$, whereas an N-acetyl neuraminic acid (NANA)-modified $A\beta_{16-20}$ was not an effective inhibitory modulator (not listed in Table IV). A C-terminal amide derivative of cholyl-$A\beta_{16-20}$ (PPI-319) retained high activity in delaying the lag time of aggregation, indicating that the carboxy-terminus of the modulator can be derivatized without loss of inhibitory activity. Although this amide-derivatized compound did not inhibit the overall plateau level of aggregation over time, the compound was not tested at concentrations higher than mole 33% Higher concentrations of the amide-derivatized compound are predicted to inhibit the overall plateau level of aggregation, similar to cholyl-$A\beta_{16-20}$ (PPI-350).

EXAMPLE 10

Effect of β-Amyloid Modulators on the Neurotoxicity of Natural β-Amyloid Peptide Aggregates The neurotoxicity of natural β-amyloid peptide aggregates, in either the presence or absence of a β-amyloid modulator, is tested in a cell-based assay using either a rat or human neuronally-derived cell line (PC-12 cells or NT-2 cells, respectively) and the viability indicator 3,(4,4-dimethylthiazol-2-yl)2,5-diphenyl-tetrazolium bromide (MTT). (See e.g., Shearman, M. S. et al. (1994) *Proc. Natl. Acad. Sci. USA* 91:1470–1474; Hansen, M. B. et al. (1989) *J. Immun. Methods* 119:203–210 for a description of similar cell-based viability assays). PC-12 is a rat adrenal pheochromocytoma cell line and is available from the American Type Culture Collection, Rockville, Md. (ATCC CRL 1721). MTT (commercially available from Sigma Chemical Co.) is a chromogenic substrate that is converted from yellow to blue in viable cells, which can be detected spectrophotometrically.

To test the neurotoxicity of natural β-amyloid peptides, stock solutions of fresh Aβ monomers and aged Aβ aggregates were first prepared. $A\beta_{1-40}$ in 100% DMSO was prepared from lyophilized powder and immediately diluted in one half the final volume in $H_2O$ and then one half the final volume in 2×PBS so that a final concentration of 200 μM peptide, 4% DMSO is achieved. Peptide prepared in this way and tested immediately on cells is referred to as "fresh" Aβ monomer. To prepare "aged" Aβ aggregates, peptide solution was placed in a 1.5 ml Eppendorf tube and incubated at 37° C. for eight days to allow fibrils to form. Such "aged" Aβ peptide can be tested directly on cells or frozen at −80° C. The neurotoxicity of fresh monomers and aged aggregates were tested using PC12 and NT2 cells. PC12 cells were routinely cultured in Dulbeco's modified Eagle's medium (DMEM) containing 10% horse serum, 5% fetal calf serum, 4 mM glutamine, and 1% gentamycin. NT2 cells were routinely cultured in OPTI-MEM medium (GIBCO BRL CAT. #31985) supplemented with 10% fetal calf serum, 2 mM glutamine and 1% gentamycin. Cells were plated at 10–15,000 cells per well in 90 μl of fresh medium in a 96-well tissue culture plate 3–4 hours prior to treatment. The fresh or aged Aβ peptide solutions (10 μL) were then diluted 1:10 directly into tissue culture medium so that the final concentration was in the range of 1–10 μM peptide. Cells are incubated in the presence of peptide without a change in media for 48 hours at 37° C. For the final three hours of exposure of the cells to the β-AP preparation, MTT was added to the media to a final concentration of 1 mg/ml and incubation was continued at 37° C. Following the two hour incubation with MTT, the media was removed and the cells were lysed in 100 μL isopropanol/0.4N HCl with agitation. An equal volume of PBS was added to each well and the plates were agitated for an additional 10 minutes. Absorbance of each well at 570 nm was measured using a microtiter plate reader to quantitate viable cells.

Figure 3:
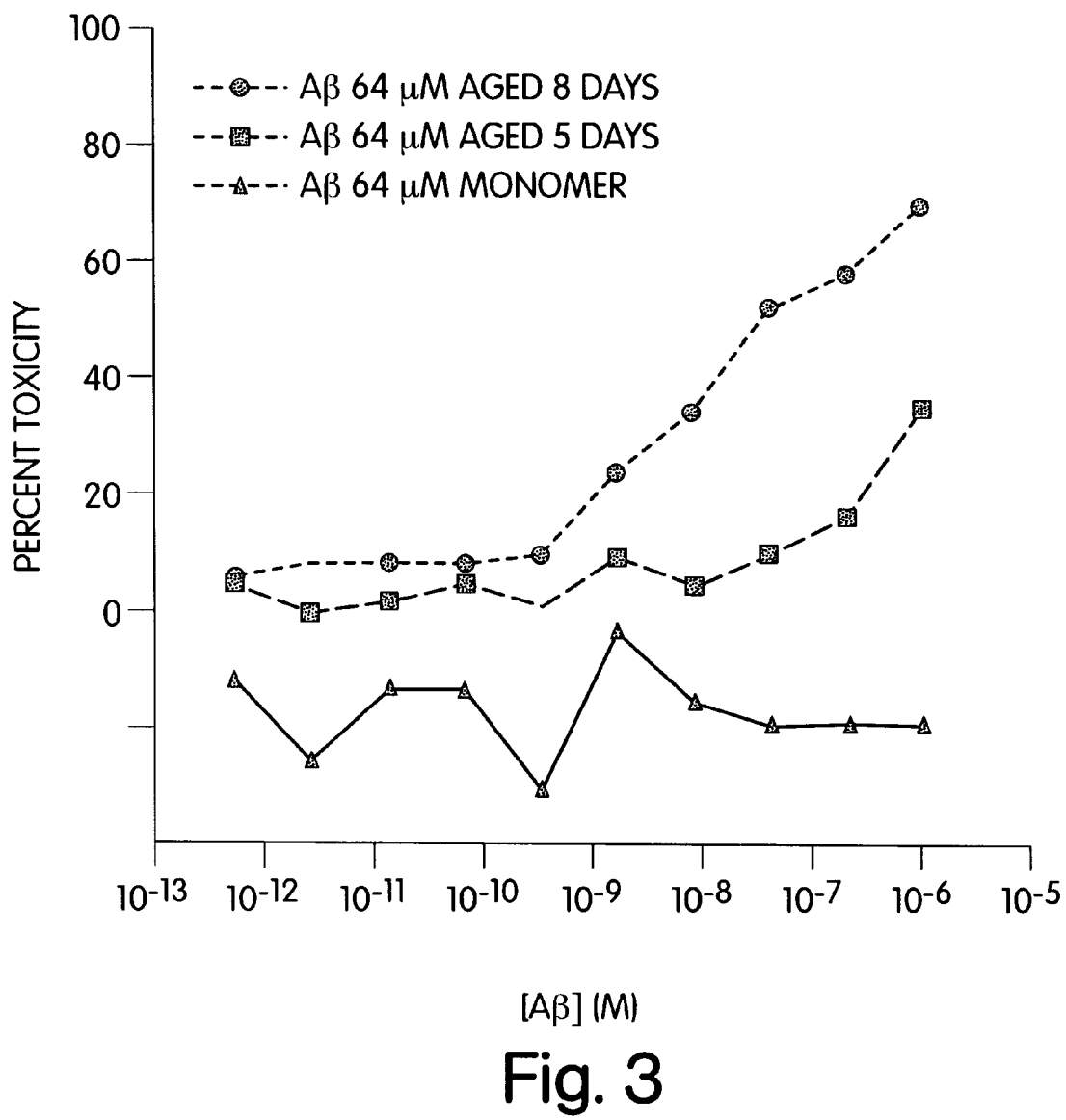
FIG. 3 is a graphic representation of the toxicity of Aβ$_{1-40}$ aggregates, but not Aβ$_{1-40}$ monomers, to cultured neuronal cells.
Figure 4A:
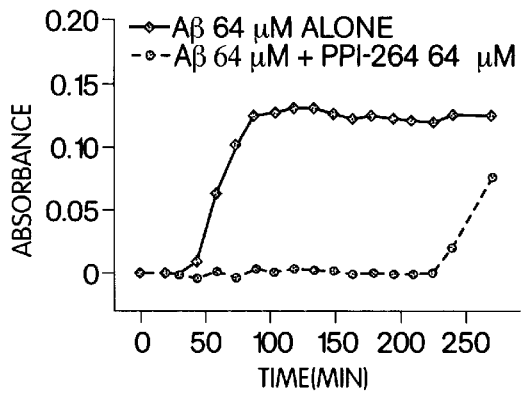
FIG. 4 is a graphic representation of the aggregation of Aβ$_{1-40}$ in the presence of an equimolar amount of cholyl-Aβ$_{6-20}$ (panel A), a ~2-fold molar excess of cholyl-Aβ$_{6-20}$ (panel B) or a ~6-fold molar excess of cholyl-Aβ$_{6-20}$ (panel C) and the corresponding toxicity of the aggregates of panels A, B and C to cultured neuronal cells (panels D, E and F, respectively).
Figure 4B:
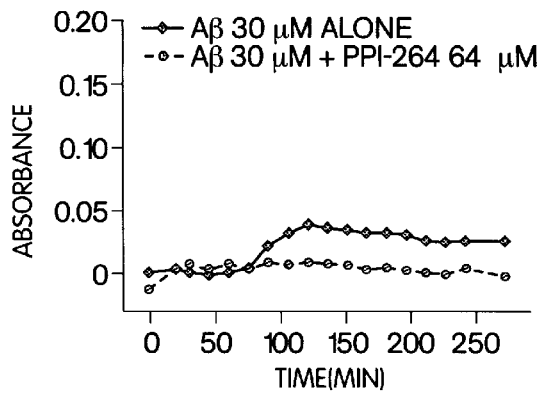
Figure 4C:
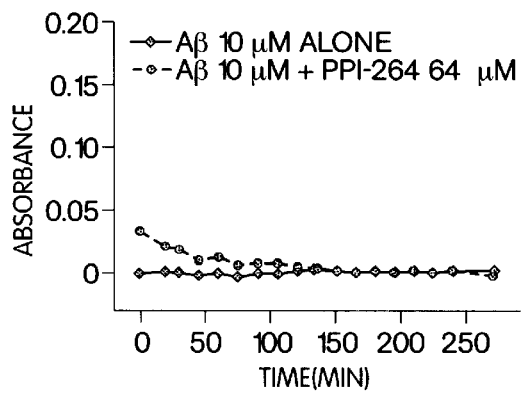
Figure 4D:
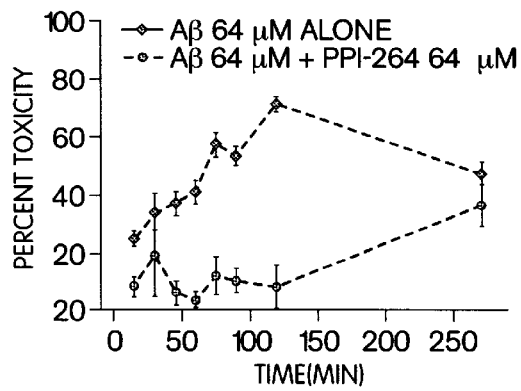
Figure 4E:
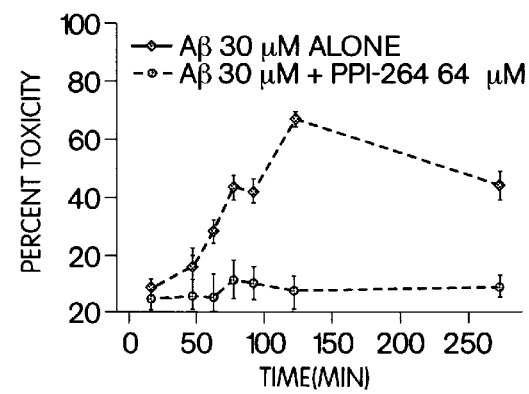
Figure 4F:
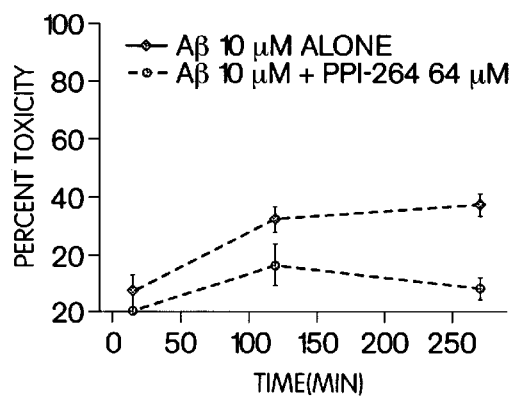

The neurotoxicity of aged (5 day or 8 day) $A\beta_{1-40}$ aggregates alone, but not fresh $A\beta_{1-40}$ monomers alone, was confirmed in an experiment the results of which are shown in FIG. 3, which demonstrates that incubating the neuronal cells with increasing amounts of fresh $A\beta_{1-40}$ monomers was not significantly toxic to the cells whereas incubating the cells with increasing amounts of 5 day or 8 day $A\beta_{1-40}$ aggregates led to increasing amount of neurotoxicity. The EC50 for toxicity of aged $A\beta_{1-40}$ aggregates was 1–2 µM for both the PC12 cells and the NT2 cells.

To determine the effect of a β-amyloid modulator compound on the neurotoxicity of $A\beta_{1-40}$ aggregates, a modulator compound, cholyl-$A\beta_{6-20}$ (PPI-264), was preincubated with $A\beta_{1-40}$ monomers under standard nucleation assay conditions as described in Example 6 and at particular time intervals post-incubation, aliquots of the β-AP/modulator solution were removed and 1) the turbidity of the solution was assessed as a measure of aggregation and 2) the solution was applied to cultured neuronal cells for 48 hours at which time cell viability was assessed using MTT to determine the neurotoxicity of the solution. The results of the turbidity analysis are shown in FIG. 4, panels A, B and C. In panel A, $A\beta_{1-40}$ and cholyl-$A\beta_{6-20}$ were both present at 64 µM. In panel B, $A\beta_{1-40}$ was present at 30 µM and cholyl-$A\beta_{6-20}$ was present at 64 µM. In panel C, $A\beta_{1\ 40}$ was present at 10 µM and cholyl-$A\beta_{6-20}$ was present at 64 tM. These data show that an equimolar amount of cholyl-$A\beta_{6-20}$ is effective at inhibiting aggregation of $A\beta_{1-40}$ (see FIG. 4, panel A) and that as the concentration of $A\beta_{1-40}$ is reduced, the amount of detectable aggregation of the $A\beta_{1-40}$ monomer is correspondingly reduced (compare FIG. 4, panels B and C with panel A). The corresponding results of the neurotoxicity analysis are shown in FIG. 4, panels D, E, and F. These results demonstrate that the β-amyloid modulator compound not only inhibits aggregation of $A\beta_{1-40}$ monomers but also inhibits the neurotoxicity of the $A\beta_{1-40}$ solution, illustrated by the reduced percent toxicity of the cells when incubated with the $A\beta_{1-40}$/modulator solution as compared to $A\beta_{1-40}$ alone (see e.g., FIG. 4, panel D). Moreover, even when $A\beta_{1-40}$ aggregation was not detectable as measured by light scattering, the modulator compound inhibited the neurotoxicity of the $A\beta_{1-40}$ solution (see FIG. 4, panels E and F). Thus, the formation of neurotoxic $A\beta_{1-40}$ aggregates precedes the formation of insoluble aggregates detectable by light scattering and the modulator compound is effective at inhibiting the inhibiting the formation and/or activity of these neurotoxic aggregates. Similar results were seen with other modulator compounds, such as iminobiotinyl-$A\beta_{6-20}$ (PPI-267), cholyl-$A\beta_{16-20}$ (PPI-350) and cholyl-$A\beta_{16-20}$-amide (PPI-319).

Additionally, the β-amyloid modulator compounds have been demonstrated to reduce the neurotoxicity of preformed $A\beta_{1-40}$ aggregates. In these experiments, $A\beta_{1-40}$ aggregates were preformed by incubation of the monomers in the absence of any modulators. The modulator compound was then incubated with the preformed $A\beta_{1-40}$ aggregates for 24 hours at 37° C., after which time the β-AP/modulator solution was collected and its neurotoxicity evaluated as described above. Incubation of preformed $A\beta_{1-40}$ aggregates with the modulator compound prior to applying the solution to neuronal cells resulted in a decrease in the neurotoxicity of the $A\beta_{1-40}$ solution. These results suggest that the modulator can either bind to Aβ fibrils or soluble aggregate and modulate their inherent neurotoxicity or that the modulator can perturb the equilibrium between monomeric and aggregated forms of $A\beta_{1-40}$ in favor of the non-neurotoxic form.

EXAMPLE 11

Characterization of Additional β-Amyloid Modulator Compounds

In this example, additional modulator compounds designed based upon amino acids 17–20 of Aβ, LVFF (SEQ ID NO: 12) (identified in Example 9), were prepared and analyzed to further delineate the structural features necessary for inhibition of β-amyloid aggregation. Types of compounds analyzed included ones having only three amino acid residues of an Aβ aggregation core domain, compounds in which the amino acid residues of an Aβ aggregation core domain were rearranged or in which amino acid substitutions had been made, compounds modified with a carboxy-terminal modifying group and compounds in which the modifying group had been derivatized. Abbreviations used in this example are: h- (free amino terminus), -oh (free carboxylic acid terminus), $-nh_2$ (amide terminus), CA (cholyl, the acyl portion of cholic acid), NANA (N-acetyl neuraminyl), IB (iminobiotinyl), βA (β-alanyl), DA (D-alanyl), Adp (aminoethyldibenzofuranylpropanoic acid), Aic (3-(O-aminoethyl-iso)-cholyl, a derivative of cholic acid), IY (iodotyrosyl), o-methyl (carboxy-terminal methyl ester), N—me (N-methyl peptide bond), DeoxyCA (deoxycholyl) and LithoCA (lithocholyl).

Modulator compounds having an Aic modifying group at either the amino- or carboxy-terminus (e.g., PPI-408 and PPI-418) were synthesized using known methods (see e.g., Wess, G. et al. (1993) *Tetrahedron Letters*, 34:817–822; Wess, G. et al. (1992) *Tetrahedron Letters* 33:195–198). Briefly, 3-iso-O-(2-aminoethyl)-cholic acid (3β-(2-aminoethoxy)-7α,12α-dihydroxy-5β-cholanoic acid) was converted to the FMOC-protected derivative using FMOC-OSu (the hydroxysuccinimide ester of the FMOC group, which is commercially available) to obtain a reagent that was used to introduce the cholic acid derivative into the compound. For N-terminal introduction of the cholic acid moiety, the FMOC-protected reagent was coupled to the N-terminal amino acid of a solid-phase peptide in the standard manner, followed by standard FMOC-deprotection conditions and subsequent cleavage from the resin, followed by HPLC purification. For C-terminal introduction of the cholic acid moiety, the FMOC-protected reagent was attached to 2-chlorotrityl chloride resin in the standard manner. This amino acyl derivatized resin was then used in the standard manner to synthesize the complete modified peptide.

The modulators were evaluated in the nucleation and seeded extension assays described in Example 6 and the results are summarized below in Table V. The change in lag time (ΔLag) is presented as the ratio of the lag time observed in the presence of the test compound to the lag time of the control. Data are reported for assays in the presence of 100 mole % inhibitor relative to the concentration of $A\beta_{1-40}$, except for PPI-315, PPI-348, PPI-380, PPI-407 and PPI-418, for which the data is reported in the presence of 33 mole % inhibitor. Inhibition (% $I_{nucl'n}$) is listed as the percent reduction in the maximum observed turbidity in the control at the end of the assay time period. Inhibition in the extension assay (% $I_{ext'n}$) is listed as the percent reduction of thioflavin-T fluorescence of β-structure in the presence of 25 mole % inhibitor. Compounds with a % $I_{nucl'n}$ of at least 30% are highlighted in bold.

TABLE V

| Ref # | N-Term. Mod. | Peptide | C Term. Mod. | ΔLag | % I$_{nucl'n}$ | % I$_{ext'n}$ |
|---|---|---|---|---|---|---|
| PPI-293 | CA | — | -oh | 1.0 | 0 | ND* |
| PPI-315 | CA | HQKLVFF (SEQ ID NO: 6) | -nh$_2$ | 1.1 | 5** | ND |
| PPI-316 | NANA | HQKLVFF (SEQ ID NO: 6) | -nh$_2$ | 1.5 | −15 | ND |
| PPI-319 | CA | KLVFF (SEQ ID NO: 10) | -nh$_2$ | 5.4 | 70 | 52 |
| PPI-339 | CA | HDSGY (SEQ ID NO: 36) | -nh$_2$ | 1.1 | −18 | ND |
| PPI-348 | CA | HQKLVFF (SEQ ID NO: 6) | -oh | 2.0 | 70** | ND |
| PPI-349 | CA | QKLVFF (SEQ ID NO: 8) | -oh | >5 | 100 | 56 |
| PPI-350 | CA | KLVFF (SEQ ID NO: 10) | -oh | 1.8 | 72 | 11 |
| PPI-365 | CA | AAAAA (SEQ ID NO: 35) | -oh | 0.8 | −7 | 0 |
| PPI-366 | CA | QKLVF (SEQ ID NO: 37) | -oh | 3.1 | −23 | ND |
| PPI-368 | CA | LVFFA (SEQ ID NO: 11) | -oh | >5 | 100 | 91 |
| PPI-369 | CA | KLTFF (SEQ ID NO: 38) | -oh | 1.1 | −16 | 44 |
| PPI-370 | CA | KLVAF (SEQ ID NO: 30) | -oh | 2.6 | 73 | 31 |
| PPI-371 | CA | KLVFF(βA) (SEQ ID NO: 31) | -oh | 2.5 | 76 | 80 |
| PPI-372 | CA | FKFVL (SEQ ID NO: 29) | -oh | 0.8 | 45 | 37 |
| PPI-373 | NANA | KLVFF (SEQ ID NO: 10) | -oh | 0.9 | 16 | 8 |
| PPI-374 | IB | KLVFF (SEQ ID NO: 10) | -oh | 1.3 | 86 | 0 |
| PPI-375 | CA | KTVFF (SEQ ID NO: 39) | -oh | 1.2 | 18 | 21 |
| PPI-377 | h- | KLVFF (SEQ ID NO: 10) | -oh | 1.1 | 0 | 8 |
| PPI-379 | CA | LVFFAE (SEQ ID NO: 27) | -oh | 1.4 | 55 | 16 |
| PPI-380 | CA | LVFF (SEQ ID NO: 12) | -oh | 1.8 | 72** | 51 |
| PPI-381 | CA | LVFF(DA) (SEQ ID NO: 32) | -oh | 2.3 | 56 | 11 |
| PPI-382 | CA | LVFFA (SEQ ID NO: 11) | -nh$_2$ | 1.0 | −200 | 91 |
| PPI-383 | h-DDIIL-(Adp) | VFF | -oh | 0.4 | 14 | 0 |
| PPI-386 | h- | LVFFA (SEQ ID NO: 11) | -oh | 1.0 | 15 | 11 |
| PPI-387 | h- | KLVFF (SEQ ID NO: 10) | -nh$_2$ | 1.3 | −9 | 39 |
| PPI-388 | CA | AVFFA (SEQ ID NO: 25) | -oh | 1.4 | 68 | 44 |
| PPI-389 | CA | LAFFA (SEQ ID NO: 13) | -oh | 1.5 | 47 | 66 |
| PPI-390 | CA | LVAFA (SEQ ID NO: 33) | -oh | 2.7 | 25 | 0 |
| PPI-392 | CA | VFFA (SEQ ID NO: 24) | -oh | 2.0 | 76 | 10 |
| PPI-393 | CA | LVF | -oh | 1.3 | 1 | 0 |
| PPI-394 | CA | VFF | -oh | 1.8 | 55 | 0 |
| PPI-395 | CA | FFA | -oh | 1.0 | 51 | 6 |
| PPI-396 | CA | LV(IY)FA (SEQ ID NO: 23) | -oh | >5 | 100 | 71 |
| PPI-401 | CA | LVFFA (SEQ ID NO: 11) | -o-methyl | ND | ND | 0 |
| PPI-405 | h- | LVFFA (SEQ ID NO: 11) | -nh$_2$ | 1.3 | 11 | 70 |
| PPI-407 | CA | LVFFK (SEQ ID NO: 22) | -oh | >5 | 100** | 85 |
| PPI-408 | h- | LVFFA (SEQ ID NO: 11) | (Aic)-oh | 3.5 | 46 | 3 |
| PPI-418 | h-(Aic) | LVFFA (SEQ ID NO: 11) | -oh | >5 | 100** | 87 |
| PPI-426 | CA | FFVLA (SEQ ID NO: 40) | -oh | >5 | 100 | 89 |
| PPI-391 | CA | LVFAA | -oh | 1.6 | 40 | ND |

TABLE V-continued

| Ref # | N-Term. Mod. | Peptide | C Term. Mod. | ΔLag | % $I_{nucl'n}$ | % $I_{ext'n}$ |
|---|---|---|---|---|---|---|
| PPI-397 | CA | (SEQ ID NO: 41) LVF(IV)A | -oh | >5 | 95 | ND |
| PPI-400 | CA | (SEQ ID NO: 42) AVAFA | -oh | 1.0 | −15 | ND |
| PPI-403 | *** | (SEQ ID NO: 26) HQKLVFF | -oh | 1.4 | −75 | 0 |
| PPI-404 | **** | (SEQ ID NO: 6) LKLVFF | -oh | 1.8 | −29 | 7 |
| PPI-424 | DeoxyCA | (SEQ ID NO: 43) LVFFA | -oh | 3.0 | −114 | 82 |
| PPI-425 | LithoCA | (SEQ ID NO: 11) LVFFA | -oh | 2.8 | −229 | 0 |
| PPI-428 | CA | (SEQ ID NO: 11) FF | -oh | 1.7 | −78 | 15 |
| PPI-429 | CA | FFV | -oh | 2.2 | −33 | 7 |
| PPI-430 | CA | FFVL | -oh | 4.1 | 33 | 75 |
| PPI-433 | CA | (SEQ ID NO: 28) LVFFA (all D amino acids) | -oh | 2.8 | 27 | ND |
| PPI-435 | t-Boc | LVFFA (SEQ ID NO: 11) | -oh | 3.0 | −5 | ND |
| PPI-438 | CA | GFF | -oh | 1.0 | 0 | ND |

*ND = not done
** = 33 mol %
*** = h-DDIII(N—Me—Val)DLL(Adp) (SEQ ID NO: 44)
**** = h-DDII(N—Me—Leu)VEH(Adp) (SEQ ID NO: 45).

Certain compounds shown in Table V (PPI-319, PPI-349, PPI-350, PPI-368 and PPI-426) also were tested in neurotoxicity assays such as those described in Example 10. For each compound, the delay of the appearance of neurotoxicity relative to control coincided with the delay in the time at which polymerization of Aβ began in the nucleation assays. This correlation between the prevention of formation of neurotoxic Aβ species and the prevention of polymerization of Aβ was consistently observed for all compounds tested.

The results shown in Table V demonstrate that at an effective modulator compound can comprise as few as three Aβ amino acids residues (see PPI-394, comprising the amino acid sequence VFF, which corresponds to $Aβ_{18-20}$, and PPI-395, comprising the amino acid sequence FFA, which corresponds to $Aβ_{19-21}$). The results also demonstrate that a modulator compound having a modulating group at its carboxy-terminus is effective at inhibiting Aβ aggregation (see PPI-408, modified at its C-terminus with Aic). Still further, the results demonstrate that the cholyl group, as a modulating group, can be manipulated while maintaining the inhibitory activity of the compounds (see PPI-408 and PPI-418, both of which comprise the cholyl derivative Aic). The free amino group of the Aic derivative of cholic acid represents a position at which a chelation group for $^{99m}Tc$ can be introduced, e.g., to create a diagnostic agent. Additionally, the ability to substitute iodotyrosyl for phenylalanine at position 19 or 20 of the Aβ sequence (see PPI-396 and PPI-397) while maintaining the ability of the compound to inhibit Aβ aggregation indicates that the compound could be labeled with radioactive iodine, e.g., to create a diagnostic agent, without loss of the inhibitory activity of the compound.

Finally, compounds with inhibitory activity were created using, Aβ derived amino acids but wherein the amino acid sequence was rearranged or had a substitution with a non-Aβ-derived amino acid. Examples of such compounds include PPI-426, in which the sequence of $Aβ_{17-21}$ (LVFFA; SEQ ID NO: 11) has been rearranged (FFVLA; SEQ ID NO: 40), PPI-372, in which the sequence of $Aβ_{16-20}$ (KLVFF; SEQ ID NO: 10) has been rearranged (FKFVL; SEQ ID NO: 29), and PPI-388, -389 and -390, in which the sequence of $Aβ_{17-21}$ (LVFFA; SEQ ID NO: 11) has been substituted at position 17, 18 or 19, respectively, with an alanine residue (AVFFA (SEQ ID NO: 25) for PPI-388, LAFFA (SEQ ID NO: 13) for PPI-689 and LVAFA (SEQ ID NO: 33) for PPI-390). The inhibitory activity of these compounds indicate that the presence in the compound of an amino acid sequence directly corresponding to a portion of Aβ is not essential for inhibitory activity, but rather suggests that maintenance of the hydrophobic nature of this core region, by inclusion of amino acid residues such as phenylalanine, valine, leucine, regardless of their precise order, can be sufficient for inhibition of Aβ aggregation.

EXAMPLE 12

Characterization of β-Amyloid Modulator Compounds Comprising an Unmodified β-Amyloid Peptide To examine the ability of unmodified Aβ pepti des to modulate aggregation of natural β-AP, a series of Aβ peptides having amino- and/or carboxy terminal deletions as compared to $Aβ_{1-40}$, or having internal amino acids deleted (i.e., noncontiguous peptides), were prepared. One peptide (PPI-220) had additional, non-Aβ-derived amino acid residues at its amino-terminus. These peptides all had a free amino group at the amino-terminus and a free carboxylic acid at the carboxy-terrninus. These unmodified peptides were evaluated in assays as described in Example 7. The results are summarized below in Table VI, wherein the data is presented as described in Example 7. Compounds exhibiting at least a 1.5 fold increase in lag time are highlighted in bold.

TABLE VI

| Reference # | Aβ Peptide | Mole % | Fold Increase in Lag Time | % Inhibition of Plateau |
|---|---|---|---|---|
| PPI-226 | $A\beta_{6-20}$ | 100 | 1.66 | 76 |
| PPI-227 | $A\beta_{11-25}$ | 100 | ~1 | 47 |
| PPI-228 | $A\beta_{16-30}$ | 100 | >4.5 | 100 |
| PPI-229 | $A\beta_{21-35}$ | 100 | ~1 | ~0 |
| PPI-230 | $A\beta_{26-40}$ | 100 | 0.8 | ~0 |
| PPI-231 | $A\beta_{1-15}$ | 100 | ~1 | 18 |
| PPI-247 | $A\beta_{1-30,\ 36-40}$ (Δ31–35) | 100 | ~1 | ~0 |
| PPI-248 | $A\beta_{1-25,\ 31-40}$ (Δ26–30) | 100 | 1.58 | ~0 |
| PPI-249 | $A\beta_{1-20,\ 26-40}$ (Δ21–25) | 100 | 2.37 | ~0 |
| PPI-250 | $A\beta_{1-15,\ 21-40}$ (Δ16–20) | 100 | 1.55 | ~0 |
| PPI-251 | $A\beta_{1-10,\ 16-40}$ (Δ11–15) | 100 | ~1.2 | ~0 |
| PPI-252 | $A\beta_{1-5,\ 11-40}$ (Δ6–10) | 100 | 1.9 | 33 |
| PPI-253 | $A\beta_{6-40}$ | 100 | 1.9 | ~0 |
| PPI-220 | EEVVHHHHQQ-$A\beta_{16-40}$ (SEQ ID NO: 16) | 100 | >4 | 100 |

The results shown in Table VI demonstrate that limited portions of the Aβ sequence can have a significant inhibitory effect on natural β-AP aggregation even when the peptide is not modified by a modifying group. Preferred unmodified peptides are $A\beta_{6-20}$ (PPI-226), $A\beta_{16-30}$ (PPI-228), $A\beta_{1-20,\ 26-40}$ (PPI-249) and EEVVHHHHQQ-$A\beta_{16-40}$ (SEQ ID NO: 16) (PPI-220), the amino acid sequences of which are shown in SEQ ID NOs: 4, 14, 15, and 16, respectively.

Forming part of this disclosure is the appended Sequence Listing, the contents of summarize in the Table below.

| SEQ ID NO: | Amino Acids | Peptide Sequence |
|---|---|---|
| 1 | 43 amino acids | $A\beta_{1-43}$ |
| 2 | 103 amino acids | APP C-terminus |
| 3 | 43 amino acids | $A\beta_{1-43}$ (19, 20 mutated) |
| 4 | HDSGYEVHHQKLVFF | $A\beta_{6-20}$ |
| 5 | HQKLVFFA | $A\beta_{14-21}$ |
| 6 | HQKLVFF | $A\beta_{14-20}$ |
| 7 | QKLVFFA | $A\beta_{15-21}$ |
| 8 | QKLVFF | $A\beta_{15-20}$ |
| 9 | KLVFFA | $A\beta_{16-21}$ |
| 10 | KLVFF | $A\beta_{16-20}$ |
| 11 | LVFFA | $A\beta_{17-21}$ |
| 12 | LVFF | $A\beta_{17-20}$ |
| 13 | LAFFA | $A\beta_{17-21}$ ($V_{18} \rightarrow A$) |
| 14 | KLVFFAEDVGSNKGA | $A\beta_{16-30}$ |
| 15 | 35 amino acids | $A\beta_{1-20,\ 26-40}$ |
| 16 | 35 amino acids | EEVVHHHHQQ-$\beta AP_{16-40}$ |
| 17 | AGAAAAGA | PrP peptide |
| 18 | AILSS | amylin peptide |
| 19 | VFF | $A\beta_{18-20}$ |
| 20 | FFA | $A\beta_{19-21}$ |
| 21 | FFVLA | $A\beta_{17-21}$ (scrambled) |
| 22 | LVFFK | $A\beta_{17-21}$ ($A_{21} \rightarrow K$) |
| 23 | LV(IY)FA | $A\beta_{17-21}$ ($F_{19} \rightarrow IY$) |
| 24 | VFFA | $A\beta_{18-21}$ |
| 25 | AVFFA | $A\beta_{17-21}$ ($L_{17} \rightarrow A$) |
| 26 | LVF(IY)A | $A\beta_{17-21}$ ($F_{20} \rightarrow IY$) |
| 27 | LVFFAE | $A\beta_{17-22}$ |
| 28 | FFVL | $A\beta_{17-20}$ (scrambled) |
| 29 | FKFVL | $A\beta_{16-20}$ (scrambled) |
| 30 | KLVAF | $A\beta_{16-20}$ ($F_{19} \rightarrow A$) |
| 31 | KLVFF(βA) | $A\beta_{16-21}$ ($A_{21} \rightarrow \beta A$) |
| 32 | LVFF(DA) | $A\beta_{17-21}$ ($A_{21} \rightarrow DA$) |
| 33 | LVAFA | |
| 34 | DDIIL-Adp | |
| 35 | AAAAA | |
| 36 | HDSGY | |
| 37 | QKLVF | |
| 38 | KLTFF | |
| 39 | KTVFF | |
| 40 | FFVLA | |
| 41 | LVFAA | |
| 42 | AVAFA | |
| 43 | LKLVFF | |
| 44 | DDIII-(N—Me—Val)—DLL—(Adp) | |
| 45 | DDII-(N—Me—Leu)—VEH—(Adp) | |

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. An amyloid modulator compound having the structure:

wherein Xaa is an amyloidogenic protein, or peptide fragment thereof, and A is a modifying group comprising a cis-decalin group, a cholanoyl structure, a cholyl group, a diethylene-triaminepentaacetyl group, a (−)-menthoxyacetyl group, a fluorescein-containinag group, or an N-acetylneuraminyl group, covalently attached to the α-amino group at the amino-terminus of the amyloidogenic protein, or peptide fragment thereof, such that the compound modulates the aggregation of natural amyloid proteins or peptides when contacted with the natural amyloidogenic proteins or peptides.

2. The compound of claim 1, which inhibits aggregation of natural amyloidogenic proteins or peptides when contacted with the natural amyloidogenic proteins or peptides.

3. The compound of claim 2, which inhibits aggregation of natural amyloidogenic proteins or peptides when contacted with a molar excess amount of natural amyloidogenic proteins or peptides.

4. The compound of claim 1 or 3, which is further modified to alter a pharmacokinetic property of the compound.

5. The compound of claim 1 or 3, which is further modified to label the compound with a detectable substance.

6. The compound of claim 1 or 3, wherein the amyloidogenic protein, or peptide fragment thereof, is selected from the group consisting of transthyretin (TTR), prion protein (PrP), islet amyloid polypeptide (IAPP), atrial natriuretic factor (ANF), kappa light chain, lambda light chain, amyloid A, procalcitonin, cystatin C, β2 microglobulin, ApoA-I, gelsolin, calcitonin, fibrinogen and lysozyme.

7. An amyloid modulator compound having the structure:

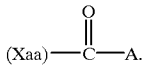

wherein Xaa is an amyloidogenic protein, or peptide fragment thereof, and A is a modifying group comprising a cis-decalin group, a cholanoyl structure, a cholyl group, a diethylene-triamepentaacetyl group, a (−)-menthoxyacetyl group, a fluorescein-containing group, or an N-acetylneuraminyl group, covalently attached to the carboxy-terminus of the amyloidogenic protein, or peptide fragment thereof, such that the compound modulates the aggregation of natural amyloid proteins or peptides when contacted with the natural amyloidogenic proteins or peptides.

8. The compound of claim 1 or 7, wherein the modifying group contains a cis-decalin group.

9. The compound of claim 8, wherein the modifying group contains a cholanoyl structure.

10. The compound of claim 9, wherein the modifying group is a cholyl group.

11. A pharmaceutical composition comprising a therapeutically effective amount of the compound of claim 1 or 7 and a pharmaceutically acceptable carrier.

12. A compound comprising an amyloidogenic peptide comprising at least one D-amino acid and having a modifying group attached to the peptide, wherein said modifying group is not a n acetyl or amide group and comprises a cyclic, heterocyclic, or polycyclic group having 4 to 10 carbon atoms, or other moiety having similar steric bulk, and wherein the compound inhibits aggregation of natural amyloidogenic proteins or peptides when contacted with the natural amyloidogenic proteins or peptides, provided that said peptide is not calcitonin.

13. The compound of claim 12, which comprises a modifying group attached to the amino-terminal end of the amyloidgenic peptide.

14. The compound of claim 12, which comprises a modifying group attached to the carboxy-terminal end of the amyloidogenic peptide.

15. The compound of claim 13 or 14, wherein the modifying group comprises a cyclic, heterocyclic or polycyclic group.

16. The compound of claim 12, 13 or 14, wherein the amyloidogenic peptide is comprised entirely of D-amino acids.

17. The compound of claim 12, 13, or 14, which is modified to label the compound with a detectable substance.

18. The compound of claim 12, 13 or 14, which is modified to alter a pharmacokinetic proper ty of the compound.

19. The compound of claim 13 or 14, wherein the amyloidogenic peptide is from a protein or polypeptide selected from the group consisting of transthyretin (TTR), prion protein (PrP), islet amyloid polypeptide (IAPP), atrial natriuretic factor (ANF), kappa light chain, lambda light chain, amyloid A, procalcitonin, cystatin C, β2 microglobulin, ApoA-I, gelsolin, fibrinogen and lysozyme.

20. A pharmaceutical composition comprising a therapeutically effective amount of t he compound of claim 12, 13 or 14 and a pharmaceutically acceptable carrier.

21. A compound comprising a retro-inverso isomer of an amyloidogenic peptide, and having a modifying group attached to said isomer, wherein said modifying group is not an acetyl or amide group and comprises a cyclic, heterocyclic, or polycyclic group having 4 to 10 carbon atoms, or other moiety having similar steric bulk, and wherein the compound inhibits aggregation of natural amyloidogenic proteins or peptides when contacted with the natural amyloidogenic proteins or peptides.

22. The compound of claim 21, which comprises a modifying group attached to the amino-terminal end of the amyloidgenic peptide.

23. The compound of claim 21, which comprises a modifying group attached to the carboxy-terminal end of the amyloidogenic peptide.

24. The compound of claim 22 or 23, wherein the modifying group comprises a cyclic, heterocyclic or polycyclic group.

25. The compound of claim 21, 22 or 23, which is modified to label the compound with a detectable substance.

26. The compound of claim 21, 22 or 23, which is modified to alter a pharmacokinetic property of the compound.

27. The compound of claim 22 or 23, wherein the amyloidogenic peptide is a protein or polypeptide selected from the group consisting of transthyretin (TTR), prion protein (PrP), islet amyloid polypeptide (IAPP), atrial natriuretic factor (ANF), kappa light chain, lambda light chain, amyloid A, procalcitonin, cystatin C, β2 microglobulin, ApoA-I, gelsolin, calcitonin, fibrinogen and lysozyme, or a peptide fragment thereof.

28. A pharmaceutical composition comprising a therapeutically effective amount of the compound of claim 21, 22 or 23 and a pharmaceutically acceptable carrier.

29. A pharmaceutical composition comprising a compound comprising an amyloidogenic peptide, and a pharmaceutically acceptable carrier, said amyloidogenic peptide comprising at least one D-amino acid, wherein said peptide inhibits aggregation of natural amyloidogenic proteins or peptides when contacted with natural amyloidogenic proteins or peptides, provided that said peptide is not calcitonin.

30. A pharmaceutical composition comprising a compound comprising a retro-inverso isomer of an amyloidogenic peptide, and a pharmaceutically acceptable carrier, wherein the retro-inverso isomer inhibits aggregation of natural amyloidogenic proteins or peptides when contacted with natural amyloidogenic proteins or peptides.

31. The compound of any one of claims 12 or 21, wherein said cyclic, heterocyclic, or polycyclic group has 5 to 7 carbon atoms.

32. The compound of any one of claims 12 or 21, wherein said cyclic, heterocyclic, or polycyclic group has 4 to 8 carbon atoms.

33. A compound comprising an amyloidogenic peptide comprising at least one D-amino acid and having a modifying group attached to the peptide, wherein said modifying group comprises a cyclic, heterocyclic, or polycyclic group having 4 to 10 carbon atoms, or other moiety having similar steric bulk, and wherein the compound inhibits aggregation of natural amyloidogenic proteins or peptides when contacted with the natural amyloidogenic proteins or peptides, provided that said peptide is not calcitonin or atrial natriuretic factor.

34. A compound comprising a retro-inverso isomer of an amyloidogenic peptide, and having a modifying group attached to said isomer, wherein said modifying group comprises a cyclic, heterocyclic, or polycyclic group having 4 to 10 carbon atoms, or other moiety having similar steric bulk, and wherein the compound inhibits aggregation of natural amyloidogenic proteins or peptides when contacted with the natural amyloidogenic proteins or peptides, provided that said peptide is not atrial natriuretic factor.

35. The pharmaceutical composition of claim 29, wherein said amyloidgenic peptide comprises a modifying group.

36. The pharmaceutical composition of claim 35, wherein said modifying group is attached to the amino-terminal end of the amyloidgenic peptide.

37. The pharmaceutical composition of claim 35, wherein said modifying group is attached to the carboxy-terminal end of the amyloidogenic peptide.

38. The pharmaceutical composition of claim 35, wherein, wherein said modifying group comprises a cyclic, heterocyclic or polycyclic group.

39. The pharmaceutical composition of claim 38, wherein said cyclic, heterocyclic. or polycyclic group has 5 to 7 carbon atoms.

40. The pharmaceutical composition of claim 38, wherein said cyclic, heterocyclic, or polycyclic group has 4 to 8 carbon atoms.

41. The pharmaceutical composition of claim 35, wherein said modifying group comprises a detectable substance.

42. The pharmaceutical composition of claim 35, wherein said modifying group alters a pharmacokinetic property of the compound.

43. The pharmaceutical composition of any one of claims 29 or 30, wherein the amyloidogenic peptide is a protein or polypeptide selected from the group consisting of transthyretin (TTR), prion protein (PrP), islet amyloid polypeptide (IAPP), atrial natriuretic factor (ANF), kappa light chain, lambda light chain, amyloid A, procalcitonin, cystatin C, β2 microglobulin, ApoA-I, gelsolin, fibrinogen and lysozyme, or a peptide fragment thereof.

44. The pharmaceutical composition of claim 29, wherein the amyloidogenic peptide is comprised entirely of D-amino acids.

45. The pharmaceutical composition of claim 30, wherein said retro-inverso isomer of an amyloidgenic peptide comprises a modifying group.

46. The pharmaceutical composition of claim 45, wherein said modifying group is attached to the amino-terminal end of the retro-inverso isomer of an amyloidgenic peptide.

47. The pharmaceutical composition of claim 45, wherein said modifying group is attached to the carboxy-terminal end of the retro-inverso isomer of an amyloidogenic peptide.

48. The pharmaceutical composition of claim 45, wherein, wherein said modifying group comprises a cyclic, heterocyclic or polycyclic group.

49. The pharmaceutical composition of claim 48, wherein said cyclic, heterocyclic, or polycyclic group has 5 to 7 carbon atoms.

50. The pharmaceutical composition of claim 48, wherein said cyclic, heterocyclic, or polycyclic group has 4 to 8 carbon atoms.

51. The pharmaceutical composition of claim 45, wherein said modifying group comprises a detectable substance.

52. The pharmaceutical composition of claim 45, wherein said modifying group alters a pharmacokinetic property of the compound.

* * * * *

UNITED STATES PATENT AND TRADEMARK OFFICE
CERTIFICATE OF CORRECTION

PATENT NO. : 6,319,498 B1
DATED : November 20, 2001
INVENTOR(S) : Mark A. Findeis et al.

It is certified that error appears in the above-identified patent and that said Letters Patent is hereby corrected as shown below:

Column 89,
Lines 59, 62, and 64, delete "Claim 1 or Claim 3" and insert -- Claim 1 or Claim 7 --.

Column 90,
Line 67, delete "a n" and insert -- an --.

Column 91,
Lines 16, 19, 21 and 32, delete "Claim 12, 13 or 14" and insert -- Claim 13 or 14 --.
Line 32, delete "t he" and insert -- the --.
Lines 52, 54 and 66, delete "Claim 21, 22 or 23" and insert -- Claim 22 or 23 --.

Column 92,
Line 47, delete "wherein" between "claim 35" and "wherein".

Signed and Sealed this

Twenty-fifth Day of March, 2003

JAMES E. ROGAN
*Director of the United States Patent and Trademark Office*

SEQUENCE LISTING (1) GENERAL INFORMATION:

(iii) NUMBER OF SEQUENCES: 45

(2) INFORMATION FOR SEQ ID NO:1:

(i) SEQUENCE CHARACTERISTICS:
       (A) LENGTH: 43 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO:1:

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala Thr
            35                  40

(2) INFORMATION FOR SEQ ID NO:2:

(i) SEQUENCE CHARACTERISTICS:
       (A) LENGTH: 103 amino acids
       (B) TYPE: amino acid
       (D) TOPOLOGY: linear (ii) MOLECULE TYPE: peptide (v) FRAGMENT TYPE: internal (xi) SEQUENCE DESCRIPTION: SEQ ID NO:2:

Glu Val Lys Met Asp Ala Glu Phe Arg His Asp Ser Gly Tyr Glu Val
1               5                   10                  15

His His Gln Lys Leu Val Phe Phe Ala Glu Asp Val Gly Ser Asn Lys
            20                  25                  30

Gly Ala Ile Ile Gly Leu Met Val Gly Gly Val Val Ile Ala Thr Val
            35                  40                  45

Ile Val Ile Thr Leu Val Met Leu Lys Lys Lys Gln Tyr Thr Ser Ile
50                  55                  60

His His Gly Val Val Glu Val Asp Ala Ala Val Thr Pro Glu Glu Arg
65                  70                  75                  80

His Leu Ser Lys Met Gln Gln Asn Gly Tyr Glu Asn Pro Thr Tyr Lys
            85                  90                  95

Phe Phe Glu Gln Met Gln Asn
            100

(2) INFORMATION FOR SEQ ID NO:3:

(i) SEQUENCE CHARACTERISTICS:
       (A) LENGTH: 43 amino acids
       (B) TYPE: amino acid
       (D) TOPOLOGY: linear (ii) MOLECULE TYPE: peptide (v) FRAGMENT TYPE: internal (ix) FEATURE:
       (A) NAME/KEY: Modified site (B) LOCATION: 19
        (D) OTHER INFORMATION: /note= Xaa is a hydrophobic amino
            acid (ix) FEATURE:
        (A) NAME/KEY: Modified site
        (B) LOCATION: 20
        (D) OTHER INFORMATION: /note= Xaa is a hydrophobic amino
            acid (xi) SEQUENCE DESCRIPTION: SEQ ID NO:3:

Asp Ala Glu Phe Arg His Asp Ser Gly Tyr Glu Val His His Gln Lys
1               5                   10                  15

Leu Val Xaa Xaa Ala Glu Asp Val Gly Ser Asn Lys Gly Ala Ile Ile
            20                  25                  30

Gly Leu Met Val Gly Gly Val Val Ile Ala Thr
            35                  40

(2) INFORMATION FOR SEQ ID NO:4:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:4:

His Asp Ser Gly Tyr Glu Val His His Gln Lys Leu Val Phe Phe
                5                   10                  15

(2) INFORMATION FOR SEQ ID NO:5:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO:5:

His Gln Lys Leu Val Phe Phe Ala
                5

(2) INFORMATION FOR SEQ ID NO:6:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:6:

His Gln Lys Leu Val Phe Phe
                5

(2) INFORMATION FOR SEQ ID NO:7:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO:7:

Gln Lys Leu Val Phe Phe Ala

5

(2) INFORMATION FOR SEQ ID NO:8:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:8:

Gln Lys Leu Val Phe Phe
                5

(2) INFORMATION FOR SEQ ID NO:9:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:9:

Lys Leu Val Phe Phe Ala
                5

(2) INFORMATION FOR SEQ ID NO:10:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:10:

Lys Leu Val Phe Phe
                5

(2) INFORMATION FOR SEQ ID NO:11:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:11:

Leu Val Phe Phe Ala
                5

(2) INFORMATION FOR SEQ ID NO:12:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:12:

Leu Val Phe Phe (2) INFORMATION FOR SEQ ID NO:13:

```
    (i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:13:

Leu Ala Phe Phe Ala
1               5

(2) INFORMATION FOR SEQ ID NO:14:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:14:

Lys Leu Val Phe Phe Ala Glu Asp Val Gly Ser Asn Lys Gly Ala
1               5                  10                  15

(2) INFORMATION FOR SEQ ID NO:15:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:15:

Asp Ala Glu Phe Arg His Asp Ser Gly Tyr Glu Val His His Gln Lys
1               5                  10                  15

Leu Val Phe Phe Ser Asn Lys Gly Ala Ile Ile Gly Leu Met Val Gly
                20                  25                  30

Gly Val Val
        35

(2) INFORMATION FOR SEQ ID NO:16:

(i) SEQUENCE CHARACTERISTICS:
        (A) LENGTH: 35 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:16:

Glu Glu Val Val His His His His Gln Gln Lys Leu Val Phe Phe Ala
1               5                  10                  15

Glu Asp Val Gly Ser Asn Lys Gly Ala Ile Ile Gly Leu Met Val Gly
                20                  25                  30

Gly Val Val
        35

(2) INFORMATION FOR SEQ ID NO:17:
```

```
        (i) SEQUENCE CHARACTERISTICS:
            (A) LENGTH: 8 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:17:

Ala Gly Ala Ala Ala Ala Gly Ala
 1               5

(2) INFORMATION FOR SEQ ID NO:18:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (v) FRAGMENT TYPE: internal (xi) SEQUENCE DESCRIPTION: SEQ ID NO:18:

Ala Ile Leu Ser Ser
 1               5

(2) INFORMATION FOR SEQ ID NO:19:

(i) SEQUENCE CHARACTERISTICS:
            (A) LENGTH: 3 amino acids
            (B) TYPE: amino acid
            (D) TOPOLOGY: linear (ii) MOLECULE TYPE: peptide (xi) SEQUENCE DESCRIPTION: SEQ ID NO:19:

Val Phe Phe
 1

(2) INFORMATION FOR SEQ ID NO:20:

(i) SEQUENCE CHARACTERISTICS:
            (A) LENGTH: 3 amino acids
            (B) TYPE: amino acid
            (D) TOPOLOGY: linear (ii) MOLECULE TYPE: peptide (xi) SEQUENCE DESCRIPTION: SEQ ID NO:20:

Phe Phe Ala
 1

(2) INFORMATION FOR SEQ ID NO:21:

(i) SEQUENCE CHARACTERISTICS:
            (A) LENGTH: 5 amino acids
            (B) TYPE: amino acid
            (D) TOPOLOGY: linear (ii) MOLECULE TYPE: peptide (xi) SEQUENCE DESCRIPTION: SEQ ID NO:21:

Phe Phe Val Leu Ala
 1               5

(2) INFORMATION FOR SEQ ID NO:22:
```

```
        (i) SEQUENCE CHARACTERISTICS:
             (A) LENGTH: 5 amino acids
             (B) TYPE: amino acid
             (D) TOPOLOGY: linear (ii) MOLECULE TYPE: peptide (xi) SEQUENCE DESCRIPTION: SEQ ID NO:22:

Leu Val Phe Phe Lys
1               5

(2) INFORMATION FOR SEQ ID NO:23:

(i) SEQUENCE CHARACTERISTICS:
             (A) LENGTH: 5 amino acids
             (B) TYPE: amino acid
             (D) TOPOLOGY: linear (ii) MOLECULE TYPE: peptide (ix) FEATURE:
             (A) NAME/KEY: Modified site
             (B) LOCATION: 3
             (D) OTHER INFORMATION: /note= Xaa is iodotyrosyl (xi) SEQUENCE DESCRIPTION: SEQ ID NO:23:

Leu Val Xaa Phe Ala
1               5

(2) INFORMATION FOR SEQ ID NO:24:

(i) SEQUENCE CHARACTERISTICS:
             (A) LENGTH: 4 amino acids
             (B) TYPE: amino acid
             (D) TOPOLOGY: linear (ii) MOLECULE TYPE: peptide (xi) SEQUENCE DESCRIPTION: SEQ ID NO:24:

Val Phe Phe Ala
1

(2) INFORMATION FOR SEQ ID NO:25:

(i) SEQUENCE CHARACTERISTICS:
             (A) LENGTH: 5 amino acids
             (B) TYPE: amino acid
             (D) TOPOLOGY: linear (ii) MOLECULE TYPE: peptide (xi) SEQUENCE DESCRIPTION: SEQ ID NO:25:

Ala Val Phe Phe Ala
1               5

(2) INFORMATION FOR SEQ ID NO:26:

(i) SEQUENCE CHARACTERISTICS:
             (A) LENGTH: 5 amino acids
             (B) TYPE: amino acid
             (D) TOPOLOGY: linear (ii) MOLECULE TYPE: peptide (ix) FEATURE:
             (A) NAME/KEY: Modified site
             (B) LOCATION: 4
             (D) OTHER INFORMATION: /note= Xaa is iodotyrosyl (xi) SEQUENCE DESCRIPTION: SEQ ID NO:26:
```

```
Leu Val Phe Xaa Ala
1
```

(2) INFORMATION FOR SEQ ID NO:27:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:27:

```
Leu Val Phe Phe Ala Glu
1               5
```

(2) INFORMATION FOR SEQ ID NO:28:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:28:

```
Phe Phe Val Leu
1               5
```

(2) INFORMATION FOR SEQ ID NO:29:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:29:

```
Phe Lys Phe Val Leu
1               5
```

(2) INFORMATION FOR SEQ ID NO:30:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:30:

```
Lys Leu Val Ala Phe
1               5
```

(2) INFORMATION FOR SEQ ID NO:31:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Modified site
        (B) LOCATION: 6
        (D) OTHER INFORMATION: /note= Xaa is beta-alanyl (xi) SEQUENCE DESCRIPTION: SEQ ID NO:31:

Lys Leu Val Phe Phe Xaa
1

(2) INFORMATION FOR SEQ ID NO:32:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Modified site
        (B) LOCATION: 5
        (D) OTHER INFORMATION: /note= Xaa is D-alanyl (xi) SEQUENCE DESCRIPTION: SEQ ID NO:32:

Leu Val Phe Phe Xaa
1

(2) INFORMATION FOR SEQ ID NO:33:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:33:

Leu Val Ala Phe Ala
1               5

(2) INFORMATION FOR SEQ ID NO:34:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified-site
        (B) LOCATION: 5
        (D) OTHER INFORMATION: /note= aminoethyldibenzofuranyl-
            proprionic acid modification (xi) SEQUENCE DESCRIPTION: SEQ ID NO:34:

Asp Asp Ile Ile Leu
1               5

(2) INFORMATION FOR SEQ ID NO:35:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:35:

```
Ala Ala Ala Ala Ala
1               5
```

(2) INFORMATION FOR SEQ ID NO:36:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:36:

```
His Asp Ser Gly Tyr
1               5
```

(2) INFORMATION FOR SEQ ID NO:37:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:37:

```
Gln Lys Leu Val Phe
1               5
```

(2) INFORMATION FOR SEQ ID NO:38:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:38:

```
Lys Leu Thr Phe Phe
1               5
```

(2) INFORMATION FOR SEQ ID NO:39:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:39:

```
Lys Thr Val Phe Phe
1               5
```

(2) INFORMATION FOR SEQ ID NO:40:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:40:

Phe Phe Val Leu Ala
1               5

(2) INFORMATION FOR SEQ ID NO:41:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:41:

Leu Val Phe Ala Ala
1               5

(2) INFORMATION FOR SEQ ID NO:42:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:42:

Ala Val Ala Phe Ala
1               5

(2) INFORMATION FOR SEQ ID NO:43:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:43:

Leu Lys Leu Val Phe Phe
1               5

(2) INFORMATION FOR SEQ ID NO:44:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (v) FRAGMENT TYPE: internal (ix) FEATURE:
        (A) NAME/KEY: Modified site
        (B) LOCATION: 6
        (D) OTHER INFORMATION: /note= Xaa is N-methyl-Val (ix) FEATURE:
        (A) NAME/KEY: Modified site -continued

```
            (B) LOCATION: 9
            (D) OTHER INFORMATION: /note= aminoethyldibenzofuranyl-
                  proprionic acid modification (xi) SEQUENCE DESCRIPTION: SEQ ID NO:44:

Asp Asp Ile Ile Ile Xaa Asp Leu Leu
1               5

(2) INFORMATION FOR SEQ ID NO:45:

(i) SEQUENCE CHARACTERISTICS:
            (A) LENGTH: 8 amino acids
            (B) TYPE: amino acid
            (D) TOPOLOGY: linear (ii) MOLECULE TYPE: peptide (v) FRAGMENT TYPE: internal (ix) FEATURE:
            (A) NAME/KEY: Modified site
            (B) LOCATION: 5
            (D) OTHER INFORMATION: /note= Xaa is N-Methyl-Leu (ix) FEATURE:
            (A) NAME/KEY: Modified site
            (B) LOCATION: 8
            (D) OTHER INFORMATION: /note= aminoethyldibenzofuranyl-
                  proprionic acid modification (xi) SEQUENCE DESCRIPTION: SEQ ID NO:45:

Asp Asp Ile Ile Xaa Val Glu His
1               5
```